(12) United States Patent
Taggi et al.

(10) Patent No.: US 9,961,897 B2
(45) Date of Patent: May 8, 2018

(54) FUNGICIDAL PYRAZOLES

(71) Applicant: E. I. DU PONT DE NEMOURS AND COMPANY, Wilmington, DE (US)

(72) Inventors: Andrew Edmund Taggi, Newark, DE (US); James Francis Bereznak, Newtown Square, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days. days.

(21) Appl. No.: 14/913,509

(22) PCT Filed: Aug. 15, 2014

(86) PCT No.: PCT/US2014/051222
§ 371 (c)(1),
(2) Date: Feb. 22, 2016

(87) PCT Pub. No.: WO2015/026646
PCT Pub. Date: Feb. 26, 2015

(65) Prior Publication Data
US 2016/0212998 A1    Jul. 28, 2016

Related U.S. Application Data

(60) Provisional application No. 61/867,721, filed on Aug. 20, 2013.

(51) Int. Cl.
| | |
|---|---|
| *C07D 231/38* | (2006.01) |
| *C07C 331/28* | (2006.01) |
| *C07C 217/76* | (2006.01) |
| *A01N 43/56* | (2006.01) |
| *C07D 231/12* | (2006.01) |
| *C07D 231/18* | (2006.01) |
| *C07D 405/06* | (2006.01) |
| *C07D 405/12* | (2006.01) |

(52) U.S. Cl.
CPC .......... *A01N 43/56* (2013.01); *C07D 231/12* (2013.01); *C07D 231/18* (2013.01); *C07D 231/38* (2013.01); *C07D 405/06* (2013.01); *C07D 405/12* (2013.01)

(58) Field of Classification Search
None
See application file for complete search history.

(56) References Cited

U.S. PATENT DOCUMENTS 8,754,115 B2 *   6/2014   Long ............... A01N 43/56
514/406

* cited by examiner

*Primary Examiner* — Kamal Saeed
(74) *Attorney, Agent, or Firm* — Charlene Gross Sternberg

(57) ABSTRACT

Disclosed are compounds of Formula 1, including all geometric and stereoisomers, N-oxides, and salts thereof,

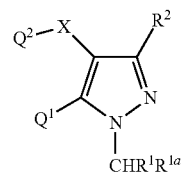

wherein $Q^1$, $Q^2$, X, $R^1$, $R^{1a}$ and $R^2$ are as defined in the disclosure. Also disclosed are compositions containing the compounds of Formula 1 and methods for controlling plant disease caused by a fungal pathogen comprising applying an effective amount of a compound or a composition of the invention.

7 Claims, No Drawings

FUNGICIDAL PYRAZOLES

FIELD OF THE INVENTION

This invention relates to certain pyrazoles, their N-oxides, salts and compositions, and methods of their use as fungicides.

BACKGROUND OF THE INVENTION

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different sites of action.

PCT Patent Publications WO 2009/137538, WO 2009/137651, WO 2010/101973, WO 2012/023143, WO 2012/030922 and WO 2012/031061 disclose pyrazole derivatives and their use as fungicides.

SUMMARY OF THE INVENTION

This invention is directed to compounds of Formula 1 (including all stereoisomers), N-oxides, and salts thereof, agricultural compositions containing them and their use as fungicides:

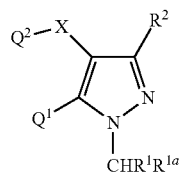

1 wherein
- $Q^1$ is a phenyl ring or a naphthalenyl ring system, each ring or ring system optionally substituted with up to 5 substituents independently selected from $R^{3a}$ and $R^{3b}$; or a 5- to 6-membered fully unsaturated heterocyclic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^{27})_v$, each ring or ring system optionally substituted with up to 5 substituents independently selected from $R^{3a}$ and $R^{3b}$ on carbon atom ring members and selected from cyano, $C_1$-$C_4$ alkyl, $C_2$-$C_4$ alkenyl, $C_2$-$C_4$ alkynyl, $C_3$-$C_6$ cycloalkyl, $C_2$-$C_4$ alkoxyalkyl, $C_1$-$C_4$ alkoxy, $C_2$-$C_4$ alkylcarbonyl, $C_2$-$C_4$ alkoxycarbonyl, $C_2$-$C_4$ alkylaminoalkyl and $C_3$-$C_4$ dialkylaminoalkyl on nitrogen atom ring members;
- $Q^2$ is a phenyl ring or a naphthalenyl ring system, each ring or ring system optionally substituted with up to 5 substituents independently selected from $R^{3a}$ and $R^{3b}$; or a 5- to 6-membered fully unsaturated heterocyclic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^{27})_v$, each ring or ring system optionally substituted with up to 5 substituents independently selected from $R^{3a}$ and $R^{3b}$ on carbon atom ring members and selected from cyano, $C_1$-$C_4$ alkyl, $C_2$-$C_4$ alkenyl, $C_2$-$C_4$ alkynyl, $C_3$-$C_6$ cycloalkyl, $C_2$-$C_4$ alkoxyalkyl, $C_1$-$C_4$ alkoxy, $C_2$-$C_4$ alkylcarbonyl, $C_2$-$C_4$ alkoxycarbonyl, $C_2$-$C_4$ alkylaminoalkyl and $C_3$-$C_4$ dialkylaminoalkyl on nitrogen atom ring members;
- X is O, $S(=O)_m$, $NR^4$ or $CR^{5a}OR^{5b}$;
- $R^1$ is H, cyano, halogen, $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_2$-$C_6$ alkoxyalkyl, $C_1$-$C_6$ alkoxy, $C_1$-$C_6$ haloalkoxy, —C(=O)OR$^6$ or —C(=O)NR$^7$R$^8$;
- $R^{1a}$ is H; or
- $R^{1a}$ and $R^1$ are taken together with the carbon atom to which they are attached to form a cyclopropyl ring optionally substituted with up to 2 substituents independently selected from halogen and methyl;
- $R^2$ is H, cyano, halogen, $C_1$-$C_3$ alkyl, $C_2$-$C_3$ alkenyl, $C_2$-$C_3$ alkynyl, $C_1$-$C_3$ haloalkyl, $C_2$-$C_3$ haloalkenyl, $C_2$-$C_3$ cyanoalkyl, $C_1$-$C_3$ hydroxyalkyl, $C_1$-$C_3$ alkoxy or $C_1$-$C_3$ alkylthio; or cyclopropyl optionally substituted with up to 2 substituents independently selected from halogen and methyl;
- each $R^{3a}$ is independently amino, cyano, halogen, hydroxy, nitro, $C_1$-$C_3$ alkyl, $C_1$-$C_3$ haloalkyl, $C_2$-$C_4$ alkenyl, $C_2$-$C_4$ alkynyl, $C_3$-$C_6$ cycloalkyl, $C_3$-$C_6$ halocycloalkyl, $C_4$-$C_6$ cycloalkylalkyl, $C_4$-$C_6$ alkylcycloalkyl, $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl, $C_1$-$C_3$ haloalkylsulfonyl, $C_1$-$C_3$ alkoxy, $C_1$-$C_3$ haloalkoxy, $C_3$-$C_6$ cycloalkoxy, $C_1$-$C_3$ alkylsulfonyloxy, $C_1$-$C_3$ haloalkylsulfonyloxy, $C_2$-$C_4$ alkylcarbonyloxy, $C_2$-$C_4$ alkylcarbonyl, $C_1$-$C_3$ alkylamino, $C_2$-$C_4$ dialkylamino, $C_2$-$C_4$ alkylcarbonylamino, —CH(=O), —NHCH(=O), —SF$_5$, —SC≡N or —U—V-T;
- each $R^{3b}$ is independently $C_4$-$C_8$ alkyl, $C_4$-$C_8$ haloalkyl, $C_5$-$C_8$ alkenyl, $C_2$-$C_8$ haloalkenyl, $C_5$-$C_8$ alkynyl, $C_2$-$C_8$ haloalkynyl, $C_1$-$C_8$ nitroalkyl, $C_2$-$C_8$ nitroalkenyl, $C_7$-$C_8$ cycloalkyl, $C_7$-$C_8$ halocycloalkyl, $C_7$-$C_8$ cycloalkylalkyl, $C_7$-$C_8$ alkylcycloalkyl, $C_5$-$C_{12}$ cycloalkylalkenyl, $C_5$-$C_{12}$ cycloalkylalkynyl, $C_6$-$C_{12}$ cycloalkylcycloalkyl, $C_4$-$C_8$ alkylthio, $C_4$-$C_8$ haloalkylthio, $C_4$-$C_8$ alkylsulfinyl, $C_4$-$C_8$ haloalkylsulfinyl, $C_4$-$C_8$ alkylsulfonyl, $C_4$-$C_8$ haloalkylsulfonyl, $C_4$-$C_8$ alkoxy, $C_4$-$C_8$ haloalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_7$-$C_{12}$ cycloalkoxy, $C_3$-$C_{12}$ halocycloalkoxy, $C_4$-$C_{12}$ cycloalkylalkoxy, $C_5$-$C_{12}$ cycloalkylalkenyloxy, $C_5$-$C_{12}$ cycloalkylalkynyloxy, $C_4$-$C_8$ alkylsulfonyloxy, $C_4$-$C_8$ haloalkylsulfonyloxy, $C_5$-$C_8$ alkylcarbonyloxy, $C_5$-$C_8$ alkylcarbonyl, $C_4$-$C_8$ alkylamino, $C_5$-$C_8$ alkylcarbonylamino, $C_3$-$C_{12}$ trialkylsilyl, $C_4$-$C_{12}$ trialkylsilylalkyl, $C_4$-$C_{12}$ trialkylsilylalkoxy, —C(=S)NR$^{9a}$R$^{9b}$, —CR$^{10a}$=NOR$^{10b}$, —CR$^{10c}$=NNR$^{9a}$R$^{9b}$, —NR$^{9a}$N=CR$^{11a}$R$^{11b}$, —ON=CR$^{11a}$R$^{11b}$ or -A(CR$^{12a}$R$^{12b}$)$_n$W;
- each A is independently O or a direct bond;
- each W is independently a 3- to 7-membered heterocyclic ring containing ring members selected from carbon atoms and 1 to 4 heteroatoms independently selected from up to 2 O, up to 2 S and up to 4 N atoms, wherein up to 3 carbon atom ring members are independently selected from C(=O) and C(=S), the ring optionally substituted with up to 3 substituents independently selected from $R^{13}$ on carbon atom ring members and $R^{14}$ on nitrogen atom ring members;

$R^4$ is H, amino, $C_2$-$C_6$ alkenyl, $C_3$-$C_6$ alkynyl, $C_3$-$C_6$ cycloalkyl, —CH(=O), —S(=O)$_2$OM, —S(=O)$_m$R$^{15}$, —(C=Z)R$^{16}$ or OR$^{17}$; or $C_1$-$C_6$ alkyl or $C_1$-$C_6$ haloalkyl, each optionally substituted with up to 2 substituents independently selected from $R^{18}$;

$R^{5a}$ is H or $C_1$-$C_6$ alkyl;

$R^{5b}$ is H, —CH(=O), $C_1$-$C_6$ alkyl, $C_1$-$C_6$ haloalkyl, $C_2$-$C_6$ alkenyl, $C_3$-$C_6$ alkynyl, $C_3$-$C_6$ cycloalkyl, $C_3$-$C_6$ halocycloalkyl, $C_2$-$C_6$ cyanoalkyl, $C_2$-$C_6$ alkoxyalkyl, $C_2$-$C_6$ alkylcarbonyl, $C_2$-$C_6$ alkoxycarbonyl, $C_2$-$C_6$ (alkylthio)carbonyl, $C_4$-$C_8$ cycloalkylcarbonyl, $C_4$-$C_8$ cycloalkoxycarbonyl, $C_4$-$C_8$ (cycloalkylthio)carbonyl, $C_2$-$C_6$ alkoxy(thiocarbonyl) or $C_4$-$C_8$ cycloalkoxy(thiocarbonyl);

$R^6$ is H, $C_1$-$C_6$ alkyl or $C_1$-$C_6$ haloalkyl;

$R^7$ and $R^8$ are each independently H, $C_1$-$C_6$ alkyl, $C_1$-$C_6$ haloalkyl, $C_3$-$C_6$ cycloalkyl, $C_4$-$C_8$ cycloalkylalkyl or $C_4$-$C_8$ alkylcycloalkyl; or $R^7$ and $R^8$ are taken together with the nitrogen atom to which they are attached to form a 4- to 7-membered nonaromatic heterocyclic ring containing ring members, in addition to the connecting nitrogen atom, selected from carbon atoms and up to 1 ring member selected from O, S(=O)$_m$ and NR$^{19}$;

each $R^{9a}$ and $R^{9b}$ is independently H, $C_1$-$C_4$ alkyl or $C_1$-$C_4$ haloalkyl;

each $R^{10a}$ is independently H, $C_1$-$C_3$ alkyl or $C_1$-$C_3$ haloalkyl;

each $R^{10b}$ and $R^{10c}$ is independently H, $C_1$-$C_3$ alkyl, $C_1$-$C_3$ haloalkyl, $C_2$-$C_4$ alkenyl, $C_2$-$C_4$ haloalkenyl, $C_2$-$C_4$ alkynyl, $C_3$-$C_4$ cycloalkyl, $C_3$-$C_4$ halocycloalkyl or $C_4$-$C_8$ cycloalkylalkyl;

each $R^{11a}$ and $R^{11b}$ is independently H, $C_1$-$C_3$ alkyl or $C_1$-$C_3$ haloalkyl;

each $R^{12a}$ is independently H, cyano, halogen or $C_1$-$C_4$ alkyl;

each $R^{12b}$ is independently H or $C_1$-$C_4$ alkyl;

each $R^{13}$ is independently cyano, halogen, $C_1$-$C_2$ alkyl, $C_1$-$C_2$ haloalkyl, $C_1$-$C_2$ alkoxy, $C_1$-$C_2$ haloalkoxy or $C_2$-$C_4$ alkoxyalkyl;

each $R^{14}$ is independently cyano, $C_1$-$C_2$ alkyl or $C_1$-$C_2$ alkoxy;

$R^{15}$ is $C_1$-$C_6$ alkyl or $C_1$-$C_6$ haloalkyl;

$R^{16}$ is $C_1$-$C_6$ alkyl, $C_2$-$C_6$ alkylthioalkyl, $C_2$-$C_6$ alkoxyalkyl, $C_2$-$C_6$ alkylaminoalkyl, $C_3$-$C_6$ dialkylaminoalkyl, $C_1$-$C_6$ alkoxy or $C_1$-$C_6$ alkylthio;

$R^{17}$ is H, —CH(=O), $C_3$-$C_6$ cycloalkyl, —S(=O)$_2$OM or —(C=Z)R$^{20}$; or $C_1$-$C_6$ alkyl or $C_1$-$C_6$ haloalkyl, each optionally substituted with up to 2 substituents independently selected from $R^{21}$;

each $R^{18}$ and $R^{21}$ is independently cyano, $C_3$-$C_6$ cycloalkyl, $C_1$-$C_6$ alkoxy, $C_1$-$C_6$ haloalkoxy, $C_1$-$C_6$ alkylthio, $C_1$-$C_6$ alkylsulfinyl or $C_1$-$C_6$ alkylsulfonyl;

$R^{19}$ is H, $C_1$-$C_3$ alkyl or $C_2$-$C_3$ haloalkyl;

$R^{20}$ is $C_1$-$C_6$ alkyl, $C_2$-$C_6$ alkoxyalkyl, $C_2$-$C_6$ alkylthioalkyl, $C_2$-$C_6$ alkylaminoalkyl, $C_3$-$C_6$ dialkylaminoalkyl, $C_1$-$C_6$ alkoxy or $C_1$-$C_6$ alkylthio;

each U is independently O, S(=O)$_m$, NR$^{22}$ or a direct bond;

each V is independently $C_1$-$C_6$ alkylene, $C_2$-$C_6$ alkenylene, $C_3$-$C_6$ alkynylene, $C_3$-$C_6$ cycloalkylene or $C_3$-$C_6$ cycloalkenylene, wherein up to 3 carbon atoms are C(=O), each optionally substituted with up to 5 substituents independently selected from halogen, cyano, nitro, hydroxy, $C_1$-$C_6$ alkyl, $C_1$-$C_6$ haloalkyl, $C_1$-$C_6$ alkoxy and $C_1$-$C_6$ haloalkoxy;

each T is independently cyano, NR$^{23a}$R$^{23b}$, OR$^{24}$ or S(=O)$_m$R$^{25}$;

each $R^{22}$ is independently H, $C_1$-$C_6$ alkyl, $C_1$-$C_6$ haloalkyl, $C_2$-$C_6$ alkylcarbonyl, $C_2$-$C_6$ alkoxycarbonyl, $C_2$-$C_6$ (alkylthio)carbonyl, $C_2$-$C_6$ alkoxy(thiocarbonyl), $C_4$-$C_8$ cycloalkylcarbonyl, $C_4$-$C_8$ cycloalkoxycarbonyl, $C_4$-$C_8$ (cycloalkylthio)carbonyl or $C_4$-$C_8$ cycloalkoxy(thiocarbonyl);

each $R^{23a}$ and $R^{23b}$ is independently H, $C_1$-$C_6$ alkyl, $C_1$-$C_6$ haloalkyl, $C_2$-$C_6$ alkenyl, $C_3$-$C_6$ alkynyl, $C_3$-$C_6$ cycloalkyl, $C_3$-$C_6$ halocycloalkyl, $C_2$-$C_6$ alkylcarbonyl, $C_2$-$C_6$ alkoxycarbonyl, $C_2$-$C_6$ (alkylthio)carbonyl, $C_2$-$C_6$ alkoxy(thiocarbonyl), $C_4$-$C_8$ cycloalkylcarbonyl, $C_4$-$C_8$ cycloalkoxycarbonyl, $C_4$-$C_8$ (cycloalkylthio)carbonyl or $C_4$-$C_8$ cycloalkoxy(thiocarbonyl); or a pair of $R^{23a}$ and $R^{23b}$ attached to the same nitrogen atom are taken together with the nitrogen atom to form a 3- to 6-membered heterocyclic ring, the ring optionally substituted with up to 5 substituents independently selected from $R^{26}$;

each $R^{24}$ and $R^{25}$ is independently H, $C_1$-$C_6$ alkyl, $C_1$-$C_6$ haloalkyl, $C_2$-$C_6$ alkenyl, $C_3$-$C_6$ alkynyl, $C_3$-$C_6$ cycloalkyl, $C_3$-$C_6$ halocycloalkyl, $C_2$-$C_6$ alkylcarbonyl, $C_2$-$C_6$ alkoxycarbonyl, $C_2$-$C_6$ (alkylthio)carbonyl, $C_4$-$C_8$ cycloalkylcarbonyl, $C_4$-$C_8$ cycloalkoxycarbonyl, $C_4$-$C_8$ (cycloalkylthio)carbonyl, $C_2$-$C_6$ alkoxy(thiocarbonyl) or $C_4$-$C_8$ cycloalkoxy(thiocarbonyl);

each $R^{26}$ is independently halogen, $C_1$-$C_6$ alkyl, $C_1$-$C_6$ haloalkyl or $C_1$-$C_6$ alkoxy;

each $R^{27}$ is independently H, cyano, $C_1$-$C_3$ alkyl or $C_1$-$C_3$ haloalkyl;

Z is O or S;

M is K, Na or Li;

each m is independently 0, 1 or 2;

each n is independently 0, 1, 2 or 3; and each u and v are independently 0, 1 or 2 in each instance of S(=O)$_u$(=NR$^{27}$)$_v$; provided that:

(a) the sum of u and v is 0, 1 or 2;

(b) when $Q^1$ and $Q^2$ are each an optionally substituted phenyl ring, an optionally substituted naphthalenyl ring system, an optionally substituted 5- to 6-membered fully unsaturated heterocyclic ring or an optionally substituted 8- to 10-membered heteroaromatic bicyclic ring system, then at least one of $Q^1$ or $Q^2$ is substituted with at least one $R^{3b}$; and (c) when n is 1, 2, or 3, then W is linked through a carbon atom to the remainder of Formula 1.

More particularly, this invention pertains to a compound selected from compounds of Formula 1 (including all stereoisomers) and N-oxides and salts thereof.

This invention also relates to a fungicidal composition comprising (a) a compound of the invention (i.e. in a fungicidally effective amount); and (b) at least one additional component selected from the group consisting of surfactants, solid diluents and liquid diluents.

This invention also relates to a fungicidal composition comprising (a) a compound of the invention; and (b) at least one other fungicide (e.g., at least one other fungicide having a different site of action).

This invention further relates to a method for controlling plant diseases caused by fungal plant pathogens comprising applying to the plant or portion thereof, or to the plant seed, a fungicidally effective amount of a compound of the invention (e.g., as a composition described herein).

This invention also relates to a composition comprising a compound of Formula 1, an N-oxide, or a salt thereof, and at least one invertebrate pest control compound or agent.

DETAILS OF THE INVENTION

As used herein, the terms "comprises", "comprising", "includes", "including", "has", "having", "contains", "containing", "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method or apparatus that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium (e.g., soil), such as roots, tubers, bulbs and corms, and also members growing above the growing medium, such as foliage (including stems and leaves), flowers, fruits and seeds.

As referred to herein, the term "seedling", used either alone or in a combination of words means a young plant developing from the embryo of a seed.

As referred to herein, the term "broadleaf" used either alone or in words such as "broadleaf crop" means dicot or dicotyledon, a term used to describe a group of angiosperms characterized by embryos having two cotyledons.

As used herein, the term "alkylating agent" refers to a chemical compound in which a carbon-containing radical is bound through a carbon atom to a leaving group such as halide or sulfonate, which is displaceable by bonding of a nucleophile to said carbon atom. Unless otherwise indicated, the term "alkylating agent" or "alkylating reagent" does not limit the carbon-containing radical to alkyl; the carbon-containing radicals in alkylating agents include the variety of carbon-bound substituent radicals specified, for example, for $R^1$ and $R^2$.

Generally when a molecular fragment (i.e. radical) is denoted by a series of atom symbols (e.g., C, H, N, O and S) the implicit point or points of attachment will be easily recognized by those skilled in the art. In some instances herein, particularly when alternative points of attachment are possible, the point or points of attachment may be explicitly indicated by a hyphen ("-"). For example, "—SCN" indicates that the point of attachment is the sulfur atom (i.e. thiocyanato, not isothiocyanato).

In the above recitations, the term "alkyl", used either alone or in compound words such as "alkylthio" or "haloalkyl" includes straight-chain or branched alkyl such as methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" also includes moieties comprised of multiple triple bonds such as 2,5-hexadiynyl. "Alkylene" denotes a straight-chain or branched alkanediyl. Examples of "alkylene" include $CH_2$, $CH_2CH_2$, $CH(CH_3)$, $CH_2CH_2CH_2$, $CH_2CH(CH_3)$, and the different butylene, pentylene or hexylene isomers. "Alkenylene" denotes a straight-chain or branched alkenediyl containing one olefinic bond. Examples of "alkenylene" include $CH=CH$, $CH_2CH=CH$ and $CH=C(CH_3)$. "Alkynylene" denotes a straight-chain or branched alkynediyl containing one triple bond. Examples of "alkynylene" include $CH_2C\equiv C$, $C\equiv CCH_2$, and the different butynylene, pentynylene or hexynylene isomers.

"Alkylamino" includes an NH radical substituted with straight-chain or branched alkyl. Examples of "alkylamino" include $CH_3CH_2NH$, $CH_3CH_2CH_2NH$ and $(CH_3)_2CHNH$. Examples of "dialkylamino" include $(CH_3)_2N$, $(CH_3CH_2)_2N$ and $CH_3CH_2(CH_3)N$. "Alkylaminoalkyl" denotes alkylamino substitution on alkyl. Examples of "alkylaminoalkyl" include $CH_3NHCH_2$, $CH_3NHCH_2CH_2$ and $CH_3CH_2NHCH_2$. Examples of "dialkylaminoalkyl" include $(CH_3)_2NCH_2$, $CH_3CH_2(CH_3)NCH_2$ and $(CH_3)_2NCH_2CH_2$.

"Alkoxy" includes, for example, methoxy, ethoxy, n-propyloxy, i-propyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkenyloxy" includes straight-chain or branched alkenyl attached to and linked through an oxygen atom. Examples of "alkenyloxy" include $H_2C=CHCH_2O$, $(CH_3)_2C=CHCH_2O$, $CH_3CH=CHCH_2O$, $CH_3CH=C(CH_3)CH_2O$ and $H_2C=CHCH_2CH_2O$. "Alkynyloxy" includes straight-chain or branched alkynyl attached to and linked through an oxygen atom. Examples of "alkynyloxy" include $HC\equiv CCH_2O$, $CH_3C\equiv CCH_2O$ and $CH_3C\equiv CCH_2CH_2O$. The term "alkylsulfonyloxy" denotes alkylsulfonyl attached to and linked through an oxygen atom. Examples of "alkylsulfonyloxy" include $CH_3S(=O)_2O$, $CH_3CH_2S(=O)_2O$, $CH_3CH_2CH_2S(=O)_2O$ and $(CH_3)_2CHS(=O)_2O$.

"Alkylthio" includes branched or straight-chain alkylthio moieties such as methylthio, ethylthio, and the different propylthio isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Alkylsulfinyl" includes both enantiomers of an alkylsulfinyl group. Examples of "alkylsulfinyl" include $CH_3S(=O)$, $CH_3CH_2S(=O)$, $CH_3CH_2CH_2S(=O)$ and $(CH_3)_2CHS(=O)$. Examples of "alkylsulfonyl" include $CH_3S(=O)_2$, $CH_3CH_2S(=O)_2$, $CH_3CH_2CH_2S(=O)_2$ and $(CH_3)_2CHS(=O)_2$.

The term "cycloalkyl" denotes a saturated carbocyclic ring consisting of between 3 to 8 carbon atoms linked to one another by single bonds. Examples of "cycloalkyl" include cyclopropyl, cyclobutyl, cyclopentyl and cyclohexyl. The term "cycloalkylalkyl" denotes cycloalkyl substitution on an alkyl group. Examples of "cycloalkylalkyl" include cyclopropylmethyl, cyclopentylethyl, and other cycloalkyl moieties bonded to straight-chain or branched alkyl groups. "Alkylcycloalkyl" denotes alkyl substitution on a cycloalkyl moiety. Examples include 4-methylcyclohexyl and 3-ethylcyclopentyl. The term "cycloalkylcycloalkyl" denotes cycloalkyl substitution on another cycloalkyl ring, wherein each cycloalkyl ring independently has from 3 to 6 carbon atom ring members. Examples of "cycloalkylcycloalkyl" include cyclopropylcyclopropyl (such as 1,1'-bicyclopropyl-1-yl, 1,1'-bicyclopropyl-2-yl), cyclohexylcyclopentyl (such as 4-cyclopentylcyclohexyl) and cyclohexylcyclohexyl (such as 1,1'-bicyclohexyl-1-yl), and the different cis- and trans-cycloalkylcycloalkyl isomers, (such as (1R,2S)-1,1'-bicyclopropyl-2-yl and (1R,2R)-1,1'-bicyclopropyl-2-yl). The term "cycloalkoxy" denotes cycloalkyl attached to and linked through an oxygen atom such as cyclopentyloxy and cyclohexyloxy. "Cycloalkylalkoxy" denotes cycloalkyl substitution on an alkoxy group. Examples of "cycloalkylalkoxy" include cyclopropylmethoxy, cyclopentylethoxy, and other cycloalkyl moieties bonded to straight-chain or branched alkoxy groups. "Cycloalkylcarbonyl" denotes cycloalkyl bonded to a $C(=O)$ group including, for example, cyclopropylcarbonyl and cyclopentylcarbonyl. The term "cycloalkoxycarbonyl" means cycloalkoxy bonded to a $C(=O)$ group, for example, cyclopropyloxycarbonyl and cyclopentyloxycarbonyl. The term "cycloalkylene" denotes a cycloalkanediyl ring. Examples of "cycloalkylene" include cyclopropylene, cyclobutylene, cyclopentylene and cyclohexylene. The term "cycloalkenylene" denotes a cycloalkenediyl ring containing one olefinic bond. Examples of "cycloalkenylene" include cyclopropenylene and cyclopentenylene.

"Cyanoalkyl" denotes an alkyl group substituted with one cyano group. Examples of "cyanoalkyl" include $NCCH_2$, $NCCH_2CH_2$ and $CH_3CH(CN)CH_2$. "Hydroxyalkyl" denotes an alkyl group substituted with one hydroxy group. Examples of "hydroxyalkyl" include $HOCH_2$, $HOCH_2CH_2$ and $CH_3CH_2(OH)CH$. "Nitroalkyl" denotes an alkyl group substituted with one nitro group. Examples of "nitroalkyl" include $NO_2CH_2$ and $NO_2CH_2CH_2$.

"Alkylcarbonyl" denotes a straight-chain or branched alkyl group bonded to a $C(=O)$ moiety. Examples of "alkylcarbonyl" include $CH_3C(=O)$, $CH_3CH_2CH_2C(=O)$ and $(CH_3)_2CHC(=O)$. Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different pentoxy- or hexoxycarbonyl isomers. The term "alkylcarbonyloxy" denotes a straight-chain or branched alkyl bonded to a $C(=O)O$ moiety. Examples of "alkylcarbonyloxy" include $CH_3CH_2C(=O)O$ and $(CH_3)_2CHC(=O)O$. "(Alkylthio)carbonyl" denotes a straight-chain or branched alkylthio group bonded to a $C(=O)$ moiety. Examples of "(alkylthio)carbonyl" include $CH_3SC(=O)$, $CH_3CH_2CH_2SC(=O)$ and $(CH_3)_2CHSC(=O)$. "Alkoxy(thiocarbonyl)" denotes a straight-chain or branched alkoxy group bonded to a $C(=S)$ moiety. Examples of "alkoxy(thiocarbonyl)" include $CH_3OC(=S)$, $CH_3CH_2CH_2OC(=S)$ and $(CH_3)_2CHOC(=S)$. The term "alkylcarbonylamino" denotes alkyl bonded to a $C(=O)NH$ moiety. Examples of "alkylcarbonylamino" include $CH_3C(=O)NH$ and $CH_3CH_2C(=O)NH$.

"Trialkylsilyl" includes 3 branched and/or straight-chain alkyl radicals attached to and linked through a silicon atom, such as trimethylsilyl, triethylsilyl and tert-butyldimethylsilyl.

The term "halogen", either alone or in compound words such as "halomethyl", "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkoxy", "haloalkylthio", "haloalkylsulfinyl", "haloalkylsulfonyl" and "halocycloalkyl" are defined analogously to the term "haloalkyl". Examples of "haloalkenyl" include $Cl_2C=CHCH_2$ and $CF_3CH_2=CH$. Examples of "haloalkoxy" include $CF_3O$, $CCl_3CH_2O$, $F_2CHCH_2CH_2O$ and $CF_3CH_2O$. Examples of "haloalkylthio" include $CCl_3S$, $CF_3S$, $CCl_3CH_2S$ and $ClCH_2CH_2CH_2S$. Examples of "haloalkylsulfinyl" include $CF_3S(=O)$, $CCl_3S(=O)$, $CF_3CH_2S(=O)$ and $CF_3CF_2S(=O)$. Examples of "haloalkylsulfonyl" include $CF_3S(=O)_2$, $CCl_3S(=O)_2$, $CF_3CH_2S(=O)_2$ and $CF_3CF_2S(=O)_2$. Examples of "halocycloalkyl" include chlorocyclopropyl, fluorocyclobutyl and chlorocyclohexyl.

The total number of carbon atoms in a substituent group is indicated by the "$C_i$-$C_j$" prefix where i and j are numbers from 1 to 12. For example, $C_1$-$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

The term "unsubstituted" in connection with a group such as a ring means the group does not have any substituents other than its one or more attachments to the remainder of Formula 1. The term "optionally substituted" means that the number of substituents can be zero. Unless otherwise indicated, optionally substituted groups may be substituted with as many optional substituents as can be accommodated by replacing a hydrogen atom with a non-hydrogen substituent on any available carbon or nitrogen atom. Commonly, the number of optional substituents (when present) range from 1 to 3. As used herein, the term "optionally substituted" is used interchangeably with the phrase "substituted or unsubstituted" or with the term "(un)substituted."

The number of optional substituents may be restricted by an expressed limitation. For example, the phrase "optionally substituted with up to 3 substituents independently selected from $R^{3a}$ on carbon atom ring members" means that 0, 1, 2 or 3 substituents can be present (if the number of potential connection points allows). Similarly, the phrase "optionally substituted with up to 5 substituents independently selected from $R^{3a}$" means that 0, 1, 2, 3, 4 or 5 substituents can be present if the number of available connection points allows.

When a compound is substituted with a substituent bearing a subscript that indicates the number of said substituents can vary (e.g., $(R^{3a})_p$ in Table 1 wherein p is 0 to 5), then said substituents are independently selected from the group of defined substituents, unless otherwise indicated. When a variable group is shown to be optionally attached to a position, for example $(R^{3a})_p$ in Table 1 wherein p may be 0, then hydrogen may be at the position even if not recited in the definition of the variable group.

Unless otherwise indicated, a "ring" or "ring system" as a component of Formula 1 (e.g., $Q^1$ or $Q^2$) is carbocyclic (e.g., phenyl or naphthalenyl) or heterocyclic (e.g., pyridinyl). The term "ring member" refers to an atom (e.g., C, O, N or S) forming the backbone of a ring. The term "ring system" denotes two or more fused rings (e.g., quinazolinyl).

The term "nonaromatic" includes rings that are fully saturated as well as partially or fully unsaturated, provided that none of the rings are aromatic. The term "aromatic" indicates that each of the ring atoms of a fully unsaturated ring are essentially in the same plane and have a p-orbital perpendicular to the ring plane, and that (4n+2) π electrons, where n is a positive integer, are associated with the ring to comply with Hickel's rule.

The terms "carbocyclic ring" or "carbocycle" denote a ring wherein the atoms forming the ring backbone are selected only from carbon. When a fully unsaturated carbocyclic ring satisfies Hickel's rule, then said ring is also called an "aromatic carbocyclic ring". The term "saturated carbocyclic ring" refers to a ring having a backbone consisting of carbon atoms linked to one another by single bonds; unless otherwise specified, the remaining carbon valences are occupied by hydrogen atoms.

The terms "heterocyclic ring", "heterocycle" or "heteroaromatic ring system" denote a ring or ring system in which at least one atom forming the ring backbone is not carbon (e.g., N, O or S). Typically a heterocyclic ring contains no more than 3 N atoms, no more than 2 O atoms and no more than 2 S atoms. Unless otherwise indicated, a heterocyclic ring can be a saturated, partially unsaturated or fully unsaturated ring. When a fully unsaturated heterocyclic ring satisfies Hickel's rule, then said ring is also called a "heteroaromatic ring" or "aromatic heterocyclic ring". Unless otherwise indicated, heterocyclic rings can be attached through any available carbon or nitrogen by replacement of a hydrogen on said carbon or nitrogen.

In the context of the present invention when an instance of $Q^1$ and $Q^2$ comprises a phenyl or 6-membered heterocyclic ring (e.g., pyridinyl), the ortho, meta and para positions of each ring are relative to the connection of the ring to the remainder of Formula 1.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

One skilled in the art recognizes that some of the compounds disclosed herein can exist in equilibrium with one or more of their respective tautomeric counterparts. Unless otherwise indicated, reference to a compound by one tautomer description is to be considered to include all tautomers.

One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of Formula 1 are useful for control of plant diseases caused by fungal plant pathogens (i.e. are agriculturally suitable). The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

Compounds selected from Formula 1, stereoisomers, N-oxides, and salts thereof, typically exist in more than one form, therefore Formula 1 includes all crystalline and non-crystalline forms of the compounds that Formula 1 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due to the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 can exhibit beneficial effects (e.g., suitability for preparation of useful formulations, improved biological performance) relative to another polymorph or a mixture of polymorphs of the same compound represented by Formula 1. Preparation and isolation of a particular polymorph of a compound represented by Formula 1 can be achieved by methods known to those skilled in the art including, for example, crystallization using selected solvents and temperatures.

Embodiments of the present invention as described in the Summary of the Invention include those described below. In the following Embodiments, Formula 1 includes stereoisomers, N-oxides and salts thereof, and reference to "a compound of Formula 1" includes the definitions of substituents specified in the Summary of the Invention unless further defined in the Embodiments.

Embodiment 1

A compound of Formula 1 wherein $Q^1$ is a phenyl, pyridinyl, pyrimidinyl, pyrazinyl or pyridazinyl ring, each ring optionally substituted with up to 3 substituents independently selected from $R^{3a}$ and $R^{3b}$.

Embodiment 2

A compound of Embodiment 1 wherein $Q^1$ is a phenyl ring optionally substituted with up to 3 substituents independently selected from $R^{3a}$ and $R^{3b}$.

Embodiment 3

A compound of Formula 1 wherein $Q^1$ is a phenyl ring optionally substituted with up to 2 substituents independently selected from $R^{3a}$ and substituted with 1 to 2 substituents independently selected from $R^{3b}$.

Embodiment 4

A compound of Embodiment 3 wherein $Q^1$ is a phenyl ring optionally substituted with up to 2 substituents independently selected from $R^{3a}$ and substituted with 1 substituent selected from $R^{3b}$.

Embodiment 5

A compound of Embodiment 4 wherein $Q^1$ is a phenyl ring optionally substituted with up to 1 substituent selected from $R^{3a}$ and substituted with 1 substituent selected from $R^{3b}$.

Embodiment 6

A compound of Formula 1 or any one of Embodiments 1 through 5 wherein $Q^1$ is a phenyl ring substituted with 1 to 3 substituents independently selected from $R^{3a}$ and $R^{3b}$.

Embodiment 7

A compound of Embodiment 6 wherein $Q^1$ is a phenyl ring substituted with 2 substituents independently selected from $R^{3a}$ and 1 substituent selected from $R^{3b}$.

Embodiment 8

A compound of Embodiment 7 wherein $Q^1$ is a phenyl ring substituted with 1 substituent selected from $R^{3a}$ and 1 substituent selected from $R^{3b}$.

Embodiment 9

A compound of Formula 1 or any one of Embodiments 1 through 8 wherein $Q^1$ is a phenyl ring substituted with at least 1 substituent selected from $R^{3a}$ which is attached at an ortho position (relative to the connection of the $Q^1$ ring to the remainder of Formula 1).

Embodiment 10

A compound of Formula 1 or any one of Embodiments 1 through 9 wherein $Q^1$ is a phenyl ring substituted with at least 1 substituent selected from $R^{3b}$ which is attached at the para position (relative to the connection of the $Q^1$ ring to the remainder of Formula 1).

Embodiment 11

A compound of Formula 1 or any one of Embodiments 1 through 10 wherein $Q^1$ is a phenyl ring substituted with 2 substituents independently selected from $R^{3a}$ which are attached at the 2- and 6-positions and 1 substituent selected from $R^{3b}$ which is attached at the 4-position (relative to the connection of the $Q^1$ ring to the remainder of Formula 1).

Embodiment 12

A compound of Formula 1 or any one of Embodiments 1 through 11 wherein $Q^1$ is a phenyl ring substituted at the 2-, 4- and 6-positions with substituents independently selected from $R^{3a}$ and $R^{3b}$; or a phenyl ring substituted at the 2- and 4-positions with substituents independently selected from $R^{3a}$ and $R^{3b}$; or a phenyl ring substituted at the 2- and 6-positions with substituents independently selected from $R^{3a}$ and $R^{3b}$ (relative to the connection of the $Q^1$ ring to the remainder of Formula 1).

Embodiment 13

A compound of Formula 1 or any one of Embodiments 1 through 12 wherein $Q^2$ is a phenyl, pyridinyl, pyrimidinyl, pyrazinyl or pyridazinyl ring, each ring optionally substituted with up to 3 substituents independently selected from $R^{3a}$ and $R^{3b}$.

Embodiment 14

A compound of Embodiment 13 wherein $Q^2$ is a phenyl ring optionally substituted with up to 3 substituents independently selected from $R^{3a}$ and $R^{3b}$.

Embodiment 15

A compound of Embodiment 14 wherein $Q^2$ is a phenyl ring optionally substituted with up to 2 substituents independently selected from $R^{3a}$ and $R^{3b}$.

Embodiment 16

A compound of Embodiment 14 wherein $Q^2$ is a phenyl ring substituted with 1 to 3 substituents independently selected from $R^{3a}$.

Embodiment 17

A compound of Embodiment 16 wherein $Q^2$ is a phenyl ring substituted with 3 substituents independently selected from $R^{3a}$.

Embodiment 18

A compound of Embodiment 17 wherein $Q^2$ is a phenyl ring substituted with 2 substituents independently selected from $R^{3a}$.

Embodiment 19

A compound of Formula 1 or any one of Embodiments 1 through 18 wherein $Q^2$ is a phenyl ring substituted with 1 to 3 substituents independently selected from $R^{3a}$ and $R^{3b}$.

Embodiment 20

A compound of Embodiment 19 wherein $Q^2$ is a phenyl ring substituted with 2 substituents independently selected from $R^{3a}$ and 1 substituent selected from $R^{3b}$.

Embodiment 21

A compound of Embodiment 20 wherein $Q^2$ is a phenyl ring substituted with 1 substituent selected from $R^{3a}$ and 1 substituent selected from $R^{3b}$.

Embodiment 22

A compound of Formula 1 or any one of Embodiments 1 through 21 wherein $Q^2$ is a phenyl ring substituted with at least 1 substituent selected from $R^{3a}$ which is attached at an ortho position (relative to the connection of the $Q^2$ ring to the remainder of Formula 1).

Embodiment 23

A compound of Formula 1 or any one of Embodiments 1 through 22 wherein $Q^2$ is a phenyl ring substituted with at least 1 substituent selected from $R^{3b}$ which is attached at the para position (relative to the connection of the $Q^2$ ring to the remainder of Formula 1).

Embodiment 24

A compound of Formula 1 or any one of Embodiments 1 through 23 wherein $Q^2$ is a phenyl ring substituted with at least 2 substituents independently selected from $R^{3a}$ which are attached at the 2- and 6-positions (relative to the connection of the $Q^2$ ring to the remainder of Formula 1).

Embodiment 24a

A compound of Formula 1 or any one of Embodiments 1 through 24 wherein $Q^2$ is a phenyl ring substituted with at least 2 substituents independently selected from $R^{3a}$ which are attached at the 2- and 4-positions (relative to the connection of the $Q^2$ ring to the remainder of Formula 1).

Embodiment 25

A compound of Formula 1 or any one of Embodiments 1 through 24a wherein $Q^2$ is a phenyl ring substituted with 2 substituents independently selected from $R^{3a}$ which are attached at the 2- and 6-positions; or a phenyl ring substituted with 2 substituents independently selected from $R^{3a}$ which are attached at the 2- and 4-positions (relative to the connection of the $Q^2$ ring to the remainder of Formula 1).

Embodiment 26

A compound of Formula 1 or any one of Embodiments 1 through 25 wherein $Q^2$ is a phenyl ring substituted with 2 substituents independently selected from $R^{3a}$ which are attached at the 2- and 4-positions (relative to the connection of the $Q^2$ ring to the remainder of Formula 1).

Embodiment 27

A compound of Formula 1 or any one of Embodiments 1 through 26 wherein $Q^2$ is a phenyl ring substituted at the 2-, 4- and 6-positions with substituents independently selected from $R^{3a}$ and $R^{3b}$; or a phenyl ring substituted at the 2- and 4-positions with substituents independently selected from $R^{3a}$ and $R^{3b}$; or a phenyl ring substituted at the 2- and 6-positions with substituents independently selected from $R^{3a}$ and $R^{3b}$.

Embodiment 28

A compound of Formula 1 or any one of Embodiments 1 through 27 wherein when each $Q^1$ and $Q^2$ is a phenyl ring, then one of the $Q^1$ and $Q^2$ rings is substituted with 2 or 3 substituents and the other of the $Q^1$ and $Q^2$ rings is substituted with 1 or 2 substituents.

Embodiment 29

A compound of Formula 1 or any one of Embodiments 1 through 28 wherein when each $Q^1$ and $Q^2$ is a phenyl ring, then $Q^1$ is substituted with 3 substituents and $Q^2$ is substituted with 2 substituents.

Embodiment 30

A compound of Formula 1 or any one of Embodiments 1 through 29 wherein X is O, S, $NR^4$ or $CR^{5a}OR^{5b}$.

Embodiment 31

A compound of Embodiment 30 wherein X is O, $NR^4$ or $CHOR^{5b}$.

Embodiment 32

A compound of Embodiment 31 wherein X is $NR^4$ or $CHOR^{5b}$.

Embodiment 33

A compound of Embodiment 32 wherein X is $CHOR^{5b}$.

Embodiment 34

A compound of Embodiment 33 wherein X is CHOH.

Embodiment 35

A compound of Embodiment 32 wherein X is $NR^4$.

Embodiment 36

A compound of Formula 1 or any one of Embodiments 1 through 35 wherein when $R^1$ is taken alone (i.e. not taken together with $R^{1a}$), then $R^1$ is H, cyano, halogen, $C_1$-$C_3$ alkyl, $C_1$-$C_3$ haloalkyl, $C_2$-$C_4$ alkenyl, $C_2$-$C_4$ alkynyl, cyclopropyl, $C_2$-$C_4$ alkoxyalkyl, $C_1$-$C_3$ alkoxy, $C_1$-$C_3$ haloalkoxy, —C(=O)$OR^6$ or —C(=O)$NR^7R^8$.

Embodiment 37

A compound of Embodiment 36 wherein $R^1$ is H, cyano, halogen, $C_1$-$C_3$ alkyl, $C_1$-$C_3$ haloalkyl, $C_2$-$C_4$ alkoxyalkyl, $C_1$-$C_3$ alkoxy or $C_1$-$C_3$ haloalkoxy.

Embodiment 38

A compound of Embodiment 37 wherein $R^1$ is H, cyano, halogen, $C_1$-$C_3$ alkyl, $C_1$-$C_3$ haloalkyl, $C_1$-$C_3$ alkoxy or $C_1$-$C_3$ haloalkoxy.

Embodiment 39

A compound of Embodiment 38 wherein $R^1$ is H, halogen or $C_1$-$C_3$ alkyl.

Embodiment 40

A compound of Embodiment 39 wherein $R^1$ is H or methyl.

Embodiment 41

A compound of Embodiment 40 wherein $R^1$ is H.

Embodiment 42

A compound of Formula 1 or any one of Embodiments 1 through 41 wherein $R^1$ is taken alone.

Embodiment 43

A compound of Formula 1 or any one of Embodiments 1 through 42 wherein $R^{1a}$ is H.

Embodiment 44

A compound of Formula 1 or any one of Embodiments 1 through 43 wherein $R^{1a}$ is taken alone.

Embodiment 45

A compound of Formula 1 or any one of Embodiments 1 through 44 wherein when $R^{1a}$ and $R^1$ are taken together with the carbon atom to which they are attached to form a ring, then said ring is cyclopropyl (i.e. unsubstituted).

Embodiment 46

A compound of Formula 1 or any one of Embodiments 1 through 45 wherein $R^{1a}$ and $R^1$ are taken together.

Embodiment 47

A compound of Formula 1 or any one of Embodiments 1 through 46 wherein $R^2$ is cyano, halogen, $C_1$-$C_2$ alkyl, halomethyl, cyanomethyl, hydroxymethyl, methoxy or methylthio; or cyclopropyl optionally substituted with up to 2 substituents independently selected from halogen and methyl.

Embodiment 48

A compound of Embodiment 47 wherein $R^2$ is Br, Cl, I or $C_1$-$C_2$ alkyl.

Embodiment 49

A compound of Embodiment 48 wherein $R^2$ is Br, Cl or methyl.

Embodiment 50

A compound of Embodiment 49 wherein $R^2$ is methyl.

Embodiment 51

A compound of Formula 1 or any one of Embodiments 1 through 50 wherein each $R^{3a}$ is independently amino, cyano, halogen, $C_1$-$C_3$ alkyl, $C_1$-$C_3$ haloalkyl, $C_2$-$C_4$ alkenyl, $C_3$-$C_4$ cycloalkyl, $C_4$-$C_6$ cycloalkylalkyl, $C_4$-$C_6$ alkylcycloalkyl, $C_1$-$C_3$ alkylthio, $C_1$-$C_3$ alkylsulfinyl, $C_1$-$C_3$ alkylsulfonyl, $C_1$-$C_3$ alkoxy, $C_1$-$C_3$ haloalkoxy, $C_3$-$C_6$ cycloalkoxy, $C_1$-$C_3$ alkylsulfonyloxy, $C_2$-$C_4$ alkylcarbonyloxy, $C_2$-$C_4$ alkylcarbonyl, $C_1$-$C_3$ alkylamino, $C_2$-$C_4$ dialkylamino, $C_2$-$C_4$ alkylcarbonylamino, —CH(=O), —NHCH(=O), —SF$_5$, —SC≡N or —U—V-T.

Embodiment 52

A compound of Embodiment 51 wherein each $R^{3a}$ is independently cyano, halogen, methyl, halomethyl, cyclopropyl, methylthio, methoxy, methylsulfonyloxy, methylcarbonyloxy, methylcarbonyl or —U—V-T.

Embodiment 53

A compound of Embodiment 52 wherein each $R^{3a}$ is independently cyano, halogen, methyl, halomethyl or methoxy.

Embodiment 54

A compound of Embodiment 53 wherein each $R^{3a}$ is independently cyano, halogen or methoxy.

Embodiment 55

A compound of Embodiment 54 wherein each $R^{3a}$ is independently cyano, Br, Cl, F or methoxy.

Embodiment 56

A compound of Embodiment 55 wherein each $R^{3a}$ is independently Br, Cl or F.

Embodiment 57

A compound of Formula 1 or any one of Embodiments 1 through 56 wherein each $R^{3b}$ is independently $C_2$-$C_4$ haloalkenyl, $C_5$-$C_8$ cycloalkylalkenyl, $C_5$-$C_8$ cycloalkylalkynyl, $C_4$-$C_6$ alkoxy, $C_4$-$C_6$ haloalkoxy, $C_2$-$C_6$ alkenyloxy, $C_2$-$C_6$ haloalkenyloxy, $C_3$-$C_6$ alkynyloxy, $C_3$-$C_6$ haloalkynyloxy, $C_4$-$C_8$ cycloalkylalkoxy, $C_4$-$C_6$ alkylsulfonyloxy, $C_4$-$C_6$ haloalkylsulfonyloxy, $C_3$-$C_9$ trialkylsilyl, $C_4$-$C_9$ trialkylsilylalkyl, $C_4$-$C_9$ trialkylsilylalkoxy, —C(=S)NR$^{9a}$R$^{9b}$, —CR$^{10a}$=NOR$^{10b}$, —ON=CR$^{11a}$R$^{11b}$ or -A(CR$^{12a}$R$^{12b}$)$_n$W.

Embodiment 58

A compound of Embodiment 57 wherein each $R^{3b}$ is independently $C_5$-$C_8$ cycloalkylalkenyl, $C_5$-$C_8$ cycloalkylalkynyl, $C_4$-$C_6$ alkoxy, $C_4$-$C_6$ haloalkoxy, $C_2$-$C_6$ alkenyloxy, $C_2$-$C_6$ haloalkenyloxy, $C_3$-$C_6$ alkynyloxy, $C_3$-$C_6$ haloalkynyloxy, $C_4$-$C_8$ cycloalkylalkoxy, $C_4$-$C_6$ alkylsulfonyloxy, $C_4$-$C_6$ haloalkylsulfonyloxy, $C_4$-$C_9$ trialkylsilylalkoxy, —C(=S)NR$^{9a}$R$^{9b}$, —CR$^{10a}$=NOR$^{10b}$, —ON=CR$^{11a}$R$^{11b}$ or -A(CR$^{12a}$R$^{12b}$)$_n$W.

Embodiment 59

A compound of Embodiment 58 wherein each $R^{3b}$ is independently $C_5$-$C_8$ cycloalkylalkynyl, $C_4$-$C_6$ alkoxy, $C_4$-$C_6$ haloalkoxy, $C_2$-$C_6$ alkenyloxy, $C_2$-$C_6$ haloalkenyloxy, $C_3$-$C_6$ alkynyloxy, $C_3$-$C_6$ haloalkynyloxy, $C_4$-$C_8$ cycloalkylalkoxy, $C_4$-$C_9$ trialkylsilylalkoxy, —C(=S)NR$^{9a}$R$^{9b}$, —CR$^{10a}$=NOR$^{10b}$, —ON=CR$^{11a}$R$^{11b}$ or -A(CR$^{12a}$R$^{12b}$)$_n$W.

Embodiment 60

A compound of Embodiment 59 wherein each $R^{3b}$ is independently $C_5$-$C_8$ cycloalkylalkynyl, $C_4$-$C_6$ alkoxy, $C_4$-$C_6$ haloalkoxy, $C_2$-$C_6$ alkenyloxy, $C_2$-$C_6$ haloalkenyloxy, $C_3$-$C_6$ alkynyloxy, $C_4$-$C_8$ cycloalkylalkoxy, $C_4$-$C_9$ trialkylsilylalkoxy, —C(=S)NR$^{9a}$R$^{9b}$, —CR$^{10a}$=NOR$^{10b}$, —ON=CR$^{11a}$R$^{11b}$ or -A(CR$^{12a}$R$^{12b}$)$_n$W.

Embodiment 61

A compound of Embodiment 60 wherein each R$^{3b}$ is independently $C_5$-$C_8$ cycloalkylalkynyl, $C_4$-$C_6$ alkoxy, $C_4$-$C_6$ haloalkoxy, $C_2$-$C_6$ alkenyloxy, $C_2$-$C_6$ haloalkenyloxy, $C_3$-$C_6$ alkynyloxy, $C_4$-$C_8$ cycloalkylalkoxy, $C_4$-$C_9$ trialkylsilylalkoxy, —CR$^{10a}$=NOR$^9$, —ON=CR$^{11a}$R$^{11b}$ or -A(CR$^{12a}$R$^{12b}$)$_n$W.

Embodiment 62

A compound of Embodiment 61 wherein each R$^{3b}$ is independently $C_5$-$C_8$ cycloalkylalkynyl, $C_4$-$C_6$ alkoxy, $C_4$-$C_6$ haloalkoxy, $C_2$-$C_6$ alkenyloxy, $C_2$-$C_6$ haloalkenyloxy, $C_3$-$C_6$ alkynyloxy, $C_4$-$C_8$ cycloalkylalkoxy, —CR$^{10a}$=NOR$^9$ or -A(CR$^{12a}$R$^{12b}$)$_n$W.

Embodiment 63

A compound of Embodiment 62 wherein each R$^{3b}$ is independently $C_2$-$C_6$ alkenyloxy, $C_2$-$C_6$ haloalkenyloxy, $C_3$-$C_6$ alkynyloxy or -A(CR$^{12a}$R$^{12b}$)$_n$W.

Embodiment 64

A compound of Embodiment 63 wherein each R$^{3b}$ is -A(CR$^{12a}$R$^{12b}$)$_n$W.

Embodiment 65

A compound of Formula 1 or any one of Embodiments 1 through 64 wherein each A is O or a direct bond.

Embodiment 66

A compound of Formula 1 or any one of Embodiments 1 through 65 wherein each A is O.

Embodiment 66a

A compound of Formula 1 or any one of Embodiments 1 through 65 wherein each A is a direct bond.

Embodiment 67

A compound of Formula 1 or any one of Embodiments 1 through 66a wherein each W is independently a 3- to 7-membered heterocyclic ring containing ring members selected from carbon atoms and 1 to 2 heteroatoms independently selected from up to 2 O, up to 2 S and up to 2 N atoms, wherein up to 1 carbon atom ring member is C(=O), the ring optionally substituted with up to 3 substituents independently selected from R$^{13}$ on carbon atom ring members and R$^{14}$ on nitrogen atom ring members.

Embodiment 68

A compound of Embodiment 67 wherein each W is independently a 3- to 6-membered heterocyclic ring containing ring members selected from carbon atoms and 1 to 2 heteroatoms independently selected from up to 2 O, up to 2 S and up to 2 N atoms, the ring optionally substituted with up to 3 substituents independently selected from R$^{13}$ on carbon atom ring members and R$^{14}$ on nitrogen atom ring members.

Embodiment 69

A compound of Embodiment 68 wherein each W is independently a 3- to 5-membered heterocyclic ring containing ring members selected from carbon atoms and 1 to 2 heteroatoms independently selected from up to 2 O and up to 2 N atoms, the ring optionally substituted with up to 2 substituents independently selected from R$^{13}$ on carbon atom ring members and R$^{14}$ on nitrogen atom ring members.

Embodiment 70

A compound of Embodiment 69 wherein each W is independently a 3- to 5-membered heterocyclic ring containing ring members selected from carbon atoms and 1 to 2 heteroatoms independently selected from up to 2 O and up to 2 N atoms, the ring optionally substituted with up to 2 substituents independently selected from R$^{13}$ on carbon atom ring members.

Embodiment 70a

A compound of Embodiment 70 wherein each W is independently a 5-membered heterocyclic ring containing ring members selected from carbon atoms and 1 to 2 heteroatoms independently selected from up to 2 O and up to 2 N atoms, the ring optionally substituted with up to 2 substituents independently selected from R$^{13}$ on carbon atom ring members.

Embodiment 70b

A compound of Embodiment 70 wherein each W is independently a 3- to 5-membered heterocyclic ring containing ring members selected from carbon atoms and 1 to 2 heteroatoms independently selected from up to 2 O and up to 2 N atoms.

Embodiment 71

A compound of Formula 1 or any one of Embodiments 1 through 70b wherein R$^4$ is H, amino, $C_2$-$C_3$ alkenyl, $C_3$-$C_4$ alkynyl, cyclopropyl, —CH(=O), —S(=O)$_2$OM, —S(=O)$_m$R$^{15}$, —(C=Z)R$^{16}$ or OR$^{17}$; or $C_1$-$C_3$ alkyl or $C_1$-$C_3$ haloalkyl, each optionally substituted with up to 2 substituents independently selected from R$^{18}$.

Embodiment 72

A compound of Embodiment 71 wherein R$^4$ is H, cyclopropyl, —CH(=O), —S(=O)$_2$OM, —S(=O)$_m$R$^{15}$, —(C=Z)R$^{16}$, OR$^{17}$, $C_1$-$C_3$ alkyl or $C_1$-$C_3$ haloalkyl.

Embodiment 73

A compound of Embodiment 72 wherein R$^4$ is H, —CH(=O), —S(=O)$_m$R$^{15}$, —(C=Z)R$^{16}$, OR$^{17}$, $C_1$-$C_3$ alkyl or $C_1$-$C_3$ haloalkyl.

Embodiment 74

A compound of Embodiment 73 wherein R$^4$ is H, —CH(=O), OR$^{17}$, $C_1$-$C_3$ alkyl or $C_1$-$C_3$ haloalkyl.

Embodiment 75

A compound of Embodiment 74 wherein $R^4$ is H, —CH(=O) or methoxy.

Embodiment 76

A compound of Embodiment 75 wherein $R^4$ is H.

Embodiment 77

A compound of Formula 1 or any one of Embodiments 1 through 76 wherein $R^{5a}$ is H or methyl.

Embodiment 78

A compound of Embodiment 77 wherein $R^{5a}$ is H.

Embodiment 79

A compound of Formula 1 or any one of Embodiments 1 through 78 wherein $R^{5b}$ is H, —CH(=O), $C_1$-$C_3$ alkyl, $C_1$-$C_2$ haloalkyl, $C_2$-$C_4$ cyanoalkyl, $C_2$-$C_3$ alkoxyalkyl, $C_2$-$C_4$ alkylcarbonyl, $C_2$-$C_4$ alkoxycarbonyl, $C_2$-$C_4$ (alkylthio)carbonyl or $C_2$-$C_4$ alkoxy(thiocarbonyl).

Embodiment 80

A compound of Embodiment 79 wherein $R^{5b}$ is H, —CH(=O), $C_1$-$C_3$ alkyl, $C_1$-$C_2$ haloalkyl, $C_2$-$C_4$ cyanoalkyl, $C_2$-$C_3$ alkoxyalkyl, $C_2$-$C_4$ alkylcarbonyl or $C_2$-$C_4$ alkoxycarbonyl.

Embodiment 81

A compound of Embodiment 80 wherein $R^{5b}$ is H, —CH(=O), methyl, halomethyl, cyanomethyl, methylcarbonyl or methoxycarbonyl.

Embodiment 82

A compound of Embodiment 81 wherein $R^{5b}$ is H.

Embodiment 83

A compound of Formula 1 or any one of Embodiments 1 through 82 wherein $R^6$ is H or $C_1$-$C_6$ alkyl.

Embodiment 84

A compound of Embodiment 83 wherein $R^6$ is H or $C_1$-$C_2$ alkyl.

Embodiment 85

A compound of Embodiment 84 wherein $R^6$ is H or methyl.

Embodiment 86

A compound of Embodiment 85 wherein $R^6$ is H.

Embodiment 87

A compound of Formula 1 or any one of Embodiments 1 through 86 wherein when $R^7$ is taken alone (i.e. not taken together with $R^8$ to form a ring), then $R^7$ is H or $C_1$-$C_6$ alkyl.

Embodiment 88

A compound of Embodiment 87 wherein $R^7$ is H.

Embodiment 89

A compound of Formula 1 or any one of Embodiments 1 through 88 wherein $R^7$ is taken alone.

Embodiment 90

A compound of Formula 1 or any one of Embodiments 1 through 89 wherein when $R^8$ is taken alone (i.e. not taken together with $R^7$ to form a ring), then $R^8$ is H, $C_1$-$C_6$ alkyl, $C_1$-$C_6$ haloalkyl or $C_4$-$C_8$ alkylcycloalkyl.

Embodiment 91

A compound of Embodiment 90 wherein $R^8$ is H or $C_1$-$C_6$ alkyl.

Embodiment 92

A compound of Embodiment 91 wherein $R^8$ is H.

Embodiment 93

A compound of Formula 1 or any one of Embodiments 1 through 92 wherein $R^8$ is taken alone.

Embodiment 94

A compound of Formula 1 or any one Embodiments 1 through 93 wherein when $R^7$ and $R^8$ are taken together with the nitrogen atom to which they are attached to form a 4- to 7-membered nonaromatic heterocyclic ring, then said ring contains ring members, in addition to the connecting nitrogen atom, selected from carbon atoms and up to 1 ring member selected from O and $NR^{19}$.

Embodiment 95

A compound of Embodiment 94 wherein $R^7$ and $R^8$ are taken together with the nitrogen atom to which they are attached to form a 5- to 6-membered nonaromatic heterocyclic, containing ring members, in addition to the connecting nitrogen atom, selected from carbon atoms and up to 1 ring member selected from O and $NR^{19}$.

Embodiment 96

A compound of Embodiment 95 wherein $R^7$ and $R^8$ are taken together with the nitrogen atom to which they are connected to form a piperidinyl, piperazinyl or morpholinyl ring.

Embodiment 97

A compound of Formula 1 or any one of Embodiments 1 through 96 wherein each $R^{9a}$ and $R^{9b}$ is independently H or methyl.

Embodiment 98

A compound of Embodiment 97 wherein each $R^{9a}$ and $R^{9b}$ is H.

Embodiment 99

A compound of Formula 1 or any one of Embodiments 1 through 98 wherein each $R^{10a}$ is independently H, methyl or halomethyl.

Embodiment 100

A compound of Embodiment 99 wherein each $R^{10a}$ is H.

Embodiment 101

A compound of Formula 1 or any one of Embodiments 1 through 100 wherein each $R^{10b}$ and $R^{10c}$ is independently H, $C_1$-$C_3$ alkyl, $C_1$-$C_3$ haloalkyl, $C_3$-$C_4$ cycloalkyl or $C_3$-$C_4$ halocycloalkyl.

Embodiment 102

A compound of Embodiment 101 wherein each $R^{10b}$ and $R^{10c}$ is independently H, methyl, halomethyl or cyclopropyl.

Embodiment 103

A compound of Formula 1 or any one of Embodiments 1 through 102 wherein each $R^{11a}$ and $R^{11b}$ is independently H, methyl or halomethyl.

Embodiment 104

A compound of Embodiment 103 wherein each $R^{11a}$ and $R^{11b}$ is H.

Embodiment 105

A compound of Formula 1 or any one of Embodiments 1 through 104 wherein each $R^{12a}$ is independently H, cyano, halogen or methyl.

Embodiment 106

A compound of Embodiment 105 wherein each $R^{12a}$ is independently H or methyl.

Embodiment 107

A compound of Embodiment 106 wherein each $R^{12a}$ is H.

Embodiment 108

A compound of Formula 1 or any one of Embodiments 1 through 107 wherein each $R^{12b}$ is independently H or methyl.

Embodiment 109

A compound of Embodiment 108 wherein each $R^{12b}$ is H.

Embodiment 110

A compound of Formula 1 or any one of Embodiments 1 through 109 wherein each $R^{13}$ is independently cyano, halogen, methyl, halomethyl, methoxy or halomethoxy.

Embodiment 111

A compound of Embodiment 110 wherein each $R^{13}$ is independently halogen, methyl, halomethyl or methoxy.

Embodiment 112

A compound of Embodiment 111 wherein each $R^{13}$ is methyl.

Embodiment 113

A compound of Formula 1 or any one of Embodiments 1 through 112 wherein each $R^{14}$ is independently methyl or methoxy.

Embodiment 114

A compound of Formula 1 or any one of Embodiments 1 through 113 wherein $R^{15}$ is methyl or halomethyl.

Embodiment 115

A compound of Formula 1 or any one of Embodiments 1 through 114 wherein $R^{16}$ is $C_1$-$C_6$ alkyl, $C_1$-$C_6$ alkoxy or $C_1$-$C_6$ alkylthio.

Embodiment 116

A compound of Embodiment 115 wherein $R^{16}$ is methyl, ethyl, methoxy, ethoxy, methylthio or ethylthio.

Embodiment 117

A compound of Embodiment 116 wherein $R^{16}$ is methyl, methoxy or methylthio.

Embodiment 118

A compound of Formula 1 or any one of Embodiments 1 through 117 wherein $R^{17}$ is H, —CH(=O), cyclopropyl, —S(=O)$_2$OM or —(C=Z)R$^{20}$; or $C_1$-$C_3$ alkyl or $C_1$-$C_3$ haloalkyl, each optionally substituted with up to 2 substituents independently selected from $R^{21}$.

Embodiment 119

A compound of Formula 1 or any one of Embodiments 1 through 118 wherein each $R^{18}$ and $R^{21}$ is independently cyano, $C_3$-$C_6$ cycloalkyl or $C_1$-$C_3$ alkoxy.

Embodiment 120

A compound of Embodiment 119 wherein each $R^{18}$ and $R^{21}$ is independently cyano, cyclopropyl or methoxy.

Embodiment 121

A compound of Embodiment 120 wherein each $R^{18}$ and $R^{21}$ is independently cyclopropyl or methoxy.

Embodiment 122

A compound of Formula 1 or any one of Embodiments 1 through 121 wherein $R^{19}$ is H or CH$_3$.

Embodiment 123

A compound of Embodiment 122 wherein $R^{19}$ is CH$_3$.

Embodiment 124

A compound of Formula 1 or any one of Embodiments 1 through 123 wherein $R^{20}$ is $C_1$-$C_6$ alkyl, $C_1$-$C_6$ alkoxy or $C_1$-$C_6$ alkylthio.

Embodiment 125

A compound of Embodiment 124 wherein $R^{20}$ is methyl, ethyl, methoxy, ethoxy, methylthio or ethylthio.

Embodiment 126

A compound of Embodiment 125 wherein $R^{20}$ is methyl, methoxy or methylthio.

Embodiment 127

A compound of Formula 1 or any one of Embodiments 1 through 126 wherein each U is independently O or $NR^{22}$.

Embodiment 128

A compound of Embodiment 127 wherein each U is independently O or NH.

Embodiment 129

A compound of Formula 1 or any one of Embodiments 1 through 128 wherein each V is $C_2$-$C_4$ alkylene.

Embodiment 130

A compound of Formula 1 or any one of Embodiments 1 through 129 wherein each T is independently $NR^{23a}R^{23b}$ or $OR^{24}$.

Embodiment 131

A compound of Formula 1 or any one of Embodiments 1 through 130 wherein each $R^{23a}$ and $R^{23b}$ is independently H, $C_1$-$C_6$ alkyl or $C_1$-$C_6$ haloalkyl.

Embodiment 132

A compound of Embodiment 131 wherein each $R^{23a}$ and $R^{23b}$ is independently H, methyl or halomethyl.

Embodiment 133

A compound of Formula 1 or any one of Embodiments 1 through 132 wherein each $R^{24}$ is independently H, $C_1$-$C_6$ alkyl or $C_1$-$C_6$ haloalkyl.

Embodiment 134

A compound of Embodiment 133 wherein each $R^{24}$ is methyl.

Embodiment 135

A compound of Formula 1 or any one of Embodiments 1 through 134 wherein Z is O.

Embodiment 136

A compound of Formula 1 or any one of Embodiments 1 through 135 wherein M is K or Na.

Embodiment 137

A compound of Formula 1 or any one of Embodiments 1 through 136 wherein m is 0.

Embodiment 138

A compound of Formula 1 or any one of Embodiments 1 through 137 wherein each n is 3.

Embodiment 139

A compound of Formula 1 or any one of Embodiments 1 through 137 wherein each n is independently 0, 1 or 2.

Embodiment 140

A compound of Formula 1 or any one of Embodiments 1 through 137 wherein each n is independently 1, 2 or 3.

Embodiment 141

A compound of Embodiment 139 wherein each n is independently 0 or 1.

Embodiment 142

A compound of Embodiments 139 through 141 wherein each n is 1.

Embodiment 143

A compound of Embodiments 139 or 141 wherein each n is 0.

Embodiments of this invention, including Embodiments 1-143 above as well as any other embodiments described herein, can be combined in any manner, and the descriptions of variables in the embodiments pertain not only to the compounds of Formula 1 but also to the starting compounds and intermediate compounds useful for preparing the compounds of Formula 1 unless further defined in the Embodiments. In addition, embodiments of this invention, including Embodiments 1-143 above as well as any other embodiments described herein, and any combination thereof, pertain to the compositions and methods of the present invention. Combinations of Embodiments 1-143 are illustrated by:

Embodiment A

A compound of Formula 1 wherein
$Q^1$ is a phenyl, pyridinyl, pyrimidinyl, pyrazinyl or pyridazinyl ring, each ring optionally substituted with up to 3 substituents independently selected from $R^{3a}$ and $R^{3b}$;
$Q^2$ is a phenyl, pyridinyl, pyrimidinyl, pyrazinyl or pyridazinyl ring, each ring optionally substituted with up to 3 substituents independently selected from $R^{3a}$ and $R^{3b}$;
X is O, $NR^4$ or $CHOR^{5b}$;
$R^1$ is H, cyano, halogen, $C_1$-$C_3$ alkyl, $C_1$-$C_3$ haloalkyl, $C_2$-$C_4$ alkenyl, $C_2$-$C_4$ alkynyl, cyclopropyl, $C_2$-$C_4$ alkoxyalkyl, $C_1$-$C_3$ alkoxy, $C_1$-$C_3$ haloalkoxy, —C(=O)$OR^6$ or —C(=O)$NR^7R^8$;
$R^{1a}$ is H;
$R^2$ is Br, Cl, I or $C_1$-$C_2$ alkyl;

each $R^{3a}$ is independently amino, cyano, halogen, $C_1$-$C_3$ alkyl, $C_1$-$C_3$ haloalkyl, $C_2$-$C_4$ alkenyl, $C_3$-$C_4$ cycloalkyl, $C_4$-$C_6$ cycloalkylalkyl, $C_4$-$C_6$ alkylcycloalkyl, $C_1$-$C_3$ alkylthio, $C_1$-$C_3$ alkylsulfinyl, $C_1$-$C_3$ alkylsulfonyl, $C_1$-$C_3$ alkoxy, $C_1$-$C_3$ haloalkoxy, $C_3$-$C_6$ cycloalkoxy, $C_1$-$C_3$ alkylsulfonyloxy, $C_2$-$C_4$ alkylcarbonyloxy, $C_2$-$C_4$ alkylcarbonyl, $C_1$-$C_3$ alkylamino, $C_2$-$C_4$ dialkylamino, $C_2$-$C_4$ alkylcarbonylamino, —CH(=O), —NHCH(=O), —SF$_5$, —SC≡N or —U—V-T;

each $R^{3b}$ is independently $C_2$-$C_4$ haloalkenyl, $C_5$-$C_8$ cycloalkylalkenyl, $C_5$-$C_8$ cycloalkylalkynyl, $C_4$-$C_6$ alkoxy, $C_4$-$C_6$ haloalkoxy, $C_2$-$C_6$ alkenyloxy, $C_2$-$C_6$ haloalkenyloxy, $C_3$-$C_6$ alkynyloxy, $C_3$-$C_6$ haloalkynyloxy, $C_4$-$C_8$ cycloalkylalkoxy, $C_4$-$C_6$ alkylsulfonyloxy, $C_4$-$C_6$ haloalkylsulfonyloxy, $C_3$-$C_9$ trialkylsilyl, $C_4$-$C_9$ trialkylsilylalkyl, $C_4$-$C_9$ trialkylsilylalkoxy, —C(=S)NR$^{9a}$R$^{9b}$, —CR$^{10a}$=NOR$^{10b}$, —ON=CR$^{11a}$R$^{11b}$ or -A(CR$^{12a}$R$^{12b}$)$_n$W;

each W is independently a 3- to 7-membered heterocyclic ring containing ring members selected from carbon atoms and 1 to 2 heteroatoms independently selected from up to 2 O, up to 2 S and up to 2 N atoms, wherein up to 1 carbon atom ring member is C(=O), the ring optionally substituted with up to 3 substituents independently selected from $R^{13}$ on carbon atom ring members and $R^{14}$ on nitrogen atom ring members;

$R^4$ is H, cyclopropyl, —CH(=O), —S(=O)$_2$OM, —S(=O)$_m$R$^{15}$, —(C=Z)R$^{16}$, OR$^{17}$, $C_1$-$C_3$ alkyl or $C_1$-$C_3$ haloalkyl;

$R^{5b}$ is H, —CH(=O), $C_1$-$C_3$ alkyl, $C_1$-$C_2$ haloalkyl, $C_2$-$C_4$ cyanoalkyl, $C_2$-$C_3$ alkoxyalkyl, $C_2$-$C_4$ alkylcarbonyl or $C_2$-$C_4$ alkoxycarbonyl;

$R^6$ is H or methyl;

$R^7$ is H or $C_1$-$C_6$ alkyl;

$R^8$ is H, $C_1$-$C_6$ alkyl, $C_1$-$C_6$ haloalkyl or $C_4$-$C_8$ alkylcycloalkyl;

each $R^{9a}$ and $R^{9b}$ is independently H or methyl;

each $R^{10a}$ is independently H, methyl or halomethyl;

each $R^{10b}$ is independently H, $C_1$-$C_3$ alkyl, $C_1$-$C_3$ haloalkyl, $C_3$-$C_4$ cycloalkyl or $C_3$-$C_4$ halocycloalkyl;

each $R^{11a}$ and $R^{11b}$ is independently H, methyl or halomethyl;

each $R^{12a}$ is independently H, cyano, halogen or methyl;

each $R^{12b}$ is independently H or methyl;

each $R^{13}$ is independently halogen, methyl, halomethyl or methoxy;

each $R^{14}$ is independently methyl or methoxy;

$R^{15}$ is methyl or halomethyl;

$R^{16}$ is methyl, ethyl, methoxy, ethoxy, methylthio or ethylthio;

$R^{17}$ is H, —CH(=O), cyclopropyl, —S(=O)$_2$OM or —(C=Z)R$^{20}$; or $C_1$-$C_3$ alkyl or $C_1$-$C_3$ haloalkyl, each optionally substituted with up to 2 substituents independently selected from $R^{21}$;

$R^{20}$ is methyl, methoxy or methylthio;

each U is independently O or NR$^{22}$;

each V is independently $C_2$-$C_4$ alkylene;

each T is independently NR$^{23a}$R$^{23b}$ or OR$^{24}$;

each $R^{23a}$ and $R^{23b}$ is independently H, $C_1$-$C_6$ alkyl or $C_1$-$C_6$ haloalkyl;

each $R^{24}$ is independently H, $C_1$-$C_6$ alkyl or $C_1$-$C_6$ haloalkyl; and Z is O.

Embodiment B

A compound of Embodiment A wherein $Q^1$ is a phenyl ring optionally substituted with up to 3 substituents independently selected from $R^{3a}$ and from $R^{3b}$;

$Q^2$ is a phenyl ring optionally substituted with up to 3 substituents independently selected from $R^{3a}$ and $R^{3b}$;

$R^1$ is H, cyano, halogen, $C_1$-$C_3$ alkyl, $C_1$-$C_3$ haloalkyl, $C_2$-$C_4$ alkoxyalkyl, $C_1$-$C_3$ alkoxy or $C_1$-$C_3$ haloalkoxy;

each $R^{3a}$ is independently cyano, halogen, methyl, halomethyl, cyclopropyl, methylthio, methoxy, methylsulfonyloxy, methylcarbonyloxy, methylcarbonyl or —U—V-T;

each $R^{3b}$ is independently $C_5$-$C_8$ cycloalkylalkenyl, $C_5$-$C_8$ cycloalkylalkynyl, $C_4$-$C_6$ alkoxy, $C_4$-$C_6$ haloalkoxy, $C_2$-$C_6$ alkenyloxy, $C_2$-$C_6$ haloalkenyloxy, $C_3$-$C_6$ alkynyloxy, $C_3$-$C_6$ haloalkynyloxy, $C_4$-$C_8$ cycloalkylalkoxy, $C_4$-$C_6$ alkylsulfonyloxy, $C_4$-$C_6$ haloalkylsulfonyloxy, $C_4$-$C_9$ trialkylsilylalkoxy, —C(=S)NR$^{9a}$R$^{9b}$, —CR$^{10a}$=NOR$^{10b}$, —ON=CR$^{11a}$R$^{11b}$ or -A(CR$^{12a}$R$^{12b}$)$_n$W;

each W is independently a 3- to 5-membered heterocyclic ring containing ring members selected from carbon atoms and 1 to 2 heteroatoms independently selected from up to 2 O and up to 2 N atoms, the ring optionally substituted with up to 2 substituents independently selected from $R^{13}$ on carbon atom ring members and $R^{14}$ on nitrogen atom ring members;

$R^4$ is H, —CH(=O) or methoxy;

$R^{5b}$ is H, —CH(=O), methyl, halomethyl, cyanomethyl, methylcarbonyl or methoxycarbonyl;

each $R^{12a}$ is independently H or methyl;

each $R^{12b}$ is H; and each U is independently O or NH.

Embodiment C

A compound of Embodiment B wherein

X is NR$^4$ or CHOR$^{5b}$;

$R^1$ is H, halogen or $C_1$-$C_3$ alkyl;

$R^2$ is Br, Cl or methyl;

each $R^{3a}$ is independently cyano, halogen or methoxy;

each $R^{3b}$ is independently $C_5$-$C_8$ cycloalkylalkynyl, $C_4$-$C_6$ alkoxy, $C_4$-$C_6$ haloalkoxy, $C_2$-$C_6$ alkenyloxy, $C_2$-$C_6$ haloalkenyloxy, $C_3$-$C_6$ alkynyloxy, $C_4$-$C_8$ cycloalkylalkoxy, $C_4$-$C_9$ trialkylsilylalkoxy, —CR$^{10a}$=NOR$^9$, —ON=CR$^{11a}$R$^{11b}$ or -A(CR$^{12a}$R$^{12b}$)$_n$W;

$R^4$ is H;

$R^{5b}$ is H;

each $R^{10a}$ is H;

each $R^{10b}$ is independently H, methyl, halomethyl or cyclopropyl; and each $R^{12a}$ is H.

Embodiment D

A compound of Embodiment C wherein $Q^1$ is a phenyl ring optionally substituted with up to 2 substituents independently selected from $R^{3a}$ and substituted with 1 substituent selected from $R^{3b}$;

$Q^2$ is a phenyl ring substituted with 1 to 3 substituents independently selected from $R^{3a}$;

$R^1$ is H;

$R^2$ is methyl; and each $R^{3a}$ is independently Br, Cl or F.

Embodiment E

A compound of Formula 1 wherein
$Q^1$ is a phenyl ring substituted at the 2-, 4- and 6-positions with substituents independently selected from $R^{3a}$ and $R^{3b}$; or a phenyl ring substituted at the 2- and 4-positions with substituents independently selected from $R^{3a}$ and $R^{3b}$; or a phenyl ring substituted at the 2- and 6-positions with substituents independently selected from $R^{3a}$ and $R^{3b}$.
$Q^2$ is a phenyl ring substituted at the 2-, 4- and 6-positions with substituents independently selected from $R^{3a}$ and $R^{3b}$; or a phenyl ring substituted at the 2- and 4-positions with substituents independently selected from $R^{3a}$ and $R^{3b}$; or a phenyl ring substituted at the 2- and 6-positions with substituents independently selected from $R^{3a}$ and $R^{3b}$.
X is $NR^4$ or $CHOR^{5b}$;
$R^1$ is H or methyl;
$R^{1a}$ is H;
$R^2$ is Br, Cl or methyl;
each $R^{3a}$ is independently cyano, halogen or methoxy;
each $R^{3b}$ is independently $C_5$-$C_8$ cycloalkylalkynyl, $C_4$-$C_6$ alkoxy, $C_4$-$C_6$ haloalkoxy, $C_2$-$C_6$ alkenyloxy, $C_2$-$C_6$ haloalkenyloxy, $C_3$-$C_6$ alkynyloxy, $C_4$-$C_8$ cycloalkylalkoxy, $C_4$-$C_9$ trialkylsilylalkoxy, —C(=S)$NR^{9a}R^{9b}$, —$CR^{10a}$=$NOR^{10b}$, —ON=$CR^{11a}R^{11b}$ or -A$(CR^{12a}R^{12b})_n$W;
each W is independently a 3- to 5-membered heterocyclic ring containing ring members selected from carbon atoms and 1 to 2 heteroatoms independently selected from up to 2 O and up to 2 N atoms, the ring optionally substituted with up to 2 substituents independently selected from $R^{13}$ on carbon atom ring members;
$R^4$ is H;
$R^{5b}$ is H;
each $R^{9a}$ and $R^{9b}$ is independently H or methyl;
each $R^{10a}$ is independently H, methyl or halomethyl;
each $R^{10b}$ is independently H, $C_1$-$C_3$ alkyl, $C_1$-$C_3$ haloalkyl, $C_3$-$C_4$ cycloalkyl or $C_3$-$C_4$ halocycloalkyl;
each $R^{11a}$ and $R^{11b}$ is independently H, methyl or halomethyl;
each $R^{12a}$ is independently H, cyano, halogen or methyl;
each $R^{12b}$ is independently H or methyl; and
each $R^{13}$ is independently halogen, methyl, halomethyl or methoxy.

Embodiment E

A compound of Embodiment E wherein
$Q^1$ is a phenyl ring substituted with 2 substituents independently selected from $R^{3a}$ and 1 substituent selected from $R^{3b}$;
$Q^2$ is a phenyl ring substituted with 1 to 3 substituents independently selected from $R^{3a}$;
X is $CHOR^{5b}$;
$R^1$ is H;
$R^2$ is methyl;
each $R^{3a}$ is independently Br, Cl or F;
$R^{3b}$ is $C_5$-$C_8$ cycloalkylalkynyl, $C_4$-$C_6$ alkoxy, $C_4$-$C_6$ haloalkoxy, $C_2$-$C_6$ alkenyloxy, $C_2$-$C_6$ haloalkenyloxy, $C_3$-$C_6$ alkynyloxy, $C_4$-$C_8$ cycloalkylalkoxy, $C_4$-$C_9$ trialkylsilylalkoxy, —$CR^{10a}$=$NOR^9$, —ON=$CR^{11a}R^{11b}$ or -A$(CR^{12a}R^{12b})_n$W;

W is a 3- to 5-membered heterocyclic ring containing ring members selected from carbon atoms and 1 to 2 heteroatoms independently selected from up to 2 O and up to 2 N atoms;
$R^{12a}$ is H;
$R^{12b}$ is H; and
n is 0, 1 or 2.

Embodiment F

A compound of Embodiment E wherein
$Q^1$ is a phenyl ring substituted with 2 substituents independently selected from $R^{3a}$ which are attached at the 2- and 6-positions and 1 substituent selected from $R^{3b}$ which is attached at the 4-position;
$Q^2$ is a phenyl ring substituted with 2 substituents independently selected from $R^{3a}$ which are attached at the 2- and 6-positions; or a phenyl ring substituted with 2 substituents independently selected from $R^{3a}$ which
$R^{3b}$ is $C_5$-$C_8$ cycloalkylalkynyl, $C_4$-$C_6$ alkoxy, $C_4$-$C_6$ haloalkoxy, $C_2$-$C_6$ alkenyloxy, $C_2$-$C_6$ haloalkenyloxy, $C_3$-$C_6$ alkynyloxy, $C_4$-$C_8$ cycloalkylalkoxy, —$CR^{10a}$=$NOR^9$ or -A$(CR^{12a}R^{12b})_n$W.

Specific embodiments include compounds of Formula 1 selected from the group consisting of:
α-(2-chloro-4-fluorophenyl)-5-[2,6-difluoro-4-(1H-pyrazol-1-yl)phenyl]-1,3-dimethyl-1H-pyrazole-4-methanol;
α-(2-chloro-4-fluorophenyl)-5-[4-(2-cyclopropylethynyl)-2,6-difluorophenyl]-1,3-dimethyl-1H-pyrazole-4-methanol;
α-(2-chloro-4-fluorophenyl)-5-[4-(cyclopropylmethoxy)-2,6-difluorophenyl]-1,3-dimethyl-1H-pyrazole-4-methanol.

One or more of the following methods and variations as described in Schemes 1-22 can be used to prepare the compounds of Formula 1. The definitions of $Q^1$, $Q^2$, X, $R^1$, $R^{1a}$, $R^2$, $R^{3a}$, $R^{3b}$, $R^4$ and $R^{5a}$ in the compounds of Formulae 1-35 below are as defined above in the Summary of the Invention unless otherwise noted. Formulae 1a-1k, 1m and 1n are various subsets of Formula 1. Substituents for each subset formula are as defined for its parent formula unless otherwise noted.

Compounds of Formula 1 can be prepared as shown in Scheme 1. In this method a compound of Formula 2 is first treated with an organometallic agent of Formula 3 such as an alkyl lithium base (e.g., n-butyllithium, s-butyllithium or lithium diisopropylamide) or a Grignard reagent in a solvent such as toluene, diethyl ether, tetrahydrofuran or dimethoxymethane at temperatures ranging from about −78° C. to ambient temperature. Anions of Formula 2a are then contacted with an electrophile of Formula 4, 5 or 6. The use and choice of an appropriate electrophile will depend on the desired compound of Formula 1 and will be apparent to one skilled in chemical synthesis. For example, chlorosulfides of formula $Q^2$SCl or disulfies formula of $Q^2$S—S-$Q^2$ (i.e. Formula 4) provide compounds of Formula 1a (i.e. Formula 1 wherein X is S), aldehydes of the formula $Q^2$CHO (i.e. Formula 5) provide compounds of Formula 1b (i.e. Formula 1 wherein X is CH(OH)) and nitrosobenzenes of formula $Q^2$-N=O (i.e. Formula 6) provide compounds of Formula 1c (i.e. Formula 1 wherein X is N(OH)). There are a wide-variety of general methods described in the synthetic literature for metalation/alkylation reactions which can be readily adapted to prepare compounds of the present invention; see, for example *Inorganic Chemistry* 2012, 51(17), 9385-9394 and PCT Publication WO 2010/030922 A1 (Example 4, Step D, Example 6 and Example 9, Step E).

Scheme 1

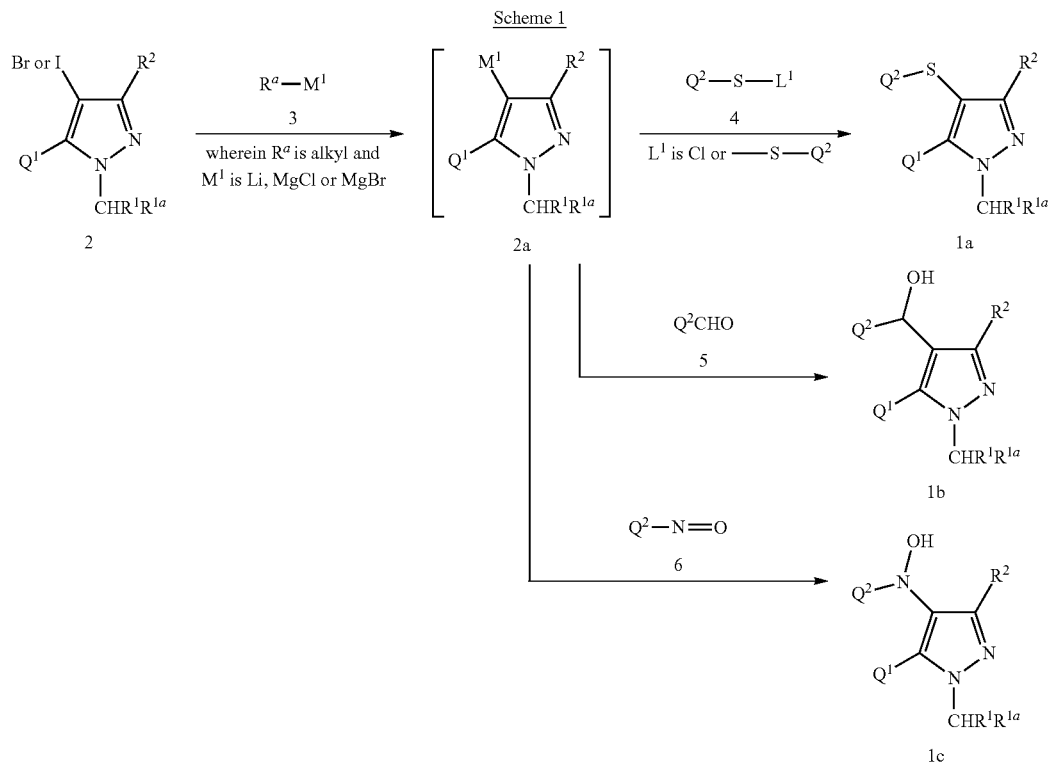

Electrophiles of Formulae 4, 5 and 6 are commercially available and can be prepared by methods known in the art. Compounds of Formula 2 are known and can be prepared by the method disclosed in Scheme 6 below, and by a variety of methods disclosed in the chemical literature.

Alternatively, as shown in Scheme 2, compounds of Formula 1b (i.e. Formula 1 wherein X is C(OH)) can be prepared from the corresponding ketone compounds of Formula 7 using standard reduction techniques. Typical reaction conditions involve contacting a compound of Formula 7 with a boron-based reducing agent such as sodium borohydride or sodium triacetoxyborohydride in a solvent such as methanol, ethanol or tetrahydrofuran. Other techniques known to those skilled in the art may also be employed. For relevant references, see, for example, *Journal of the American Chemical Society* 2006, 128, 9998-9999 and PCT Publication WO 2010/030922 A1 (Examples 8 and 11).

Scheme 2

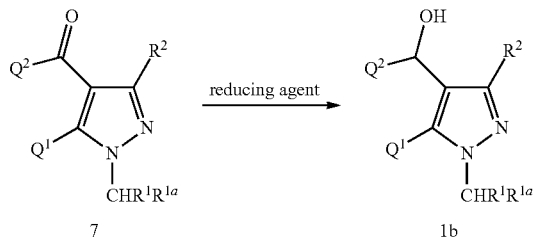

As shown in Scheme 3, compounds of Formula 7 can also be treated with alkylmagnesium halides to provide compounds of Formula 1d (i.e. Formula 1 wherein X is C(OH) $R^{5a}$ and $R^{5a}$ is $C_1$-$C_6$ alkyl). Typically the reaction is run in presence of zinc chloride and in a solvent such as diethyl ether or tetrahydrofuran at temperatures from about 0-100° C. For reaction conditions; see, for example, *Journal of the American Chemical Society* 2006, 128, 9998-9999.

Scheme 3

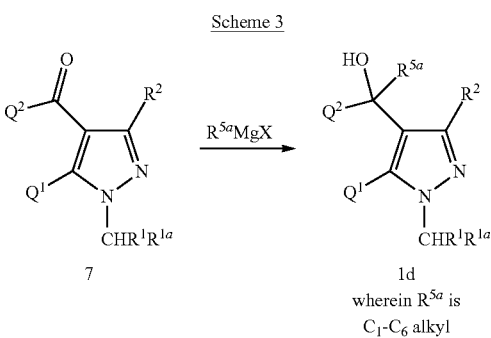

wherein $R^{5a}$ is $C_1$-$C_6$ alkyl

As shown in Scheme 4, intermediates of Formula 7 can be prepared using a method analogous to Scheme 1, wherein anions of Formula 2a are treated with benzoyl chlorides of formula $Q^1C(=O)Cl$ (i.e. Formula 8) or benzamides of formula $Q^1C(=O)N(Me)OMe$ (i.e. Formula 9) to provide compounds of Formula 7. In cases where the electrophile is $Q^1C(=O)Cl$, the addition of a second organometallic reagent such as zinc chloride, zinc bromide or a monovalent copper salt such as copper(I) iodide or copper(I) cyanide before the addition of the electrophile promotes reactivity. For a related reference, see, for example, *Journal of Medicinal Chemistry* 1986, 29(9), 1628-11637.

Scheme 4

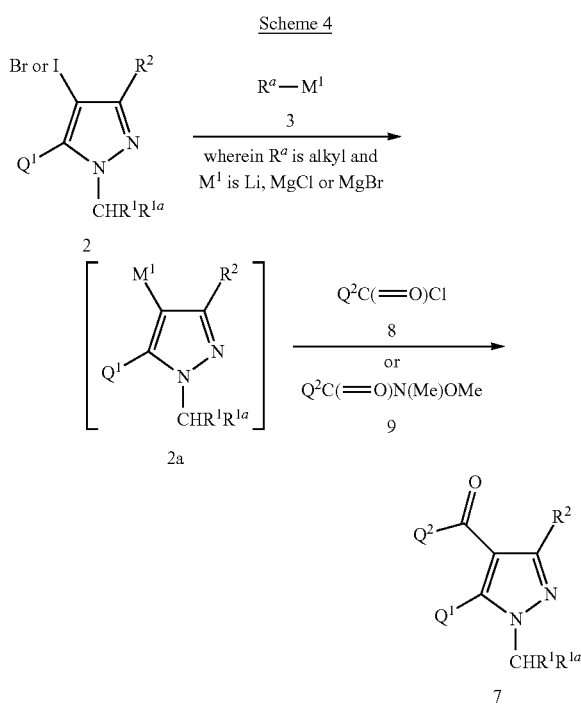

In an alternate approach, intermediates of Formula 7 can also be prepared from compounds of Formula 10 using Friedel-Crafts acylation conditions as illustrated in Scheme 5. In this method, a compound of Formula 10 is contacted with an acid chloride of Formula 11 in the presence of a Lewis acid (e.g., aluminum chloride, boron trifluoride diethyl etherate or tin tetrachloride) in a solvent such as dichloromethane, tetrachloroethane or nitrobenzene, at temperatures ranging between about 0 to 200° C. In the present disclosure, Example 1, Step D illustrates the method of Scheme 5.

Scheme 5

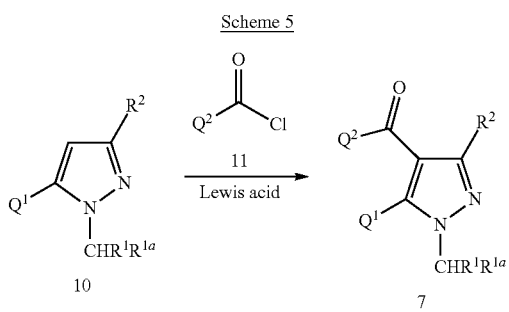

As shown in Scheme 6, intermediates of Formula 2 are readily prepared from compounds of Formula 10 by treatment with a halogenating agent. Suitable halogenating agents for this method include N-bromosuccinimide (NBS), N-iodosuccinimide (NIS), bromine, sodium bromite, thionyl chloride, oxalyl chloride, phenylphosphonic dichloride or phosgene. Particularly useful is N-bromosuccinimide (NBS) and N-iodosuccinimide (NIS). Suitable solvents for this reaction include, for example, N,N-dimethylformamide, N,N-dimethylacetamide, dichloromethane, chloroform, chlorobutane, benzene, xylenes, chlorobenzene, tetrahydrofuran, p-dioxane, acetonitrile, and the like. Optionally, a base such as sodium carbonate, triethylamine, pyridine, N,N-dimethylaniline, and the like can be added. Typical reaction temperatures range from about ambient temperature to 200° C. For representative procedures, see, for example, Czarnocki et al., *Synthesis Communications* 2007, 37(1), 137-147, and PCT Publication WO 2010/030922 A1 (Example 3, Step C, Example 4, Step C and Example 9, Step D).

Scheme 6

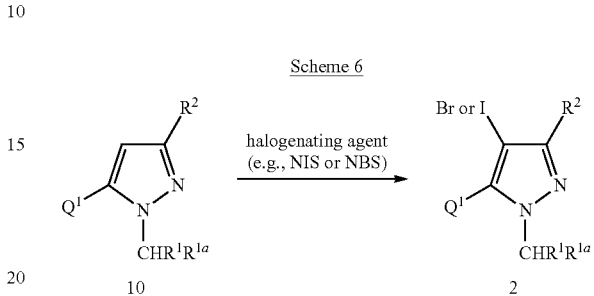

As shown in Scheme 7, intermediates of Formula 10 can be prepared by reaction of a 5-bromo or 5-iodo pyrazole of Formula 12 under transition-metal-catalyzed cross-coupling reaction conditions. In this method reaction of a pyrazole of Formula 12 is contacted with a compound of formula $Q^1$-$M^2$ (i.e. Formula 13) in the presence of a suitable palladium, copper or nickel catalyst, to provide a compound of Formula 10. Suitable compounds of formula $Q^1$-$M^2$ include organoboronic acids (e.g., $M^2$ is $B(OH)_2$), organoboronic esters (e.g., $M^2$ is $B(—OC(CH_3)_2C(CH_3)_2O—)$), organotrifluoroborates (e.g., $M^2$ is $BF_3K$), organotin reagents (e.g., $M^2$ is $Sn(n-Bu)_3$, $Sn(Me)_3$), Grignard reagents (e.g., $M^2$ is MgBr or MgCl) or organozinc reagents (e.g., $M^2$ is ZnBr or ZnCl). Suitable metal catalysts include, but are not limited to: palladium(II) acetate, palladium(II) chloride, tetrakis(triphenylphosphine)-palladium(0), bis(triphenylphosphine)palladium(II) dichloride, dichloro[1,1'-bis(diphenyl-phosphino)ferrocene]palladium(II), bis(triphenylphosphine)dichloronickel(II) and copper(I) salts (e.g., copper(I) iodide, copper(I) bromide, copper(I) chloride, copper(I) cyanide or copper(I) triflate). Optimal conditions for each reaction will depend on the catalyst used and the counterion attached to the coupling reagent (i.e. $M^2$), as is understood by one skilled in the art. In some cases the addition of a ligand such as a substituted phosphine or a substituted bisphosphinoalkane promotes reactivity. Also, the presence of a base such as an alkali carbonate, tertiary amine or alkali fluoride may be necessary for some reactions involving organoboron reagents of the formula $Q^1$-$M^2$. For reviews of this type of reaction see: E. Negishi, *Handbook of Organopalladium Chemistry for Organic Synthesis*, John Wiley and Sons, Inc., New York, 2002; N. Miyaura, *Cross-Coupling Reactions: A Practical Guide*, Springer, New York, 2002; H. C. Brown et al., *Organic Synthesis via Boranes*, Vol. 3, Aldrich Chemical Co., Milwaukee, Wis., 2002; Suzuki et al., *Chemical Review* 1995, 95, 2457-2483 and *Accounts of Chemical Research* 2007, 40, 275-286. For representative procedures, see, for example, PCT Publication WO 2010/030922 A1 (Example 9, Step C).

Scheme 7

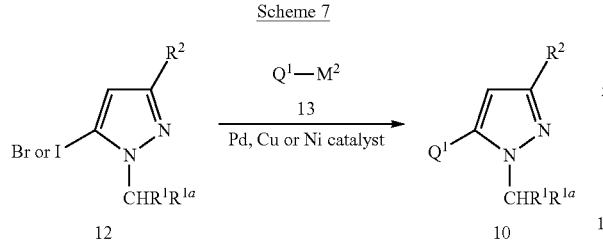

Alternatively, as shown in Scheme 8, intermediates of Formula 10 can be prepared by cyclization of enones of Formula 14 with an appropriately substituted hydrazine of formula NH$_2$NH—CHR$^1$R$^{1a}$ (i.e. Formula 15) and subsequent oxidation of pyrazolines of Formula 16. Useful oxidizing reagents include bromine (for conditions see, for example, *Indian Journal of Heterocyclic Chemistry*, 2001, 11(1), 21-26), elemental sulfur, manganese dioxide, 2,3-dichloro-5,6-dicyanobenzoquinone (DDQ), chloranil (for conditions see, for example, *Russian Journal of Organic Chemistry* 2006, 42(8), 1113-1119) and oxygen optionally in the presence of a metal catalyst such as cobalt acetate (for conditions see, for example, *Tetrahedron* 2006, 62(11), 2492-2496 and *Chinese Chemical Letters* 2008, 19(9), 1013-1016). Useful solvents for this reaction include N,N-dimethylformamide, tetrahydrofuran, toluene, water, dichloromethane, tetrachloroethane, and mixtures of these or similar solvents, at temperatures from ambient to 200° C. The reaction of hydrazines with enones and the preparation of the enones is well-known in the art, see, for example, *Synthesis* 2012, 44, 2401-2407 and PCT Publication WO 2010/030922 A1 (Example 4, Step B). Also, in the present disclosure, Example 1, Step C illustrates the method of Scheme 8.

Scheme 8

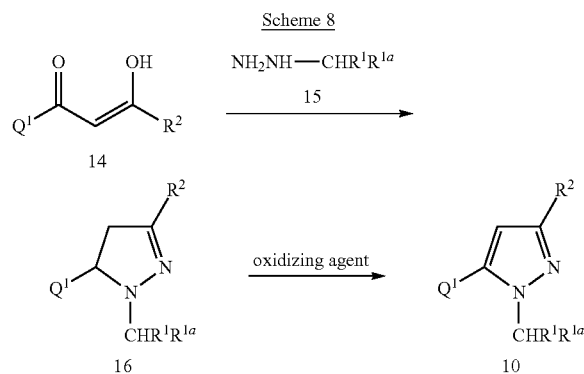

As shown in Scheme 9, compounds of Formula 12 can be prepared by alkylation of corresponding pyrazoles of Formula 17 with an alkylating agent of formula CHR$^1$R$^{1a}$-L$^2$ (i.e. Formula 18) wherein L$^2$ is a leaving group such as halogen or (halo)alkylsulfonate (e.g., Cl, Br, I, p-toluenesulfonate, methanesulfonate or trifluoromethanesulfonate). General procedures for alkylations of this type are well-known in the art and can be readily adapted to prepare compounds of the present invention. Particularly useful alkylating agents for preparing compounds of Formula 12 (wherein R$^1$ and R$^{1a}$) are H are diazomethane or iodomethane using general procedures known in the art, such as those described in *Tetrahedron Letters* 2009, 50(49), 6783-6786 and PCT Publication WO 2010/030922 A1 (Example 9, Step B).

Scheme 9

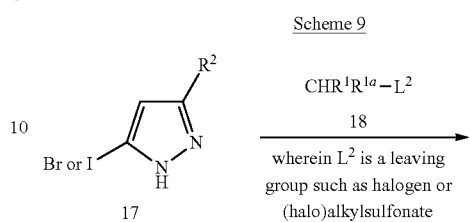

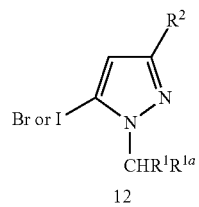

Starting compounds of Formula 17 are known and can be prepared by a variety of methods disclosed in the chemical literature, see, for example, PCT Publication WO 2010/030922 A1 (Example 9, Step A).

As shown in Scheme 10, Compounds of Formula 1 wherein X is O, S or NR$^4$ can be prepared by reacting compounds of Formula 19 (e.g., 4-hydroxypyrazoles for X being O, 4-mercaptopyrazoles for X being S and 4-aminopyrazoles for X being NR$^4$) with compounds of Formula 20 where L$^2$ is a leaving group such as halogen or (halo) alkylsulfonate (e.g., Cl, Br, I, p-toluenesulfonate, methanesulfonate or trifluoromethanesulfonate), optionally in the presence of a metal catalyst, and generally in the presence of a base and a polar aprotic solvent such as N,N-dimethylformamide or dimethyl sulfoxide. Compounds of Formula 20 wherein Q$^2$ is a phenyl ring substituted with electron-withdrawing substituents react with compounds of Formula 19 by direct displacement of the leaving group L$^2$ to provide compounds of Formula 1. Typically for these types of reactions L$^2$ is F or Cl. Compounds of Formula 20 wherein Q$^2$ is a phenyl ring not substituted with an electron-withdrawing substituent, or in general, to improve reaction rate, yield or product purity, the use of a metal catalyst in amounts ranging from catalytic up to superstoichiometric can facilitate the desired reaction. Typically for these conditions, L$^2$ is Br or I or a sulfonate such as —OS(O)$_2$CF$_3$ or —OS(O)$_2$(CF$_2$)$_3$CF$_3$. For example, the reaction can be run in the presence of a metal catalyst such as copper salt complexes (e.g., CuI with N,N'-dimethylethylenediamine, proline or bipyridyl), or palladium complexes (e.g., tris(dibenzylideneacetone)dipalladium(0)) or palladium salts (e.g., palladium acetate) with ligands such as 4,5-bis(diphenylphosphino)-9,9-dimethylxanthene, 2-dicyclohexylphosphino-2', 4',6'-triisopropylbiphenyl or 2,2'-bis-(diphenylphosphino)1, 1'-binaphthalene, and with a base such as potassium carbonate, cesium carbonate, sodium phenoxide or sodium tert-butoxide, in a solvent such as N,N-dimethylformamide, 1,2-dimethoxyethane, dimethyl sulfoxide, 1,4-dioxane or toluene, optionally containing an alcohol such as ethanol. For representative procedures, see, for example, *Archives of Pharmacal Research* 2002, 25(6), 781-785 and PCT Publication WO 2010/030922 A1 (Example 1, Step C and Example 2, Step G).

Scheme 10

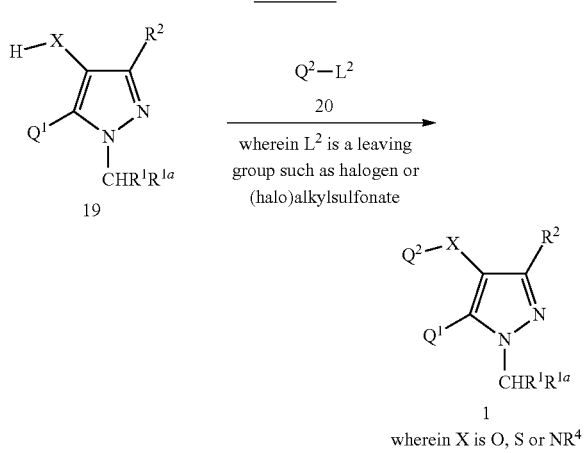

wherein X is O, S or NR⁴

Compounds of Formula 19 are commercially available and their preparation is known in the art, see, for example, *Journal für Praktische Chemie* (Leipzig) 1911, 83, 171-182, *Journal of the American Chemical Society* 1954, 76, 501-503 and PCT Publication WO 2010/030922 A1 (Example 1, Steps A through B).

As shown in Scheme 11, compounds of Formula 1 can also be prepared by reaction of a 5-bromo or 5-iodo pyrazole of Formula 21 with an organometallic compound of Formula 22 under transition-metal-catalyzed cross-coupling reaction conditions analogous to those described for Scheme 7. Reaction of a pyrazole of Formula 21 with a boronic acid, trialkyltin or an organomagnesium reagent of Formula 22 in the presence of a palladium or nickel catalyst and optionally a ligand (e.g., triphenylphosphine, dibenzylideneacetone, dicyclohexyl(2',6'-dimethoxy[1,1'-biphenyl]-2-yl)phosphine) and a base affords a compound of Formula 1. For example, a compound of Formula 22 wherein M³ is B(OH)₂, B($-$OC(CH₃)₂C(CH₃)₂O$-$) or B(O-i-Pr)₃Li reacts with a 5-bromo- or 5-iodopyrazole of Formula 21 in the presence of dichlorobis(triphenylphosphine) palladium(II) and an aqueous base such as sodium carbonate or potassium hydroxide, in solvents such as 1,4-dioxane, 1,2-dimethoxyethane, toluene or ethyl alcohol, or under anhydrous conditions with the use of a ligand such as phosphine oxide or phosphite ligand (e.g., diphenylphosphine oxide) and potassium fluoride in a solvent such as 1,4-dioxane to provide a compound of Formula 1. For references, see *Angewandte Chemie, International Edition* 2008, 47(25), 4695-4698 and PCT Publication WO 2010/030922 A1 (Example 3, Step D).

Scheme 11

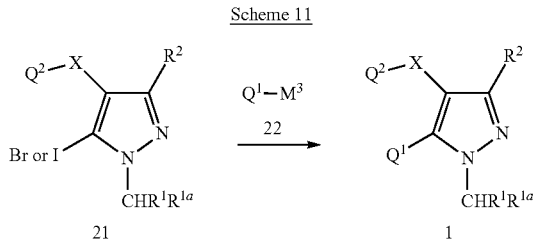

Compounds of Formula 21 can be prepared via halogenation methods analogous to those described for Scheme 6 (for conditions see PCT Publication WO 2010/030922 A1, Example 3, Step C).

Compounds of Formula 1 can be subjected to various nucleophilic, metalation and oxidation reactions to add substituents or modify existing substituents, and thus provide other functionalized compounds of Formula 1. For example, as shown in Scheme 12, compounds of Formula 1e (i.e. Formula 1 wherein X in NR⁴ and R⁴ is other than H) can be prepared by reacting corresponding compounds of Formula 1f (i.e. Formula 1 wherein X is NH) with an electrophile comprising R⁴ (i.e. Formula 23) typically in the presence of a base such as sodium hydride and a polar solvent such as N,N-dimethylformamide. In this context the expression "electrophile comprising R⁴" means a chemical compound capable of transferring an R⁴ moiety to a nucleophile (such as the nitrogen atom in Formula 1f). Often electrophiles comprising R⁴ have the formula R⁴L³ wherein L³ is a nucleofuge (i.e. leaving group in nucleophilic reactions). Typical nucleofuges include halogens (e.g., Cl, Br, I) and sulfonates (e.g., OS(O)₂CH₃, OS(O)₂CF₃, OS(O)₂-(4-CH₃-Ph)). However, some electrophiles comprising R⁴ do not comprise a nucleofuge; an example is sulfur trioxide (SO₃) which, after deprotonation (such as by a base of the formula M⁺H⁻ wherein M⁺ is a cation) of the nitrogen atom in Formula 1f, can bond to the nitrogen atom as a $-$S($=$O)₂OM substituent.

Scheme 12

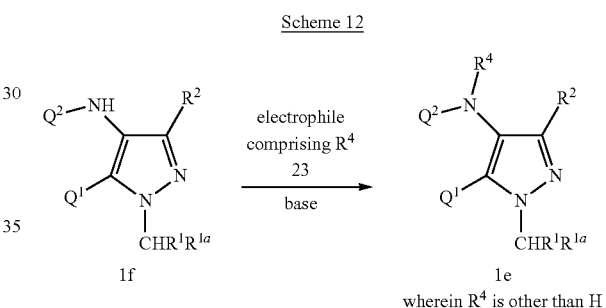

wherein R⁴ is other than H

In another example, as shown in Scheme 13, a fluoro can be introduced at the 3-position of the pyrazole ring by treating compounds Formula 1h (i.e. Formula 1 wherein R² is chlorine) with potassium fluoride or cesium fluoride in presence of a solvent such as dimethyl sulfoxide or N,N-dimethylformamide at about 0-25° C. for about 30 minutes to 4 h, using procedures such as those described in *Zhurnal Organicheskoi Khimii* 1983, 19, 2164-2173.

Scheme 13

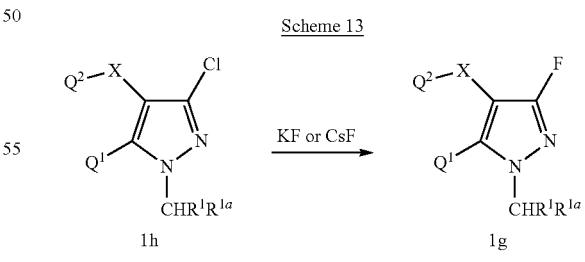

Additionally, as shown in Scheme 14, sulfoxides and sulfones of Formula 1i (i.e. Formula 1 wherein X is S($=$O)ₘ and m is 1 or 2) can be prepared by oxidation of compounds of Formula 1a (i.e. Formula 1 wherein X is S). Typically, an oxidizing agent in an amount of about 1 to 4 equivalents, depending on the oxidation state of the desired product, is added to a mixture of a compound of Formula 1a and a solvent. Useful oxidizing agents include Oxone® (potassium peroxymonosulfate), potassium permanganate, hydrogen peroxide, sodium periodate, peracetic acid and 3-chloroperbenzoic acid. The solvent is selected with regard to the oxidizing agent employed. Aqueous ethanol or aqueous acetone is preferably used with potassium peroxymonosulfate, and dichloromethane is generally preferable with 3-chloroperbenzoic acid. Useful reaction temperatures typically range from about −78 to 90° C. Oxidation reactions of this type are described in *J. Agric. Food Chem.* 1984, 32, 221-226 and *J. Agric. Food Chem.* 2008, 56, 10160-10167.

Scheme 14

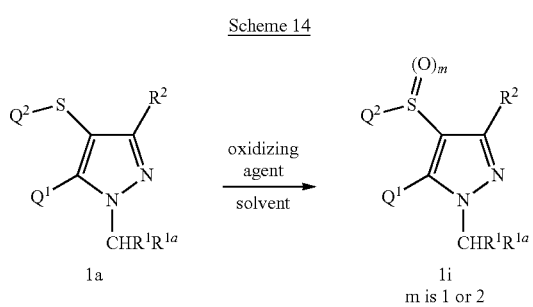

1a 1i
m is 1 or 2

Furthermore, for some compounds of Formula 1 the $R^{3a}$ and/or $R^{3b}$ substituents attached to $Q^1$ and $Q^2$ may be more conveniently incorporated after forming the central pyrazole ring with $Q^1$ and $Q^2$ already attached. For example, compounds of Formula 1j (i.e. Formula 1 wherein $Q^1$ is phenyl and $R^{3b}$ is alkoxy, alkenyloxy, alkynyloxy, cycloalkoxy, and the like) can be prepared by reacting hydroxyphenyl derivatives of Formula 24 with compounds of formula 25 wherein $L^2$ is a suitable leaving group such as halogen or (halo)alkylsulfonate (e.g., Cl, Br, I, p-toluenesulfonate, methanesulfonate or trifluoromethanesulfonate), in the presence of a base such as potassium carbonate, potassium tert-butoxide, sodium hydride or triethylamine, and in an aprotic solvent such as N,N-dimethylformamide, acetonitrile, dimethylsulfoxide or tetrahydrofuran at a temperature between about −20 and 150° C. This reaction works particularly well when the hydroxy group (—OH) is in the 4-position of the phenyl ring of Formula 24 and at least one of the substituents $R^{3a}$ is an electron withdrawing group such as fluoride. For a reference describing the general method of Scheme 15 see *Chemical & Pharmaceutical Bulletin* 2008, 56(8), 1126-1137.

Scheme 15

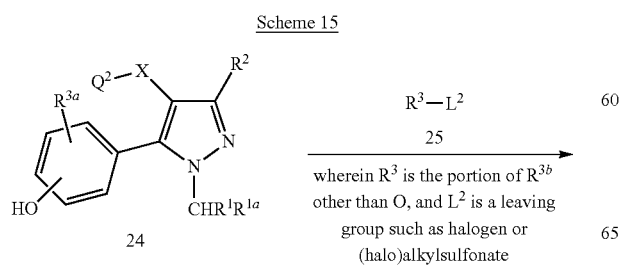

24

$R^3$—$L^2$
25
wherein $R^3$ is the portion of $R^{3b}$ other than O, and $L^2$ is a leaving group such as halogen or (halo)alkylsulfonate

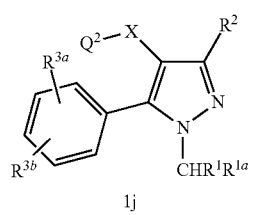

1j
wherein $R^{3b}$ is alkoxy, alkenyloxy, alkynyloxy, cycloalkoxy, and the like The resulting alkoxy compounds of Formula 1j can themselves be used in further reactions to prepare compounds of Formula 1 wherein $R^{3a}$ is —U—V-T (see, for example, PCT Publication WO 2007/149448 A2).

As shown in Scheme 16, hydroxyphenyl derivatives of Formula 24 can be prepared from boronic acids or esters of Formula 26 via oxidative hydroxylation. A variety of oxidizing agents can be used in this method, particularly useful reagents include hydrogen peroxide and N-oxides such as N,N,4-trimethylbenzenamine N-oxide according to procedures reported in *Tetrahedron Letters* 2012, 53, 6004-6007 and *Organic Letters* 2012, 14(13), 3494-3497.

Scheme 16

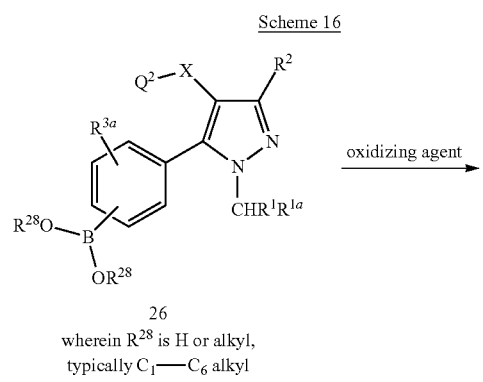

26
wherein $R^{28}$ is H or alkyl,
typically $C_1$—$C_6$ alkyl

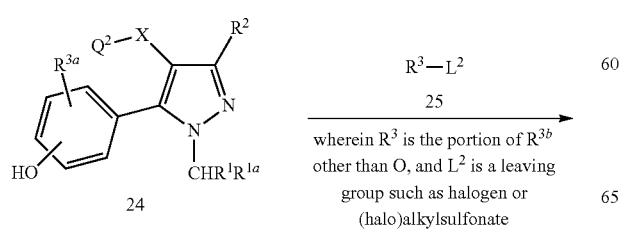

24

As shown in Scheme 17, the intermediate boronic acids or esters of Formula 26 can be prepared by contacting compounds of Formula 27 wherein $L^3$ is Cl, Br, I or a triflate group with a boronic acid or ester of Formula 28. The reaction is carried out in the presence a palladium catalyst such as $PdCl_2dppf$ ($PdCl_2$-1,1'-bis(diphenylphosphino)ferrocene) and a base such as potassium acetate in a solvent such as dioxane at about 80 to 100° C. The stoichiometry of this method requires at least one molar equivalent of the boronic acid or ester to obtain complete conversion of the compound of Formula 27 to the corresponding compound of Formula 26. However, to obtain rapid reaction rates and high yields, an excess of the boronic acid is typically used, often at least 1.5 to 2.0 molar equivalents relative to the compound of Formula 27. A wide variety of boronic acids, esters, and their derivatives can be used in the method of Scheme 17. Particularly useful derivatives include, for example, trialkoxy boranes such as trimethoxyborane. Coupling reactions with boronic acids or derivatives in the presence of palladium catalysts are known, and the wide variety of known general procedures can be readily adapted by one skilled in the art for use in the method of Scheme 17. For articles about this type of functional group transformation, see, for example, *Tetrahedron* 2000, 56, 9655-9662 and *Chemical Communications* 2004, 1, 38.

Formula 24. For a reference describing the general method of Scheme 18 see *Bioorganic & Medicinal Chemistry* 2011, 19, 2997-3004.

Scheme 18

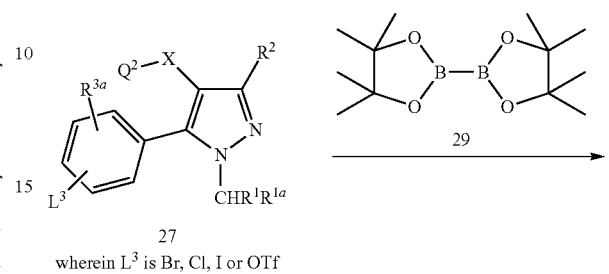

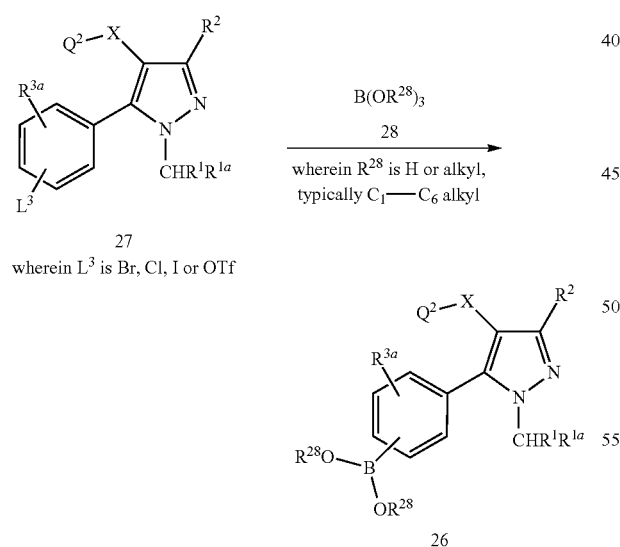

Analogous to the method of Scheme 17, compounds of Formula 27 can be contacted with bis(pinacolato)diboron (i.e. Formula 29) to provide compounds of Formula 30. Compounds of Formula 30 can also be used in the method of Scheme 16 to provide hydroxyphenyl derivatives of One skilled in the art recognizes that the construction of $R^{3b}$ attached to $Q^1$ in the methods of Schemes 15-18 can alternatively be performed for the construction of $R^{3b}$ attached to $Q^2$. Therefore the methods described in Schemes 15-18 should be considered broadly useful for the construction of $R^{3b}$ attached to $Q^1$ and for the construction of $R^{3b}$ attached $Q^2$. Furthermore, the methods of Schemes 15-18 can also be performed when $Q^1$ or $Q^2$ is other then phenyl.

One skilled in the art will also recognize that the methods of Schemes 15-18 can alternatively be carried out at other stages in the preparation of pyrazoles of Formula 1. For example, as shown in Scheme 19, using a method analogous to Scheme 15 compounds of Formula 31 can be prepared (present Example 2, Step C and Example 3, Step A illustrate the preparation of a compound of Formula 31 using the method Scheme 15), and then subsequently reduced using the method described in Scheme 2 or alkylated using the method described in Scheme 3 to provide compounds of Formula 1j wherein X is CH(OH) or C(OH)$R^{5a}$ and $R^{5a}$ is other then H, respectively.

Scheme 19

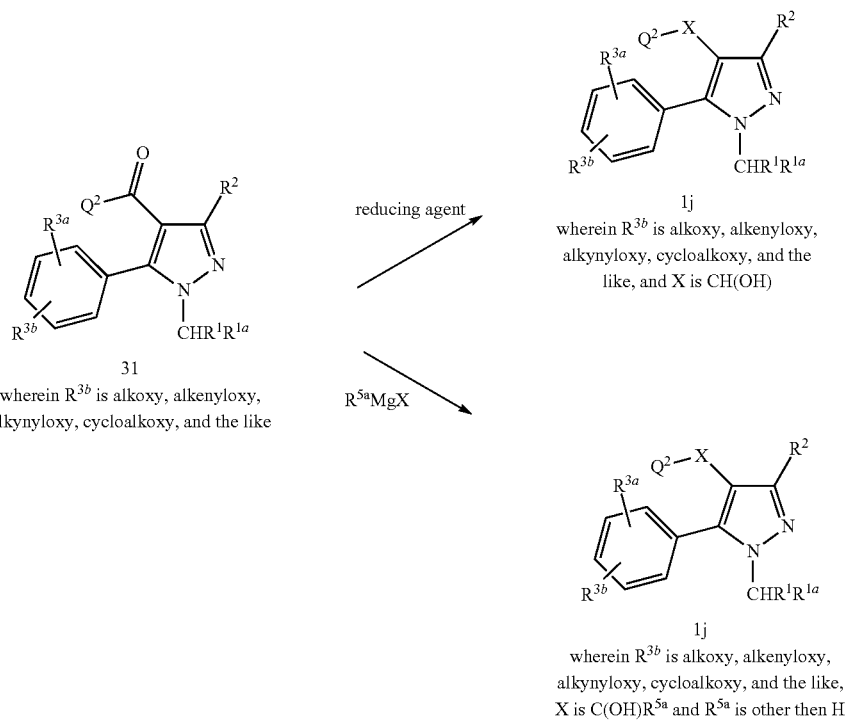

Numerous other methods known to those skilled in the art can be employed for the construction of an $R^{3b}$ group attached to $Q^1$ or $Q^2$. For example, as depicted in Scheme 20, compounds of Formula 1k (i.e. Formula 1 wherein $Q^1$ is phenyl, $R^{3b}$ is W and W is a heterocycle linked through nitrogen) can be prepared from compounds of Formula 32 wherein $L^3$ is Cl, Br, I or a triflate group with heterocycles of Formula 33 using Buchwald-Hartwig coupling reaction conditions. Typically these reactions are conducted in an inert solvent in the presence of a suitable ligand, a copper (I) salt (e.g., CuI or CuBr) and a base (e.g., sodium or potassium carbonate) at about ambient temperature to 230° C. for about 1 to 48 h. Typical ligands include 1,2-diaminocyclohexane and phenanthroline. Suitable solvents include dioxane, 1,2-diethoxyethane and toluene. Conditions for Buchwald-Hartwig couplings are well documented in the literature, see for example, *Tetrahedron Letters,* 2010, 52(38), 5052 and *Journal of Medicinal Chemistry* 2010, 53(10), 31-8.

Scheme 20

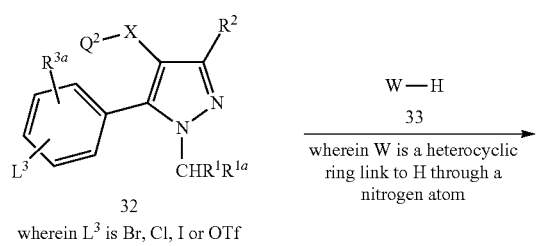

-continued

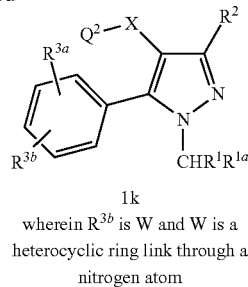

1k
wherein $R^{3b}$ is W and W is a heterocyclic ring link through a nitrogen atom Alternatively, as shown in Scheme 21 (Method A), compounds of Formula 1k (i.e. Formula 1 wherein $Q^1$ is phenyl, $R^{3b}$ is W and W is a heterocycle linked through nitrogen) can be prepared from boronic acids or esters of Formula 26 and compounds of Formula 33 using Chan-Lam coupling conditions. Typically the reaction is run in presence of a Cu(II) salt, oxygen, and a base at about ambient temperature to 150° C. for about 24 to 72 h. Suitable Cu(II) salts include are $Cu(OAc)_2$, $CuBr_2$ and $CuI_2$, suitable bases include pyridine, quinoline and triethylamine, and suitable solvents include dichloromethane, chloroform, diethyl ether and tetrahydrofuran. For representative conditions see *Tetrahedron Letters,* 1998, 38, 2941 and PCT Patent Publication WO 2003/072547.

As depicted in Scheme 21 (Method B), preparation of compounds of Formula 1m (i.e. Formula 1 wherein $Q^1$ is phenyl, $R^{3b}$ is W, and W is a heterocycle linked through carbon) can be accomplished via the well-known Suzuki reaction involving Pd-catalyzed cross-coupling of an heterocyclic iodide or bromide of Formula 34 with a boronic acid of Formula 26. Many palladium catalysts are useful for this type of transformation; a typical catalyst is tetrakis(triphenylphosphine)palladium(0). Solvents such as tetrahydrofuran, acetonitrile, diethyl ether and dioxane are suitable. For a thorough review of palladium chemistry see Li, J. J.; Gribble, G. W.; Editors; *Palladium in Heterocyclic Chemistry: A Guide for the Synthetic Chemist*, Elsevier: Oxford, U K, 2000. For representative journal references, see, for example, *Angewandte Chemie International Edition*, 2006, 45, 3484 and *Tetrahedron Letters*, 2002, 58(14), 2885.

Scheme 22

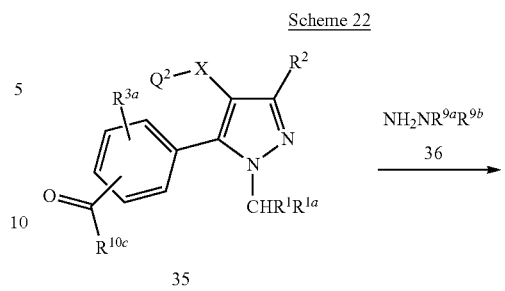

Scheme 21

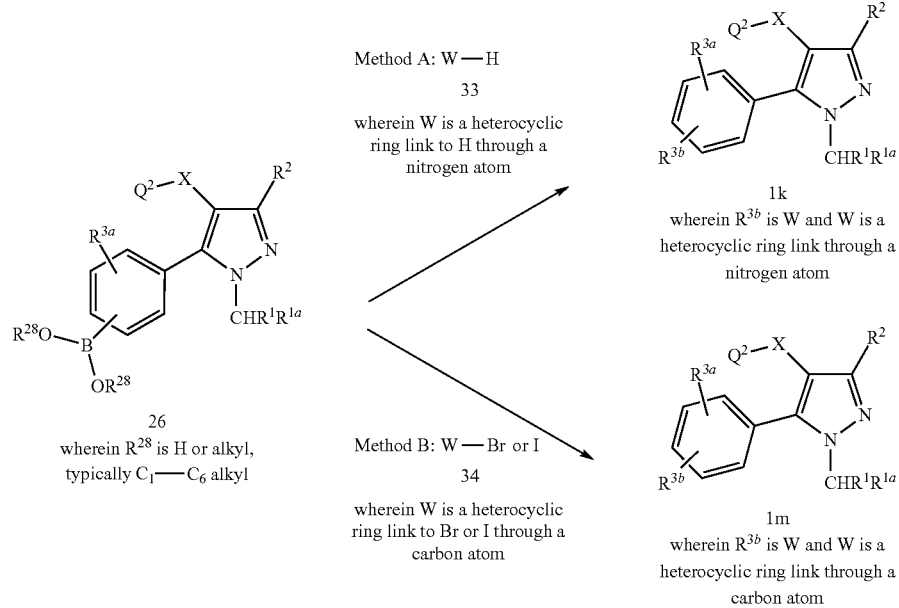

Cyclic boronates of Formula 30 are also useful in the method of Scheme 21.

One skilled in the art recognizes that the construction of $R^{3b}$ attached to $Q^1$ in the methods of Schemes 20 and 21 can alternatively be performed for the construction of $R^{3b}$ attached to $Q^2$. Therefore the methods described in Schemes 20 and 21 should be considered broadly useful for construction of $R^{3b}$ attached to either $Q^1$ or $Q^2$.

Furthermore, a wide variety of alternative methods exist for the construction of other $R^{3b}$ groups, including well documented functional group transformations of ketones, esters, acids, aldehydes, nitriles and the like. For example, as depicted in Scheme 22, reaction of an aldehyde or ketone of Formula 35 with a hydrazine of Formula 36 provides compounds of Formula 1n (i.e. Formula 1 wherein $Q^1$ is phenyl and $R^{3a}$ is —$CR^{10c}$=$NNR^{9a}R^{9b}$). For leading references teaching this method see *Tetrahedron* 2000, 56(41), 8071-8076, *Journal of Organic Chemistry* 2005, 70(2), 596-602 and *Synthetic Communications* 1997, 27(7), 1199-1207.

-continued

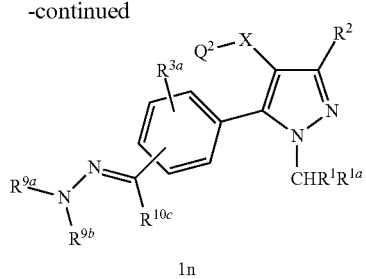

Aldehydes and ketones of Formula 35 can be prepared from the corresponding bromo, iodo or triflate derivatives via transition metal-catalyzed cross-coupling reactions. For conditions see *J. Am. Chem. Soc.*, 2008, 130, 15549-15563, *Journal of Medicinal Chemistry* 2003, 46, 5651-5662 and *Tetrahedron* 2003, 59, 8199-8202.

Additionally, it will be recognized by one skilled in the art that various functional groups can be converted into others to provide different compounds of Formula 1. For example, compounds of Formula 1 in which $R^2$ is methyl, ethyl or cyclopropyl can be modified by free-radical halogenation to form compounds of Formula 1 wherein $R^2$ is halomethyl or halocyclopropyl. The halomethyl compounds can themselves be used as intermediates to prepare compounds of Formula 1 wherein $R^2$ is hydroxymethyl or cyanomethyl. Compounds of Formula 1 or intermediates for their preparation may contain aromatic nitro groups, which can be reduced to amino groups, and then be converted via reactions well-known in the art, such as the Sandmeyer reaction, to various halides, providing other compounds of Formula 1. By similarly known reactions, aromatic amines (anilines) can be converted via diazonium salts to phenols, which can then be alkylated to prepare compounds of Formula 1 with alkoxy substituents. Likewise, aromatic halides such as bromides or iodides, prepared via the Sandmeyer reaction, can be reacted with alcohols under copper-catalyzed conditions, such as the Ullmann reaction or known modifications thereof, to provide compounds of Formula 1 that contain alkoxy substituents. Additionally, some halogen groups, such as fluorine or chlorine, can be displaced with alcohols under basic conditions to provide compounds of Formula 1 containing the corresponding alkoxy substituents. Compounds of Formula 1, or precursors thereof, in which $R^2$ is halide, preferably bromide or iodide, are particularly useful intermediates for transition metal-catalyzed cross-coupling reactions to prepare compounds of Formula 1. These types of reactions are well documented in the literature; see, for example, Tsuji in *Transition Metal Reagents and Catalysts: Innovations in Organic Synthesis*, John Wiley and Sons, Chichester, 2002; Tsuji in *Palladium in Organic Synthesis*, Springer, 2005; and Miyaura and Buchwald in *Cross Coupling Reactions: A Practical Guide*, 2002; and references cited therein.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

The above reactions can also in many cases be performed in alternate sequence, such as the preparation of 1H pyrazoles for use in the reaction in Scheme 7 by reactions illustrated later for the general preparation of substituted pyrazoles. The presence of certain functional groups may not be compatible with all of these reaction conditions, and the use of protecting groups may be desirable for obtaining the desired products with improved yields and or purity.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane in $CDCl_3$ unless otherwise noted; "s" means singlet, "d" means doublet, "t" means triplet, "m" means multiplet, "dd" means doublet of doublets and "dt" means doublet of triplets.

Example 1

Preparation of α-(2-chloro-4-fluorophenyl)-5-[2,6-difluoro-4-(1H-pyrazol-1-yl)phenyl]-1,3-dimethyl-1H-pyrazole-4-methanol (Compound 3)

Step A: Preparation of 4-bromo-2,6-difluorobenzoyl chloride

A mixture of 4-bromo-2,6-difluorobenzoic acid (2.0 g, 9.1 mmol) and thionyl chloride (10 mL) was heated at 100° C. for 16 h. The reaction mixture was distilled under reduced pressure, diluted with toluene (10 mL), and again distilled under reduced pressure to provide the title compound.

Step B: Preparation of (2Z)-1-(4-bromo-2,6-difluorophenyl)-3-hydroxy-2-buten-1-one To a mixture of 2,4-pentanedione (0.93 mL, 9.1 mmol) in acetonitrile (10 mL) was added magnesium chloride (0.95 g, 10 mmol). After 0.5 h, the reaction mixture was cooled to 0° C. and then triethylamine (2.0 g, 19 mmol) was added, followed by 4-bromo-2,6-difluorobenzoyl chloride (i.e. the product of Step A) (2.3 g, 9.0 mmol) in acetonitrile (10 mL). After an additional 2 h, the reaction mixture was concentrated under reduced pressure, hydrochloric acid (concentrated, 2 mL) was added and the mixture was heated at 100° C. for 2 h. The reaction mixture was cooled to room temperature, water (100 mL) was added and the resulting mixture was extracted with ethyl acetate (3×5 mL). The combined organic layers were washed with saturated aqueous sodium chloride solution (50 mL), dried over sodium sulfate, filtered and concentrated under reduced pressure. The resulting material was purified by column chromatography on silica gel eluting with 5% ethyl acetate in petroleum ether to provide the title compound as a yellow oil (1.65 g).

1H NMR ($CDCl_3$): δ 15.39 (s, 1H), 7.16 (d, 2H), 5.84 (s, 1H), 2.17 (s, 3H).

Step C: Preparation of 5-(4-bromo-2,6-difluorophenyl)-1,3-dimethyl-1H-pyrazole

To a mixture triethylamine (1.2 g, 12.0 mmol) and methylhydrazine (0.42 mL, 7.942 mmol) at 0° C. was added a solution of (2Z)-1-(4-bromo-2,6-difluorophenyl)-3-hydroxy-2-buten-1-one (i.e. the product of Step B) (1.1 g, 4.0 mmol) in ethanol (20 mL). The reaction mixture was stirred at room temperature for 18 h and then concentrated under reduced pressure. Water (70 mL) was added to the resulting material and the mixture was extracted with ethyl acetate (2×50 mL), dried over sodium sulfate and concentrated under reduced pressure. The residue was purified by column chromatography on silica gel eluting with 4% ethyl acetate in petroleum ether to provide the title compound as an off-white solid (420 mg).

1H NMR (CDCl$_3$): δ 7.24-7.19 (m, 2H), 6.15 (s, 1H), 3.69 (s, 3H), 2.31 (s, 3H).

Step D: Preparation of [5-(4-bromo-2,6-difluorophenyl)-1,3-dimethyl-1H-pyrazol-4-yl](2-chloro-4-fluorophenyl)methanone To a mixture of 5-(4-bromo-2,6-difluorophenyl)-1,3-dimethyl-1H-pyrazole (i.e. the product of Step C) (0.6 g, 2.1 mmol) in tetrachloroethane (8 mL) at 0° C. was added aluminum chloride (0.70 g, 5.2 mmol), followed 2-chloro-4-fluorobenzoyl chloride (1.4 g, 7.3 mmol). The reaction mixture was heated at 150° C. for 12 h. After cooling to room temperature, the reaction mixture was quenched with ice water and then extracted with ethyl acetate (4×100 mL). The combined organic layers were dried over sodium sulfate and concentrated under reduced pressure. The resulting material was purified by column chromatography on silica gel eluting with 10% ethyl acetate in petroleum ether to provide the title compound as an off-white solid (0.5 g).
1H NMR (DMSO-d$_6$): δ 7.47 (d, 2H), 7.32-7.27 (m, 2H), 7.10 (dt, 1H), 3.61 (s, 3H), 2.31 (s, 3H).

Step E: Preparation of (2-chloro-4-fluorophenyl)[5-[2,6-difluoro-4-(1H-pyrazol-1-yl)phenyl]-1,3-dimethyl-1H-pyrazol-4-yl]methanone To a solution of [5-(4-bromo-2,6-difluorophenyl)-1,3-dimethyl-1H-pyrazol-4-yl](2-chloro-4-fluorophenyl)methanone (i.e. the product of Step D) (0.30 g, 0.70 mmol) in 1,4-dioxane (4.5 mL) was added 1H-pyrazole (51 mg, 0.745 mmol), potassium carbonate (374 mg, 2.709 mmol) and copper iodide (26 mg, 0.14 mmol). The reaction mixture was sparged with argon gas for 20 minutes and then trans-N,N-dimethyl-1,2-cyclohexanediamine (0.02 mL, 0.14 mmol) was added and the mixture was heated at 110° C. for 24 h. After cooling to room temperature, the reaction mixture was filtered through a pad of Celite® (diatomaceous filter aid) on a sintered glass frit funnel. The filtrate was added to water (50 mL) and then extracted with ethyl acetate (2×50 mL). The combined organic layers were dried over sodium sulfate, filtered and concentrated under reduced pressure. The resulting material was purified by column chromatography on silica gel eluting with 20% ethyl acetate in petroleum ether to provide the title compound as an off-white solid (280 mg).
$^1$H NMR (DMSO-d$_6$): δ 8.60 (d, 1H), 7.84 (d, 1H), 7.61 (d, 2H), 7.35-7.32 (m, 1H), 7.28-7.24 (m, 1H), 7.12-7.07 (m, 1H), 6.63 (t, 1H), 3.65 (s, 3H), 2.33 (s, 3H).

Step F: Preparation of α-(2-chloro-4-fluorophenyl)-5-[2,6-difluoro-4-(1H-pyrazol-1-yl)phenyl]-1,3-dimethyl-1H-pyrazole-4-methanol To a mixture of (2-chloro-4-fluorophenyl)[5-[2,6-difluoro-4-(1H-pyrazol-1-yl)phenyl]-1,3-dimethyl-1H-pyrazol-4-yl]methanone (i.e. the product of Step E) (280 mg, 0.67 mmol) in ethanol (10 mL) at 0° C. was added sodium borohydride (250 mg, 6.7 mmol). After 18 h, the reaction mixture was quenched with ice water and extracted with ethyl acetate (3×30 mL). The combined organic layers were dried over sodium sulfate, filtered and concentrated under reduced pressure. The resulting material was purified by column chromatography on silica gel eluting with 25% ethyl acetate in petroleum ether to provide the title compound, a compound of the present invention, as a white solid (190 mg).

$^1$H NMR (DMSO-d$_6$): δ 8.63 (d, 1H), 7.84 (d, 1H), 7.69 (d, 1H), 7.56 (d, 1H), 7.47-7.43 (m, 1H), 7.18 (dd, 1H), 6.93-6.88 (m, 1H), 6.63 (t, 1H), 5.71 (s, 2H), 3.47 (s, 3H), 2.18 (s, 3H).

Example 2

Preparation of α-(2-chloro-4-fluorophenyl)-5-[4-(cyclopropylmethoxy)-2,6-difluorophenyl]-1,3-dimethyl-1H-pyrazole-4-methanol (Compound 10)

Step A: Preparation of (2-chloro-4-fluorophenyl)[5-[2,6-difluoro-4-(4,4,5,5-tetramethyl-1,3,2-dioxaborolan-2-yl)phenyl]-1,3-dimethyl-1H-pyrazol-4-yl]methanone A solution of [5-(4-bromo-2,6-difluorophenyl)-1,3-dimethyl-1H-pyrazol-4-yl](2-chloro-4-fluorophenyl)methanone (i.e. the product of Example 1, Step D) (4.8 g, 11 mmol) and bis(pinacolato)diborane (5.5 g, 22 mmol) in dioxane (40 mL) was sparged with a stream of argon gas for 10 minutes, and then [1,1'-bis(diphenylphosphino)ferrocene]-dichloropalladium(II) (0.88 g, 1.1 mmol) and potassium acetate (3.1 g, 33 mmol) were added to the reaction mixture. The reaction mixture was heated at 80° C. for 18 h, cooled to room temperature, and then filtered through a pad of Celite® (diatomaceous filter aid) on a sintered glass frit funnel. The filtrate concentrated under reduced pressure and the resulting material was diluted with water and extracted with ethyl acetate (3×100 mL). The combined organic layers were washed with water and saturated sodium chloride solution, and then dried over sodium sulfate, filtered and concentrated under reduced pressure to provide the title compound as a brown oil (6 g).

Step B: Preparation of (2-chloro-4-fluorophenyl)[5-(2,6-difluoro-4-hydroxyphenyl)-1,3-dimethyl-1H-pyrazol-4-yl]methanone To a mixture of (2-chloro-4-fluorophenyl)[5-[2,6-difluoro-4-(4,4,5,5-tetramethyl-1,3,2-dioxaborolan-2-yl)phenyl]-1,3-dimethyl-1H-pyrazol-4-yl]methanone (i.e. the product of Step A) (0.25 g, 0.51 mmol) in dichloromethane (7 ml) was added N,N,4-trimethylbenzenamine N-oxide (prepared according to Organic Letters 2012, 14, 3494-3497) (0.092 g, 0.61 mmol). After 3 h, the reaction mixture was diluted with water and extracted with dichloromethane. The combined organic layers were dried over sodium sulfate, filtered and concentrated under reduced pressure. The resulting material was purified by column chromatography on silica gel eluting with 30% ethyl acetate in petroleum ether to provide the title compound as an off-white solid (0.060 g).
$^1$H NMR (DMSO-d$_6$): δ 10.73 (s, 1H), 7.28-7.18 (m, 2H), 7.10-7.08 (m, 1H), 6.35 (d, 2H), 3.57 (s, 3H), 2.35 (s, 3H).

Step C: Preparation of (2-chloro-4-fluorophenyl)[5-[4-(cyclopropylmethoxy)-2,6-difluorophenyl]-1,3-dimethyl-1H-pyrazol-4-yl]methanone To a mixture of (2-chloro-4-fluorophenyl)[5-(2,6-difluoro-4-hydroxyphenyl)-1,3-dimethyl-1H-pyrazol-4-yl]methanone (i.e. the product of Step B) (0.090 g, 0.24 mmol) and potassium carbonate (0.065 g, 0.44 mmol) in N,N-dimethylformamide (2 ml) was added (iodomethyl)cyclopropane (0.051 g, 0.28 mmol). After 5 h, the reaction mixture was diluted with water and extracted with ethyl acetate (2×50 mL). The combined organic layers were dried over sodium sulfate, filtered and concentrated under reduced pressure. The resulting material was purified by column chromatography on silica gel eluting with 30% ethyl acetate in petroleum ether to provide the title compound as an off-white solid (0.087 g).

$^1$H NMR (DMSO-$d_6$): δ 7.28-7.23 (m, 2H), 7.07 (dt, 1H), 6.66 (d, 2H), 3.82 (d, 2H), 3.58 (s, 3H), 2.34 (s, 3H), 1.21-1.17 (m, 1H), 0.62-0.56 (m, 2H), 0.33-0.28 (m, 2H).

Step D: Preparation of α-(2-chloro-4-fluorophenyl)-5-[4-(cyclopropylmethoxy)-2,6-difluorophenyl]-1,3-dimethyl-1H-pyrazole-4-methanol To a mixture of (2-chloro-4-fluorophenyl)[5-[4-(cyclopropylmethoxy)-2,6-difluorophenyl]-1,3-dimethyl-1H-pyrazol-4-yl]methanone (i.e. the product of Step C) (0.20 g, 0.46 mmol) in methanol (3 ml) was added sodium borohydride (0.052 g, 1.4 mmol). After stirring for 5 h, the reaction was quenched with ice water and then the methanol was removed under reduced pressure. The resulting mixture was extracted with ethyl acetate (2×25 mL) and the combined organic layers were dried over sodium sulfate, filtered and concentrated under reduced pressure. The resulting material was purified by preparative TLC (GF 254, preparative silica gel plate) eluting with 20% ethyl acetate in petroleum ether to provide the title compound, a product of the present invention, as an off-white solid (0.10 g).

$^1$H NMR (DMSO-$d_6$): δ 7.45-7.40 (m, 1H), 7.16 (dd, 1H), 6.94 (dt, 1H), 6.75 (d, 1H), 6.61 (d, 1H), 5.66-5.62 (m, 2H), 3.86 (d, 2H), 3.42 (s, 3H), 2.15 (s, 3H), 1.26-1.21 (m, 1H), 0.63-0.57 (m, 2H), 0.36-0.31 (m, 2H).

Example 3

Preparation of α-(2-chloro-4-fluorophenyl)-5-[2,6-difluoro-4-(3-methylbutoxy)phenyl]-1,3-dimethyl-1H-pyrazole-4-methanol (Compound 9)

Step A: Preparation of (2-chloro-4-fluorophenyl)[5-[2,6-difluoro-4-(3-methylbutoxy)phenyl]-1,3-dimethyl-1H-pyrazol-4-yl]methanone To a mixture of (2-chloro-4-fluorophenyl)[5-(2,6-difluoro-4-hydroxyphenyl)-1,3-dimethyl-1H-pyrazol-4-yl]methanone (i.e. the product of Example 2, Step B) (0.066 g, 0.17 mmol) and potassium carbonate (0.047 g, 0.35 mmol) in N,N-dimethylformamide (2 ml) was added 1-iodo-3-methylbutane (0.030 ml, 0.21 mmol). After 5 h, the reaction mixture was diluted with water and extracted with ethyl acetate (2×50 mL). The combined organic layers were dried over sodium sulfate, filtered and concentrated under reduced pressure. The resulting material was purified by column chromatography on silica gel eluting with 30% ethyl acetate in petroleum ether to provide the title compound as an off-white solid (50 mg).

$^1$H NMR (CDCl$_3$): δ 7.23-7.19 (m, 1H), 6.87 (dd, 1H), 6.82-6.77 (m, 1H), 6.30 (d, 2H), 3.91 (t, 2H), 3.65 (s, 3H), 2.46 (s, 3H), 1.82-1.77 (m, 1H), 1.68-1.63 (m, 2H), 0.97 (d, 6H).

Step B: Preparation of α-(2-chloro-4-fluorophenyl)-5-[2,6-difluoro-4-(3-methylbutoxy)phenyl]-1,3-dimethyl-1H-pyrazole-4-methanol To mixture of (2-chloro-4-fluorophenyl)[5-[2,6-difluoro-4-(3-methylbutoxy)phenyl]-1,3-dimethyl-1H-pyrazol-4-yl]methanone (i.e. the product of Step A) (0.05 g, 0.111 mmol) in methanol (2 ml) was added sodium borohydride (0.0080 g, 0.22 mmol). After 5 h, the reaction mixture was quenched with ice water and then the methanol was removed under reduced pressure. The resulting mixture was extracted with ethyl acetate (2×25 mL) and the combined organic layers were dried over sodium sulfate, filtered and concentrated under reduced pressure. The resulting material was purified by preparative TLC (GF 254, preparative silica gel plate) eluting with 20% ethyl acetate in petroleum ether to provide the title compound, a product of the present invention, as an off-white solid (30 mg).

$^1$H NMR (DMSO-d6): δ 7.44-7.41 (m, 1H), 7.15 (d, 1H), 6.91 (t, 1H), 6.75 (d, 1H), 6.60 (d, 1H), 5.67 (d, 1H), 5.61 (d, 1H), 4.06-4.00 (m, 2H), 3.41 (s, 3H), 2.16 (s, 3H), 1.81-1.74 (m, 1H), 1.64-1.59 (m, 2H), 0.94 (d, 6H).

By the procedures described herein together with methods known in the art, the compounds disclosed in the Tables that follow can be prepared. The following abbreviations are used in the Tables which follow: i means iso, c means cyclo, n means normal, s means secondary, Me means methyl, Bu means butyl, Pr means propyl, MeO means methoxy, CN means cyano, and Ph means phenyl.

TABLE 1

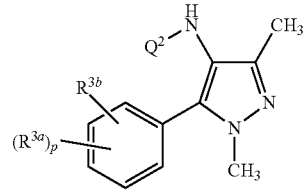

$Q^2$ is 2,4,6-tri-F—Ph, $(R^{3a})_p$ is 2,6-di-F.

| $R^{3b}$ | $R^{3b}$ | $R^{3b}$ | $R^{3b}$ |
|---|---|---|---|
| 4-(HC≡CCH$_2$O)— | 4-(MeC≡CCH$_2$O)— | 4-(HC≡CCH$_2$CH$_2$O)— | 4-(MeC≡CCH$_2$CH$_2$O)— |
| 4-(H$_2$C═CHCH$_2$O)— | 4-(MeHC═CCH$_2$O)— | 4-(ClHC═CHCH$_2$O)— | 4-(Cl$_2$C═CHCH$_2$O)— |
| 4-(HC═C(Me)CHO)— | 4-(H$_2$C═C(Me)CHO)— | 4-(H$_2$C═CHCH(Me)O)— | 4-(MeHC═CHCH(Me)O)— |
| 4-n-butoxy | 4-i-butoxy | 4-s-butoxy | 4-n-pentoxy |
| 4-i-pentoxy | 4-s-pentoxy | 4-(c-Pr—HC═CHCH$_2$O)- | 4-(c-Pr—C≡CCH$_2$O)— |
| 4-(c-Pr—HC═CH)— | 4-(c-Pr—C≡C)— | 4-(c-Pr—CH$_2$O)— | 4-(c-Bu—CH$_2$O)— |
| 4-(c-pentyl—CH$_2$O)— | 4-(HO—N═CH)— | 4-(MeO—N═CH)— | 4-(HO—N═C(Me))— |
| 4-(MeO—N═C(Me))— | 4-(MeHC═N—O)— | 4-(Me$_2$C═N—O)— | 4-(H$_2$C═N—O)— |
| 4-(H$_2$N—N═CH)— | 4-(MeNH—N═CH)— | 4-(Me$_2$N—N═CH)— | 4-(H$_2$N—N═C(Me))— |

TABLE 1-continued

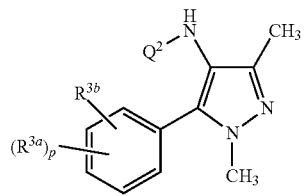

$Q^2$ is 2,4,6-tri-F—Ph, $(R^{3a})_p$ is 2,6-di-F.

| $R^{3b}$ | $R^{3b}$ | $R^{3b}$ | $R^{3b}$ |
|---|---|---|---|
| 4-(MeNH—N═C(Me))— | 4-(Me₂N—N═C(Me))— | 4-(MeHC═N—NH)— | 4-(Me₂C═N—NH)— |
| 4-(H₂C═N—NH)— | 4-(MeHC═N—N(Me))— | 4-(Me₂C═N—N(Me))— | 4-(H₂C═N—N(Me))— |
| 3-(HC≡CCH₂O)— | 3-(MeC≡CCH₂O)— | 3-(HC≡CCH₂CH₂O)— | 3-(MeC≡CCH₂CH₂O)— |
| 3-(H₂C═CHCH₂O)— | 3-(MeHC═CHCH₂O)— | 3-(ClHC═CHCH₂O)— | 3-(Cl₂C═CHCH₂O)— |
| 3-(HC═C(Me)CHO)— | 3-(H₂C═C(Me)CHO)— | 3-(H₂C═CHCH(Me)O)— | 3-(MeHC═CHCH(Me)O)— |
| 3-n-butoxy | 3-i-butoxy | 3-s-butoxy | 3-n-pentoxy |
| 3-i-pentoxy | 3-s-pentoxy | 3-(c-Pr—HC═CH₂O)— | 3-(c-Pr—C≡CCH₂O)— |
| 3-(c-Pr—HC═CH)— | 3-(c-Pr—C≡C)— | 3-(c-Pr—CH₂O)— | 3-(c-Bu—CH₂O)— |
| 3-(c-pentyl—CH₂O)— | 3-(HO—N═CH)— | 3-(MeO—N═CH)— | 3-(HO—N═C(Me))— |
| 3-(MeO—N═C(Me))— | 3-(MeHC═N—O)— | 3-(Me₂C═N—O)— | 3-(H₂C═N—O)— |
| 3-(H₂N—N═CH)— | 3-(MeNH—N═CH)— | 3-(MeHC═N—N(Me))— | 3-(H₂N—N═C(Me))— |
| 3-(MeNH—N═C(Me))— | 3-(Me₂N—N═C(Me))— | 3-(MeHC═N—NH)— | 3-(Me₂C═N—NH)— |
| 3-(H₂C═N—NH)— | 3-(MeHC═N—N(Me))— | 3-(Me₂C═N—N(Me))— | 3-(H₂C═N—N(Me))— |
| 3-CF₃-1H-pyrazol-1-yl | 3-Me-1H-pyrazol-1-yl | 3-F-1H-pyrazol-1-yl | 3-Br-1H-pyrazol-1-yl |
| 4-CF₃-1H-pyrazol-1-yl | 4-Me-1H-pyrazol-1-yl | 4-F-1H-pyrazol-1-yl | 4-Br-1H-pyrazol-1-yl |
| 5-CF₃-1H-pyrazol-1-yl | 5-Me-1H-pyrazol-1-yl | 5-F-1H-pyrazol-1-yl | 5-Br-1H-pyrazol-1-yl |
| 3-CHF₂-1H-pyrazol-1-yl | 3-Et-1H-pyrazol-1-yl | 3-Cl-1H-pyrazol-1-yl | 3-I-1H-pyrazol-1-yl |
| 4-CHF₂-1H-pyrazol-1-yl | 3-Et-1H-pyrazol-1-yl | 4-Cl-1H-pyrazol-1-yl | 4-I-1H-pyrazol-1-yl |
| 5-CHF₂-1H-pyrazol-1-yl | 3-Et-1H-pyrazol-1-yl | 5-Cl-1H-pyrazol-1-yl | 5-I-pyrazol-1-yl |
| 1H-pyrazol-1-yl | 1H-1,2,3-triazol-1-yl | 1H-1,2,3-triazol-1-yl | 1H-1,2,3-triazol-2-yl |
| 1H-pyrrol-1-yl | 1-Me-1H-pyrazol-3-yl | 1-CF₃-1H-pyrazol-3-yl | |

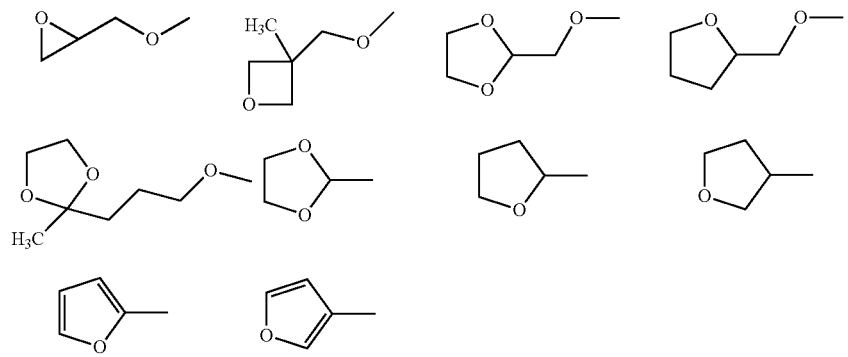

The present disclosure also includes Tables 1A through 215A, each of which is constructed the same as Table 1 above, except that the row heading in Table 1 (i.e. "$Q^2$ is 2,4,6-tri-F-Ph, $(R^{3a})_p$ is 2,6-di-F") is replaced with the respective row headings shown below. For Example, in Table 1A the row heading is "$Q^2$ is 2,4,6-tri-F-Ph, $(R^{3a})_p$ is 2-F", and $R^{3b}$ is as defined in Table 1 above. Thus, the first entry in Table 1A specifically discloses 5-[2-fluoro-4-(-propyn-1-yloxy)phenyl]-1,3-dimethyl-N-(2,4,6-trifluorophenyl)-1H-pyrazol-4-amine. Tables 2A through 215A are constructed similarly.

| Table | Row Heading |
|---|---|
| 1A | $Q^2$ is 2,4,6-tri-F—Ph, $(R^{3a})_p$ is 2-F. |
| 2A | $Q^2$ is 2,4,6-tri-F—Ph, $(R^{3a})_p$ is 2-Cl. |
| 3A | $Q^2$ is 2,4,6-tri-F—Ph, $(R^{3a})_p$ is 2-Br. |
| 4A | $Q^2$ is 2,4,6-tri-F—Ph, $(R^{3a})_p$ is 2-Me. |
| 5A | $Q^2$ is 2,4,6-tri-F—Ph, $(R^{3a})_p$ is 2-F, 6-Cl. |
| 6A | $Q^2$ is 2,4,6-tri-F—Ph, $(R^{3a})_p$ is 2-Cl, 6-F. |
| 7A | $Q^2$ is 2,4,6-tri-F—Ph, $(R^{3a})_p$ is 2,6-di-Cl. |
| 8A | $Q^2$ is 2,6-di-F—Ph, $(R^{3a})_p$ is 2,6-di-F. |
| 9A | $Q^2$ is 2,6-di-F—Ph, $(R^{3a})_p$ is 2-F. |
| 10A | $Q^2$ is 2,6-di-F—Ph, $(R^{3a})_p$ is 2-Cl. |
| 11A | $Q^2$ is 2,6-di-F—Ph, $(R^{3a})_p$ is 2-Br. |
| 12A | $Q^2$ is 2,6-di-F—Ph, $(R^{3a})_p$ is 2-Me. |
| 13A | $Q^2$ is 2,6-di-F—Ph, $(R^{3a})_p$ is 2-F, 6-Cl. |
| 14A | $Q^2$ is 2,6-di-F—Ph, $(R^{3a})_p$ is 2-Cl, 6-F. |
| 15A | $Q^2$ is 2,6-di-F—Ph, $(R^{3a})_p$ is 2,6-di-Cl. |
| 16A | $Q^2$ is 2,6-di-F-4-MeO—Ph, $(R^{3a})_p$ is 2,6-di-F. |
| 17A | $Q^2$ is 2,6-di-F-4-MeO—Ph, $(R^{3a})_p$ is 2-F. |
| 18A | $Q^2$ is 2,6-di-F-4-MeO—Ph, $(R^{3a})_p$ is 2-Cl. |
| 19A | $Q^2$ is 2,6-di-F-4-MeO—Ph, $(R^{3a})_p$ is 2-Br. |
| 20A | $Q^2$ is 2,6-di-F-4-MeO—Ph, $(R^{3a})_p$ is 2-Me. |
| 21A | $Q^2$ is 2,6-di-F-4-MeO—Ph, $(R^{3a})_p$ is 2-F, 6-Cl. |
| 22A | $Q^2$ is 2,6-di-F-4-MeO—Ph, $(R^{3a})_p$ is 2-Cl, 6-F. |
| 23A | $Q^2$ is 2,6-di-F-4-MeO—Ph, $(R^{3a})_p$ is 2,6-di-Cl. |
| 24A | $Q^2$ is 2,6-di-F-4-Me—Ph, $(R^{3a})_p$ is 2,6-di-F. |
| 25A | $Q^2$ is 2,6-di-F-4-Me—Ph, $(R^{3a})_p$ is 2-F. |
| 26A | $Q^2$ is 2,6-di-F-4-Me—Ph, $(R^{3a})_p$ is 2-Cl. |

| Table | Row Heading |
|---|---|
| 27A | $Q^2$ is 2,6-di-F-4-Me—Ph, $(R^{3a})_p$ is 2-Br. |
| 28A | $Q^2$ is 2,6-di-F-4-Me—Ph, $(R^{3a})_p$ is 2-Me. |
| 29A | $Q^2$ is 2,6-di-F-4-Me—Ph, $(R^{3a})_p$ is 2-F, 6-Cl |
| 30A | $Q^2$ is 2,6-di-F-4-Me—Ph, $(R^{3a})_p$ is 2-Cl, 6-F. |
| 31A | $Q^2$ is 2,6-di-F-4-Me—Ph, $(R^{3a})_p$ is 2,6-di-Cl. |
| 32A | $Q^2$ is 2,6-di-F-4-CN—Ph, $(R^{3a})_p$ is 2,6-di-F. |
| 33A | $Q^2$ is 2,6-di-F-4-CN—Ph, $(R^{3a})_p$ is 2-F. |
| 34A | $Q^2$ is 2,6-di-F-4-CN—Ph, $(R^{3a})_p$ is 2-Cl. |
| 35A | $Q^2$ is 2,6-di-F-4-CN—Ph, $(R^{3a})_p$ is 2-Br. |
| 36A | $Q^2$ is 2,6-di-F-4-CN—Ph, $(R^{3a})_p$ is 2-Me. |
| 37A | $Q^2$ is 2,6-di-F-4-CN—Ph, $(R^{3a})_p$ is 2-F, 6-Cl. |
| 38A | $Q^2$ is 2,6-di-F-4-CN—Ph, $(R^{3a})_p$ is 2-Cl, 6-F. |
| 39A | $Q^2$ is 2,6-di-F-4-CN—Ph, $(R^{3a})_p$ is 2,6-di-Cl. |
| 40A | $Q^2$ is 2,6-di-F-4-Cl—Ph, $(R^{3a})_p$ is 2,6-di-F. |
| 41A | $Q^2$ is 2,6-di-F-4-Cl—Ph, $(R^{3a})_p$ is 2-F. |
| 42A | $Q^2$ is 2,6-di-F-4-Cl—Ph, $(R^{3a})_p$ is 2-Cl. |
| 43A | $Q^2$ is 2,6-di-F-4-Cl—Ph, $(R^{3a})_p$ is 2-Br. |
| 44A | $Q^2$ is 2,6-di-F-4-Cl—Ph, $(R^{3a})_p$ is 2-Me. |
| 45A | $Q^2$ is 2,6-di-F-4-Cl—Ph, $(R^{3a})_p$ is 2-F, 6-Cl. |
| 46A | $Q^2$ is 2,6-di-F-4-Cl—Ph, $(R^{3a})_p$ is 2-Cl, 6-F. |
| 47A | $Q^2$ is 2,6-di-F-4-Cl—Ph, $(R^{3a})_p$ is 2,6-di-Cl. |
| 48A | $Q^2$ is 2,6-di-F-4-Br—Ph, $(R^{3a})_p$ is 2,6-di-F. |
| 49A | $Q^2$ is 2,6-di-F-4-Br—Ph, $(R^{3a})_p$ is 2-F. |
| 50A | $Q^2$ is 2,6-di-F-4-Br—Ph, $(R^{3a})_p$ is 2-Cl. |
| 51A | $Q^2$ is 2,6-di-F-4-Br—Ph, $(R^{3a})_p$ is 2-Br. |
| 52A | $Q^2$ is 2,6-di-F-4-Br—Ph, $(R^{3a})_p$ is 2-Me. |
| 53A | $Q^2$ is 2,6-di-F-4-Br—Ph, $(R^{3a})_p$ is 2-F, 6-Cl. |
| 54A | $Q^2$ is 2,6-di-F-4-Br—Ph, $(R^{3a})_p$ is 2-Cl, 6-F. |
| 55A | $Q^2$ is 2,6-di-F-4-Br—Ph, $(R^{3a})_p$ is 2,6-di-Cl. |
| 56A | $Q^2$ is 2,4-di-F—Ph, $(R^{3a})_p$ is 2,6-di-F. |
| 57A | $Q^2$ is 2,4-di-F—Ph, $(R^{3a})_p$ is 2-F. |
| 58A | $Q^2$ is 2,4-di-F—Ph, $(R^{3a})_p$ is 2-Cl. |
| 59A | $Q^2$ is 2,4-di-F—Ph, $(R^{3a})_p$ is 2-Br. |
| 60A | $Q^2$ is 2,4-di-F—Ph, $(R^{3a})_p$ is 2-Me |
| 61A | $Q^2$ is 2,4-di-F—Ph, $(R^{3a})_p$ is 2-F, 6-Cl. |
| 62A | $Q^2$ is 2,4-di-F—Ph, $(R^{3a})_p$ is 2-Cl, 6-F. |
| 63A | $Q^2$ is 2,4-di-F—Ph, $(R^{3a})_p$ is 2,6-di-Cl |
| 64A | $Q^2$ is 2,4-di-F-6-Cl—Ph, $(R^{3a})_p$ is 2,6-di-F. |
| 65A | $Q^2$ is 2,4-di-F-6-Cl—Ph, $(R^{3a})_p$ is 2-F. |
| 66A | $Q^2$ is 2,4-di-F-6-Cl—Ph, $(R^{3a})_p$ is 2-Cl. |
| 67A | $Q^2$ is 2,4-di-F-6-Cl—Ph, $(R^{3a})_p$ is 2-Br. |
| 68A | $Q^2$ is 2,4-di-F-6-Cl—Ph, $(R^{3a})_p$ is 2-Me. |
| 69A | $Q^2$ is 2,4-di-F-6-Cl—Ph, $(R^{3a})_p$ is 2-F, 6-Cl. |
| 70A | $Q^2$ is 2,4-di-F-6-Cl—Ph, $(R^{3a})_p$ is 2-Cl, 6-F. |
| 71A | $Q^2$ is 2,4-di-F-6-Cl—Ph, $(R^{3a})_p$ is 2,6-di-Cl. |
| 72A | $Q^2$ is 2,4-di-F-6-Br—Ph, $(R^{3a})_p$ is 2,6-di-F |
| 73A | $Q^2$ is 2,4-di-F-6-Br—Ph, $(R^{3a})_p$ is 2-F. |
| 74A | $Q^2$ is 2,4-di-F-6-Br—Ph, $(R^{3a})_p$ is 2-Cl. |
| 75A | $Q^2$ is 2,4-di-F-6-Br—Ph, $(R^{3a})_p$ is 2-Br. |
| 76A | $Q^2$ is 2,4-di-F-6-Br—Ph, $(R^{3a})_p$ is 2-Me. |
| 77A | $Q^2$ is 2,4-di-F-6-Br—Ph, $(R^{3a})_p$ is 2-F, 6-Cl. |
| 78A | $Q^2$ is 2,4-di-F-6-Br—Ph, $(R^{3a})_p$ is 2-Cl, 6-F. |
| 79A | $Q^2$ is 2,4-di-F-6-Br—Ph, $(R^{3a})_p$ is 2,6-di-Cl. |
| 80A | $Q^2$ is 2-Cl-4-Me-6-F—Ph, $(R^{3a})_p$ is 2,6-di-F. |
| 81A | $Q^2$ is 2-Cl-4-Me-6-F—Ph, $(R^{3a})_p$ is 2-F. |
| 82A | $Q^2$ is 2-Cl-4-Me-6-F—Ph, $(R^{3a})_p$ is 2-Cl. |
| 83A | $Q^2$ is 2-Cl-4-Me-6-F—Ph, $(R^{3a})_p$ is 2-Br. |
| 84A | $Q^2$ is 2-Cl-4-Me-6-F—Ph, $(R^{3a})_p$ is 2-Me. |
| 85A | $Q^2$ is 2-Cl-4-Me-6-F—Ph, $(R^{3a})_p$ is 2-F, 6-Cl. |
| 86A | $Q^2$ is 2-Cl-4-Me-6-F—Ph, $(R^{3a})_p$ is 2-Cl, 6-F. |
| 87A | $Q^2$ is 2-Cl-4-Me-6-F—Ph, $(R^{3a})_p$ is 2,6-di-Cl. |
| 88A | $Q^2$ is 2-Cl-4-MeO-6-F—Ph, $(R^{3a})_p$ is 2,6-di-F. |
| 89A | $Q^2$ is 2-Cl-4-MeO-6-F—Ph, $(R^{3a})_p$ is 2-F. |
| 90A | $Q^2$ is 2-Cl-4-MeO-6-F—Ph, $(R^{3a})_p$ is 2-Cl. |
| 91A | $Q^2$ is 2-Cl-4-MeO-6-F—Ph, $(R^{3a})_p$ is 2-Br. |
| 92A | $Q^2$ is 2-Cl-4-MeO-6-F—Ph, $(R^{3a})_p$ is 2-Me. |
| 93A | $Q^2$ is 2-Cl-4-MeO-6-F—Ph, $(R^{3a})_p$ is 2-F, 6-Cl. |
| 94A | $Q^2$ is 2-Cl-4-MeO-6-F—Ph, $(R^{3a})_p$ is 2-Cl, 6-F. |
| 95A | $Q^2$ is 2-Cl-4-MeO-6-F—Ph, $(R^{3a})_p$ is 2,6-di-Cl. |
| 96A | $Q^2$ is 2-Br-4-Me-6-F—Ph, $(R^{3a})_p$ is 2,6-di-F. |
| 97A | $Q^2$ is 2-Br-4-Me-6-F—Ph, $(R^{3a})_p$ is 2-F. |
| 98A | $Q^2$ is 2-Br-4-Me-6-F—Ph, $(R^{3a})_p$ is 2-Cl. |
| 99A | $Q^2$ is 2-Br-4-Me-6-F—Ph, $(R^{3a})_p$ is 2-Br. |
| 100A | $Q^2$ is 2-Br-4-Me-6-F—Ph, $(R^{3a})_p$ is 2-Me |
| 101A | $Q^2$ is 2-Br-4-Me-6-F—Ph, $(R^{3a})_p$ is 2-F, 6-Cl. |
| 102A | $Q^2$ is 2-Br-4-Me-6-F—Ph, $(R^{3a})_p$ is 2-Cl, 6-F. |
| 103A | $Q^2$ is 2-Br-4-Me-6-F—Ph, $(R^{3a})_p$ is 2,6-di-Cl. |
| 104A | $Q^2$ is 2-Br-4-MeO-6-F—Ph, $(R^{3a})_p$ is 2,6-di-F. |
| 105A | $Q^2$ is 2-Br-4-MeO-6-F—Ph, $(R^{3a})_p$ is 2-F. |
| 106A | $Q^2$ is 2-Br-4-MeO-6-F—Ph, $(R^{3a})_p$ is 2-Cl. |
| 107A | $Q^2$ is 2-Br-4-MeO-6-F—Ph, $(R^{3a})_p$ is 2-Br. |
| 108A | $Q^2$ is 2-Br-4-MeO-6-F—Ph, $(R^{3a})_p$ is 2-Me. |
| 109A | $Q^2$ is 2-Br-4-MeO-6-F—Ph, $(R^{3a})_p$ is 2-F, 6-Cl. |
| 110A | $Q^2$ is 2-Br-4-MeO-6-F—Ph, $(R^{3a})_p$ is 2-Cl, 6-F. |
| 111A | $Q^2$ is 2-Br-4-MeO-6-F—Ph, $(R^{3a})_p$ is 2,6-di-Cl. |
| 112A | $Q^2$ is 2,6-di-Cl-4-Me—Ph, $(R^{3a})_p$ is 2,6-di-F. |
| 113A | $Q^2$ is 2,6-di-Cl-4-Me—Ph, $(R^{3a})_p$ is 2-F. |
| 114A | $Q^2$ is 2,6-di-Cl-4-Me—Ph, $(R^{3a})_p$ is 2-Br. |
| 115A | $Q^2$ is 2,6-di-Cl-4-Me—Ph, $(R^{3a})_p$ is 2-Me. |
| 116A | $Q^2$ is 2,6-di-Cl-4-Me—Ph, $(R^{3a})_p$ is 2-F, 6-Cl |
| 117A | $Q^2$ is 2,6-di-Cl-4-Me—Ph, $(R^{3a})_p$ is 2-Cl, 6-F. |
| 118A | $Q^2$ is 2,6-di-Cl-4-Me—Ph, $(R^{3a})_p$ is 2,6-di-Cl. |
| 119A | $Q^2$ is 2,6-di-Br-4-Me—Ph, $(R^{3a})_p$ is 2,6-di-F. |
| 120A | $Q^2$ is 2,6-di-Br-4-Me—Ph, $(R^{3a})_p$ is 2-F. |
| 121A | $Q^2$ is 2,6-di-Br-4-Me—Ph, $(R^{3a})_p$ is 2-Cl. |
| 122A | $Q^2$ is 2,6-di-Br-4-Me—Ph, $(R^{3a})_p$ is 2-Br. |
| 123A | $Q^2$ is 2,6-di-Br-4-Me—Ph, $(R^{3a})_p$ is 2-Me. |
| 124A | $Q^2$ is 2,6-di-Br-4-Me—Ph, $(R^{3a})_p$ is 2-F, 6-Cl. |
| 125A | $Q^2$ is 2,6-di-Br-4-Me—Ph, $(R^{3a})_p$ is 2-Cl, 6-F. |
| 126A | $Q^2$ is 2,6-di-Br-4-Me—Ph, $(R^{3a})_p$ is 2,6-di-Cl. |
| 127A | $Q^2$ is 2,4,6-tri-Cl—Ph, $(R^{3a})_p$ is 2,6-di-F. |
| 128A | $Q^2$ is 2,4,6-tri-Cl—Ph, $(R^{3a})_p$ is 2-F. |
| 129A | $Q^2$ is 2,4,6-tri-Cl—Ph, $(R^{3a})_p$ is 2-Cl. |
| 130A | $Q^2$ is 2,4,6-tri-Cl—Ph, $(R^{3a})_p$ is 2-Br. |
| 131A | $Q^2$ is 2,4,6-tri-Cl—Ph, $(R^{3a})_p$ is 2-Me. |
| 132A | $Q^2$ is 2,4,6-tri-Cl—Ph, $(R^{3a})_p$ is 2-F, 6-Cl. |
| 133A | $Q^2$ is 2,4,6-tri-Cl—Ph, $(R^{3a})_p$ is 2-Cl, 6-F. |
| 134A | $Q^2$ is 2,4,6-tri-Cl—Ph, $(R^{3a})_p$ is 2,6-di-Cl. |
| 135A | $Q^2$ is 2-Cl-4-F, $(R^{3a})_p$ is 2,6-di-F. |
| 136A | $Q^2$ is 2-Cl-4-F, $(R^{3a})_p$ is 2-F. |
| 137A | $Q^2$ is 2-Cl-4-F, $(R^{3a})_p$ is 2-Cl. |
| 138A | $Q^2$ is 2-Cl-4-F, $(R^{3a})_p$ is 2-Br. |
| 139A | $Q^2$ is 2-Cl-4-F, $(R^{3a})_p$ is 2-Me. |
| 140A | $Q^2$ is 2-Cl-4-F, $(R^{3a})_p$ is 2-F, 6-Cl |
| 141A | $Q^2$ is 2-Cl-4-F, $(R^{3a})_p$ is 2-Cl, 6-F |
| 142A | $Q^2$ is 2-Cl-4-F, $(R^{3a})_p$ is 2,6-di-Cl. |
| 143A | $Q^2$ is 2-Cl-4-Me, $(R^{3a})_p$ is 2,6-di-F. |
| 144A | $Q^2$ is 2-Cl-4-Me, $(R^{3a})_p$ is 2-F. |
| 145A | $Q^2$ is 2-Cl-4-Me, $(R^{3a})_p$ is 2-Cl. |
| 146A | $Q^2$ is 2-Cl-4-Me, $(R^{3a})_p$ is 2-Br. |
| 147A | $Q^2$ is 2-Cl-4-Me, $(R^{3a})_p$ is 2-Me. |
| 148A | $Q^2$ is 2-Cl-4-Me, $(R^{3a})_p$ is 2-F, 6-Cl. |
| 149A | $Q^2$ is 2-Cl-4-Me, $(R^{3a})_p$ is 2-Cl, 6-F. |
| 150A | $Q^2$ is 2-Cl-4-Me, $(R^{3a})_p$ is 2,6-di-Cl. |
| 151A | $Q^2$ is 2-Cl-4-MeO, $(R^{5a})_p$ is 2,6-di-F. |
| 152A | $Q^2$ is 2-Cl-4-MeO, $(R^{3a})_p$ is 2-F |
| 153A | $Q^2$ is 2-Cl-4-MeO, $(R^{3a})_p$ is 2-Cl. |
| 154A | $Q^2$ is 2-Cl-4-MeO, $(R^{3a})_p$ is 2-Br. |
| 155A | $Q^2$ is 2-Cl-4-MeO, $(R^{3a})_p$ is 2-Me . . . |
| 156A | $Q^2$ is 2-Cl-4-MeO, $(R^{3a})_p$ is 2-F, 6-Cl. |
| 157A | $Q^2$ is 2-Cl-4-MeO, $(R^{3a})_p$ is 2-Cl, 6-F. |
| 158A | $Q^2$ is 2-Cl-4-MeO, $(R^{3a})_p$ is 2,6-di-Cl. |
| 159A | $Q^2$ is 2-Br-4-F, $(R^{3a})_p$ is 2,6-di-F. |
| 160A | $Q^2$ is 2-Br-4-F, $(R^{3a})_p$ is 2-F. |
| 161A | $Q^2$ is 2-Br-4-F, $(R^{3a})_p$ is 2-Cl. |
| 162A | $Q^2$ is 2-Br-4-F, $(R^{3a})_p$ is 2-Br. |
| 163A | $Q^2$ is 2-Br-4-F, $(R^{3a})_p$ is 2-Me. |
| 164A | $Q^2$ is 2-Br-4-F, $(R^{3a})_p$ is 2-F, 6-Cl. |
| 165A | $Q^2$ is 2-Br-4-F, $(R^{3a})_p$ is 2-Cl, 6-F. |
| 166A | $Q^2$ is 2-Br-4-F, $(R^{3a})_p$ is 2,6-di-Cl. |
| 167A | $Q^2$ is 2-Br-4-Me, $(R^{3a})_p$ is 2,6-di-F. |
| 168A | $Q^2$ is 2-Br-4-Me, $(R^{3a})_p$ is 2-F. |
| 169A | $Q^2$ is 2-Br-4-Me, $(R^{3a})_p$ is 2-Cl. |
| 170A | $Q^2$ is 2-Br-4-Me, $(R^{3a})_p$ is 2-Br. |
| 171A | $Q^2$ is 2-Br-4-Me, $(R^{3a})_p$ is 2-Me. |
| 172A | $Q^2$ is 2-Br-4-Me, $(R^{3a})_p$ is 2-F, 6-Cl. |
| 173A | $Q^2$ is 2-Br-4-Me, $(R^{3a})_p$ is 2-Cl, 6-F. |
| 174A | $Q^2$ is 2-Br-4-Me, $(R^{3a})_p$ is 2,6-di-Cl. |
| 175A | $Q^2$ is 2-Br-4-MeO, $(R^{3a})_p$ is 2,6-di-F. |
| 176A | $Q^2$ is 2-Br-4-MeO, $(R^{3a})_p$ is 2-F. |
| 177A | $Q^2$ is 2-Br-4-MeO, $(R^{3a})_p$ is 2-Cl. |
| 178A | $Q^2$ is 2-Br-4-MeO, $(R^{3a})_p$ is 2-Br. |
| 179A | $Q^2$ is 2-Br-4-MeO, $(R^{3a})_p$ is 2-Me. |
| 180A | |

-continued

| Table | Row Heading |
|---|---|
| 181A | Q² is 2-Br-4-MeO, (R³ᵃ)ₚ is 2-F, 6-Cl. |
| 182A | Q² is 2-Br-4-MeO, (R³ᵃ)ₚ is 2-Cl, 6-F. |
| 183A | Q² is 2-Br-4-MeO, (R³ᵃ)ₚ is 2,6-di-Cl. |
| 184A | Q² is 2,4-di-Cl, (R³ᵃ)ₚ is 2,6-di-F. |
| 185A | Q² is 2,4-di-Cl, (R³ᵃ)ₚ is 2-F. |
| 186A | Q² is 2,4-di-Cl, (R³ᵃ)ₚ is 2-Cl. |
| 187A | Q² is 2,4-di-Cl, (R³ᵃ)ₚ is 2-Br. |
| 188A | Q² is 2,4-di-Cl, (R³ᵃ)ₚ is 2-Me. |
| 189A | Q² is 2,4-di-Cl, (R³ᵃ)ₚ is 2-F, 6-Cl. |
| 190A | Q² is 2,4-di-Cl, (R³ᵃ)ₚ is 2-Cl, 6-F. |
| 191A | Q² is 2,4-di-Cl, (R³ᵃ)ₚ is 2,6-di-Cl. |
| 192A | Q² is 2,6-di-Cl, (R³ᵃ)ₚ is 2,6-di-F. |
| 193A | Q² is 2,6-di-Cl, (R³ᵃ)ₚ is 2-F. |
| 194A | Q² is 2,6-di-Cl, (R³ᵃ)ₚ is 2-Cl. |
| 195A | Q² is 2,6-di-Cl, (R³ᵃ)ₚ is 2-Br. |
| 196A | Q² is 2,6-di-Cl, (R³ᵃ)ₚ is 2-Me. |
| 197A | Q² is 2,6-di-Cl, (R³ᵃ)ₚ is 2-F, 6-Cl. |
| 198A | Q² is 2,6-di-Cl, (R³ᵃ)ₚ is 2-Cl, 6-F. |
| 199A | Q² is 2,6-di-Cl, (R³ᵃ)ₚ is 2,6-di-Cl. |
| 200A | Q² is 2,4-di-Me, (R³ᵃ)ₚ is 2,6-di-F. |
| 201A | Q² is 2,4-di-Me, (R³ᵃ)ₚ is 2-F. |
| 202A | Q² is 2,4-di-Me, (R³ᵃ)ₚ is 2-Cl. |
| 203A | Q² is 2,4-di-Me, (R³ᵃ)ₚ is 2-Br. |
| 204A | Q² is 2,4-di-Me, (R³ᵃ)ₚ is 2-Me. |
| 205A | Q² is 2,4-di-Me, (R³ᵃ)ₚ is 2-F, 6-Cl. |
| 206A | Q² is 2,4-di-Me, (R³ᵃ)ₚ is 2-Cl, 6-F. |
| 207A | Q² is 2,4-di-Me, (R³ᵃ)ₚ is 2,6-di-Cl. |
| 208A | Q² is 2,6-di-Me, (R³ᵃ)ₚ is 2,6-di-F. |
| 209A | Q² is 2,6-di-Me, (R³ᵃ)ₚ is 2-F. |
| 210A | Q² is 2,6-di-Me, (R³ᵃ)ₚ is 2-Cl |
| 211A | Q² is 2,6-di-Me, (R³ᵃ)ₚ is 2-Br. |
| 212A | Q² is 2,6-di-Me, (R³ᵃ)ₚ is 2-Me. |
| 213A | Q² is 2,6-di-Me, (R³ᵃ)ₚ is 2-F, 6-Cl. |
| 214A | Q² is 2,6-di-Me, (R³ᵃ)ₚ is 2-Cl, 6-F. |
| 215A | Q² is 2,6-di-Me, (R³ᵃ)ₚ is 2,6-di-Cl. |

TABLE 2

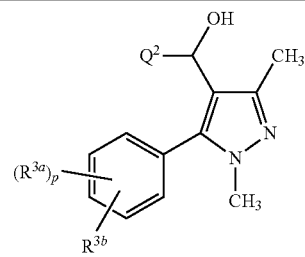

Q² is 2,4,6-tri-F—Ph, (R³ᵃ)ₚ is 2,6-di-F.

| R³ᵇ | R³ᵇ | R³ᵇ | R³ᵇ |
|---|---|---|---|
| 4-(HC≡CCH₂O)— | 4-(MeC≡CCH₂O)— | 4-(HC≡CCH₂CH₂O)— | 4-(MeC≡CCH₂CH₂O)— |
| 4-(H₂C=CHCH₂O)— | 4-(MeHC=CHCH₂O)— | 4-(ClHC=CHCH₂O)— | 4-(Cl₂C=CHCH₂O)— |
| 4-(HC=C(Me)CHO)— | 4-(H₂C=C(Me)CHO)— | 4-(H₂C=CHCH(Me)O)— | 4-(MeHC=CHCH(Me)O)— |
| 4-n-butoxy | 4-i-butoxy | 4-s-butoxy | 4-n-pentoxy |
| 4-i-pentoxy | 4-s-pentoxy | 4-(c-Pr—HC=CHCH₂O)— | 4-(c-Pr—C≡CCH₂O)— |
| 4-(c-Pr—HC=CH)— | 4-(c-Pr—C≡C)— | 4-(c-Pr—CH₂O)— | 4-(c-Bu—CH₂O)— |
| 4-(c-pentyl-CH₂O)— | 4-(HO—N=CH)— | 4-(MeO—N=CH)— | 4-(HO—N=C(Me))— |
| 4-(MeO—N=C(Me))— | 4-(MeHC=N—O)— | 4-(Me₂C=N—O)— | 4-(H₂C=N—O)— |
| 4-(H₂N—N=CH)— | 4-(MeNH—N=CH)— | 4-(Me₂N—N=CH)— | 4-(H₂N—N=C(Me))— |
| 4-(MeNH—N=C(Me))— | 4-(Me₂N—N=C(Me))— | 4-(MeHC=N—NH)— | 4-(Me₂C=N—NH)— |
| 4-(H₂C=N—NH)— | 4-(MeHC=N—N(Me))— | 4-(Me₂C=N—N(Me))— | 4-(H₂C=N—N(Me))— |
| 3-(HC≡CCH₂O)— | 3-(MeC≡CCH₂O)— | 3-(HC≡CCH₂CH₂O)— | 3-(MeC≡CCH₂CH₂O)— |
| 3-(H₂C=CHCH₂O)— | 3-(MeHC=CHCH₂O)— | 3-(ClHC=CHCH₂O)— | 3-(Cl₂C=CHCH₂O)— |
| 3-(HC=C(Me)CHO)— | 3-(H₂C=C(Me)CHO)— | 3-(H₂C=CHCH(Me)O)— | 3-(MeHC=CHCH(Me)O)— |
| 3-n-butoxy | 3-i-butoxy | 3-s-butoxy | 3-n-pentoxy |
| 3-i-pentoxy | 3-s-pentoxy | 3-(c-Pr—HC=CHCH₂O)— | 3-(c-Pr—C≡CCH₂O)— |
| 3-(c-Pr—HC=CH)— | 3-(c-Pr—C≡C)— | 3-(c-Pr—CH₂O)— | 3-(c-Bu—CH₂O)— |
| 3-(c-pentyl-CH₂O)— | 3-(HO—N=CH)— | 3-(MeO—N=CH)— | 3-(HO—N=C(Me))— |
| 3-(MeO—N=C(Me))— | 3-(MeHC=N—O)— | 3-(Me₂C=N—O)— | 3-(H₂C=N—O)— |
| 3-(H₂N—N=CH)— | 3-(MeNH—N=CH)— | 3-(Me₂N—N=CH)— | 3-(H₂N—N=C(Me))— |
| 3-(MeNH—N=C(Me))— | 3-(Me₂N—N=C(Me))— | 3-(MeHC=N—NH)— | 3-(Me₂C=N—NH)— |
| 3-(H₂C=N—NH)— | 3-(MeHC=N—N(Me))— | 3-(Me₂C=N—N(Me))— | 3-(H₂C=N—N(Me))— |
| 3-CF₃-1H-pyrazol-1-yl | 3-Me-1H-pyrazol-1-yl | 3-F-1H-pyrazol-1-yl | 3-Br-1H-pyrazol-1-yl |
| 4-CF₃-1H-pyrazol-1-yl | 4-Me-1H-pyrazol-1-yl | 4-F-1H-pyrazol-1-yl | 4-Br-1H-pyrazol-1-yl |
| 5-CF₃-1H-pyrazol-1-yl | 5-Me-1H-pyrazol-1-yl | 5-F-1H-pyrazol-1-yl | 5-Br-1H-pyrazol-1-yl |
| 3-CHF₂-1H-pyrazol-1-yl | 3-Et-1H-pyrazol-1-yl | 3-Cl-1H-pyrazol-1-yl | 3-I-1H-pyrazol-1-yl |
| 4-CHF₂-1H-pyrazol-1-yl | 4-Et-1H-pyrazol-1-yl | 4-Cl-1H-pyrazol-1-yl | 4-I-1H-pyrazol-1-yl |
| 5-CHF₂-1H-pyrazol-1-yl | 5-Et-1H-pyrazol-1-yl | 5-Cl-1H-pyrazol-1-yl | 5-I-pyrazol-1-yl |
| 1H-pyrazol-1-yl | 1H-1,2,3-triazol-1-yl | 1H-1,2,3-triazol-1-yl | 1H-1,2,3-triazol-2-yl |
| 1H-pyrrol-1-yl | 1-Me-1H-pyrazol-3-yl | 1-CF₃-1H-pyrazol-3-yl | |
| 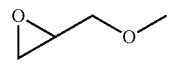 | 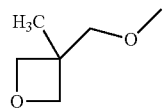 | 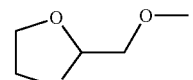 | 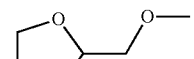 |

TABLE 2-continued

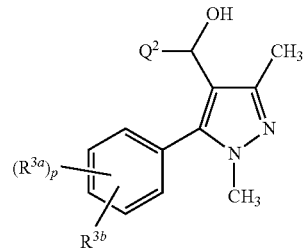

$Q^2$ is 2,4,6-tri-F—Ph, $(R^{3a})_p$ is 2,6-di-F.

The present disclosure also includes Tables 1B through 215B, each of which is constructed the same as Table 2 above, except that the row heading in Table 2 (i.e. "$Q^2$ is 2,4,6-tri-F-Ph, $(R^{3a})_p$ is 2,6-di-F") is replaced with the respective row headings shown below. For Example, in Table 1B the row heading is "$Q^2$ is 2,4,6-tri-F-Ph, $(R^{3a})_p$ is 2-F", and $R^{3b}$ is as defined in Table 2 above. Thus, the first entry in Table 1B specifically discloses 5-[2-fluoro-4-(-propyn-1-yloxy)phenyl]-1,3-dimethyl-α-(2,4,6-trifluorophenyl)-1H-pyrazol-4-methanol. Tables 2B through 215B are constructed similarly.

| Table | Row Heading |
|---|---|
| 1B | $Q^2$ is 2,4,6-tri-F—Ph, $(R^{3a})_p$ is 2-F. |
| 2B | $Q^2$ is 2,4,6-tri-F—Ph, $(R^{3a})_p$ is 2-Cl. |
| 3B | $Q^2$ is 2,4,6-tri-F—Ph, $(R^{3a})_p$ is 2-Br. |
| 4B | $Q^2$ is 2,4,6-tri-F—Ph, $(R^{3a})_p$ is 2-Me. |
| 5B | $Q^2$ is 2,4,6-tri-F—Ph, $(R^{3a})_p$ is 2-F, 6-Cl. |
| 6B | $Q^2$ is 2,4,6-tri-F—Ph, $(R^{3a})_p$ is 2-Cl, 6-F. |
| 7B | $Q^2$ is 2,4,6-tri-F—Ph, $(R^{3a})_p$ is 2,6-di-Cl. |
| 8B | $Q^2$ is 2,6-di-F—Ph, $(R^{3a})_p$ is 2,6-di-F. |
| 9B | $Q^2$ is 2,6-di-F—Ph, $(R^{3a})_p$ is 2-F. |
| 10B | $Q^2$ is 2,6-di-F—Ph, $(R^{3a})_p$ is 2-Cl. |
| 11B | $Q^2$ is 2,6-di-F—Ph, $(R^{3a})_p$ is 2-Br. |
| 12B | $Q^2$ is 2,6-di-F—Ph, $(R^{3a})_p$ is 2-Me. |
| 13B | $Q^2$ is 2,6-di-F—Ph, $(R^{3a})_p$ is 2-F, 6-Cl. |
| 14B | $Q^2$ is 2,6-di-F—Ph, $(R^{3a})_p$ is 2-Cl, 6-F. |
| 15B | $Q^2$ is 2,6-di-F—Ph, $(R^{3a})_p$ is 2,6-di-Cl. |
| 16B | $Q^2$ is 2,6-di-F-4-MeO—Ph, $(R^{3a})_p$ is 2,6-di-F. |
| 17B | $Q^2$ is 2,6-di-F-4-MeO—Ph, $(R^{3a})_p$ is 2-F. |
| 18B | $Q^2$ is 2,6-di-F-4-MeO—Ph, $(R^{3a})_p$ is 2-Cl. |
| 19B | $Q^2$ is 2,6-di-F-4-MeO—Ph, $(R^{3a})_p$ is 2-Br. |
| 20B | $Q^2$ is 2,6-di-F-4-MeO—Ph, $(R^{3a})_p$ is 2-Me. |
| 21B | $Q^2$ is 2,6-di-F-4-MeO—Ph, $(R^{3a})_p$ is 2-F, 6-Cl. |
| 22B | $Q^2$ is 2,6-di-F-4-MeO—Ph, $(R^{3a})_p$ is 2-Cl, 6-F. |
| 23B | $Q^2$ is 2,6-di-F-4-MeO—Ph, $(R^{3a})_p$ is 2,6-di-Cl. |
| 24B | $Q^2$ is 2,6-di-F-4-Me—Ph, $(R^{3a})_p$ is 2,6-di-F. |
| 25B | $Q^2$ is 2,6-di-F-4-Me—Ph, $(R^{3a})_p$ is 2-F. |
| 26B | $Q^2$ is 2,6-di-F-4-Me—Ph, $(R^{3a})_p$ is 2-Cl. |
| 27B | $Q^2$ is 2,6-di-F-4-Me—Ph, $(R^{3a})_p$ is 2-Br. |
| 28B | $Q^2$ is 2,6-di-F-4-Me—Ph, $(R^{3a})_p$ is 2-Me. |
| 29B | $Q^2$ is 2,6-di-F-4-Me—Ph, $(R^{3a})_p$ is 2-F, 6-Cl |
| 30B | $Q^2$ is 2,6-di-F-4-Me—Ph, $(R^{3a})_p$ is 2-Cl, 6-F. |
| 31B | $Q^2$ is 2,6-di-F-4-Me—Ph, $(R^{3a})_p$ is 2,6-di-Cl. |
| 32B | $Q^2$ is 2,6-di-F-4-CN—Ph, $(R^{3a})_p$ is 2,6-di-F. |
| 33B | $Q^2$ is 2,6-di-F-4-CN—Ph, $(R^{3a})_p$ is 2-F. |
| 34B | $Q^2$ is 2,6-di-F-4-CN—Ph, $(R^{3a})_p$ is 2-Cl. |
| 35B | $Q^2$ is 2,6-di-F-4-CN—Ph, $(R^{3a})_p$ is 2-Br. |
| 36B | $Q^2$ is 2,6-di-F-4-CN—Ph, $(R^{3a})_p$ is 2-Me. |
| 37B | $Q^2$ is 2,6-di-F-4-CN—Ph, $(R^{3a})_p$ is 2-F, 6-Cl. |
| 38B | $Q^2$ is 2,6-di-F-4-CN—Ph, $(R^{3a})_p$ is 2-Cl, 6-F. |
| 39B | $Q^2$ is 2,6-di-F-4-CN—Ph, $(R^{3a})_p$ is 2,6-di-Cl. |
| 40B | $Q^2$ is 2,6-di-F-4-Cl—Ph, $(R^{3a})_p$ is 2,6-di-F. |
| 41B | $Q^2$ is 2,6-di-F-4-Cl—Ph, $(R^{3a})_p$ is 2-F. |
| 42B | $Q^2$ is 2,6-di-F-4-Cl—Ph, $(R^{3a})_p$ is 2-Cl. |
| 43B | $Q^2$ is 2,6-di-F-4-Cl—Ph, $(R^{3a})_p$ is 2-Br. |
| 44B | $Q^2$ is 2,6-di-F-4-Cl—Ph, $(R^{3a})_p$ is 2-Me. |
| 45B | $Q^2$ is 2,6-di-F-4-Cl—Ph, $(R^{3a})_p$ is 2-F, 6-Cl. |
| 46B | $Q^2$ is 2,6-di-F-4-Cl—Ph, $(R^{3a})_p$ is 2-Cl, 6-F. |
| 47B | $Q^2$ is 2,6-di-F-4-Cl—Ph, $(R^{3a})_p$ is 2,6-di-Cl. |
| 48B | $Q^2$ is 2,6-di-F-4-Br—Ph, $(R^{3a})_p$ is 2,6-di-F. |
| 49B | $Q^2$ is 2,6-di-F-4-Br—Ph, $(R^{3a})_p$ is 2-F. |
| 50B | $Q^2$ is 2,6-di-F-4-Br—Ph, $(R^{3a})_p$ is 2-Cl. |
| 51B | $Q^2$ is 2,6-di-F-4-Br—Ph, $(R^{3a})_p$ is 2-Br. |
| 52B | $Q^2$ is 2,6-di-F-4-Br—Ph, $(R^{3a})_p$ is 2-Me. |
| 53B | $Q^2$ is 2,6-di-F-4-Br—Ph, $(R^{3a})_p$ is 2-F, 6-Cl. |
| 54B | $Q^2$ is 2,6-di-F-4-Br—Ph, $(R^{3a})_p$ is 2-Cl, 6-F. |
| 55B | $Q^2$ is 2,6-di-F-4-Br—Ph, $(R^{3a})_p$ is 2,6-di-Cl. |
| 56B | $Q^2$ is 2,4-di-F—Ph, $(R^{3a})_p$ is 2,6-di-F. |
| 57B | $Q^2$ is 2,4-di-F—Ph, $(R^{3a})_p$ is 2-F. |
| 58B | $Q^2$ is 2,4-di-F—Ph, $(R^{3a})_p$ is 2-Cl. |
| 59B | $Q^2$ is 2,4-di-F—Ph, $(R^{3a})_p$ is 2-Br. |
| 60B | $Q^2$ is 2,4-di-F—Ph, $(R^{3a})_p$ is 2-Me |
| 61B | $Q^2$ is 2,4-di-F—Ph, $(R^{3a})_p$ is 2-F, 6-Cl. |
| 62B | $Q^2$ is 2,4-di-F—Ph, $(R^{3a})_p$ is 2-Cl, 6-F. |
| 63B | $Q^2$ is 2,4-di-F—Ph, $(R^{3a})_p$ is 2,6-di-Cl |
| 64B | $Q^2$ is 2,4-di-F-6-Cl—Ph, $(R^{3a})_p$ is 2,6-di-F. |
| 65B | $Q^2$ is 2,4-di-F-6-Cl—Ph, $(R^{3a})_p$ is 2-F. |
| 66B | $Q^2$ is 2,4-di-F-6-Cl—Ph, $(R^{3a})_p$ is 2-Cl. |
| 67B | $Q^2$ is 2,4-di-F-6-Cl—Ph, $(R^{3a})_p$ is 2-Br. |
| 68B | $Q^2$ is 2,4-di-F-6-Cl—Ph, $(R^{3a})_p$ is 2-Me. |
| 69B | $Q^2$ is 2,4-di-F-6-Cl—Ph, $(R^{3a})_p$ is 2-F, 6-Cl. |
| 70B | $Q^2$ is 2,4-di-F-6-Cl—Ph, $(R^{3a})_p$ is 2-Cl, 6-F. |
| 71B | $Q^2$ is 2,4-di-F-6-Cl—Ph, $(R^{3a})_p$ is 2,6-di-Cl. |
| 72B | $Q^2$ is 2,4-di-F-6-Br—Ph, $(R^{3a})_p$ is 2,6-di-F |
| 73B | $Q^2$ is 2,4-di-F-6-Br—Ph, $(R^{3a})_p$ is 2-F. |
| 74B | $Q^2$ is 2,4-di-F-6-Br—Ph, $(R^{3a})_p$ is 2-Cl. |
| 75B | $Q^2$ is 2,4-di-F-6-Br—Ph, $(R^{3a})_p$ is 2-Br. |
| 76B | $Q^2$ is 2,4-di-F-6-Br—Ph, $(R^{3a})_p$ is 2-Me. |
| 77B | $Q^2$ is 2,4-di-F-6-Br—Ph, $(R^{3a})_p$ is 2-F, 6-Cl. |

| Table | Row Heading |
|---|---|
| 78B | Q² is 2,4-di-F-6-Br—Ph, (R³ᵃ)ₚ is 2-Cl, 6-F. |
| 79B | Q² is 2,4-di-F-6-Br—Ph, (R³ᵃ)ₚ is 2,6-di-Cl. |
| 80B | Q² is 2-Cl-4-Me-6-F—Ph, (R³ᵃ)ₚ is 2,6-di-F. |
| 81B | Q² is 2-Cl-4-Me-6-F—Ph, (R³ᵃ)ₚ is 2-F. |
| 82B | Q² is 2-Cl-4-Me-6-F—Ph, (R³ᵃ)ₚ is 2-Cl. |
| 83B | Q² is 2-Cl-4-Me-6-F—Ph, (R³ᵃ)ₚ is 2-Br. |
| 84B | Q² is 2-Cl-4-Me-6-F—Ph, (R³ᵃ)ₚ is 2-Me. |
| 85B | Q² is 2-Cl-4-Me-6-F—Ph, (R³ᵃ)ₚ is 2-F, 6-Cl. |
| 86B | Q² is 2-Cl-4-Me-6-F—Ph, (R³ᵃ)ₚ is 2-Cl, 6-F. |
| 87B | Q² is 2-Cl-4-Me-6-F—Ph, (R³ᵃ)ₚ is 2,6-di-Cl. |
| 88B | Q² is 2-Cl-4-MeO-6-F—Ph, (R³ᵃ)ₚ is 2,6-di-F. |
| 89B | Q² is 2-Cl-4-MeO-6-F—Ph, (R³ᵃ)ₚ is 2-F. |
| 90B | Q² is 2-Cl-4-MeO-6-F—Ph, (R³ᵃ)ₚ is 2-Cl. |
| 91B | Q² is 2-Cl-4-MeO-6-F—Ph, (R³ᵃ)ₚ is 2-Br. |
| 92B | Q² is 2-Cl-4-MeO-6-F—Ph, (R³ᵃ)ₚ is 2-Me. |
| 93B | Q² is 2-Cl-4-MeO-6-F—Ph, (R³ᵃ)ₚ is 2-F, 6-Cl. |
| 94B | Q² is 2-Cl-4-MeO-6-F—Ph, (R³ᵃ)ₚ is 2-Cl, 6-F. |
| 95B | Q² is 2-Cl-4-MeO-6-F—Ph, (R³ᵃ)ₚ is 2,6-di-Cl. |
| 96B | Q² is 2-Br-4-Me-6-F—Ph, (R³ᵃ)ₚ is 2,6-di-F. |
| 97B | Q² is 2-Br-4-Me-6-F—Ph, (R³ᵃ)ₚ is 2-F. |
| 98B | Q² is 2-Br-4-Me-6-F—Ph, (R³ᵃ)ₚ is 2-Cl. |
| 99B | Q² is 2-Br-4-Me-6-F—Ph, (R³ᵃ)ₚ is 2-Br. |
| 100B | Q² is 2-Br-4-Me-6-F—Ph, (R³ᵃ)ₚ is 2-Me |
| 101B | Q² is 2-Br-4-Me-6-F—Ph, (R³ᵃ)ₚ is 2-F, 6-Cl. |
| 102B | Q² is 2-Br-4-Me-6-F—Ph, (R³ᵃ)ₚ is 2-Cl, 6-F. |
| 103B | Q² is 2-Br-4-Me-6-F—Ph, (R³ᵃ)ₚ is 2,6-di-Cl. |
| 104B | Q² is 2-Br-4-MeO-6-F—Ph, (R³ᵃ)ₚ is 2,6-di-F. |
| 105B | Q² is 2-Br-4-MeO-6-F—Ph, (R³ᵃ)ₚ is 2-F. |
| 106B | Q² is 2-Br-4-MeO-6-F—Ph, (R³ᵃ)ₚ is 2-Cl. |
| 107B | Q² is 2-Br-4-MeO-6-F—Ph, (R³ᵃ)ₚ is 2-Br. |
| 108B | Q² is 2-Br-4-MeO-6-F—Ph, (R³ᵃ)ₚ is 2-Me. |
| 109B | Q² is 2-Br-4-MeO-6-F—Ph, (R³ᵃ)ₚ is 2-F, 6-Cl. |
| 110B | Q² is 2-Br-4-MeO-6-F—Ph, (R³ᵃ)ₚ is 2-Cl, 6-F. |
| 111B | Q² is 2-Br-4-MeO-6-F—Ph, (R³ᵃ)ₚ is 2,6-di-Cl. |
| 112B | Q² is 2,6-di-Cl-4-Me—Ph, (R³ᵃ)ₚ is 2,6-di-F. |
| 113B | Q² is 2,6-di-Cl-4-Me—Ph, (R³ᵃ)ₚ is 2-F. |
| 114B | Q² is 2,6-di-Cl-4-Me—Ph, (R³ᵃ)ₚ is 2-Cl. |
| 115B | Q² is 2,6-di-Cl-4-Me—Ph, (R³ᵃ)ₚ is 2-Br. |
| 116B | Q² is 2,6-di-Cl-4-Me—Ph, (R³ᵃ)ₚ is 2-Me. |
| 117B | Q² is 2,6-di-Cl-4-Me—Ph, (R³ᵃ)ₚ is 2-F, 6-Cl |
| 118B | Q² is 2,6-di-Cl-4-Me—Ph, (R³ᵃ)ₚ is 2-Cl, 6-F. |
| 119B | Q² is 2,6-di-Cl-4-Me—Ph, (R³ᵃ)ₚ is 2,6-di-Cl. |
| 120B | Q² is 2,6-di-Br-4-Me—Ph, (R³ᵃ)ₚ is 2,6-di-F. |
| 121B | Q² is 2,6-di-Br-4-Me—Ph, (R³ᵃ)ₚ is 2-F. |
| 122B | Q² is 2,6-di-Br-4-Me—Ph, (R³ᵃ)ₚ is 2-Cl. |
| 123B | Q² is 2,6-di-Br-4-Me—Ph, (R³ᵃ)ₚ is 2-Br. |
| 124B | Q² is 2,6-di-Br-4-Me—Ph, (R³ᵃ)ₚ is 2-Me. |
| 125B | Q² is 2,6-di-Br-4-Me—Ph, (R³ᵃ)ₚ is 2-F, 6-Cl. |
| 126B | Q² is 2,6-di-Br-4-Me—Ph, (R³ᵃ)ₚ is 2-Cl, 6-F. |
| 127B | Q² is 2,6-di-Br-4-Me—Ph, (R³ᵃ)ₚ is 2,6-di-Cl. |
| 128B | Q² is 2,4,6-tri-Cl—Ph, (R³ᵃ)ₚ is 2,6-di-F. |
| 129B | Q² is 2,4,6-tri-Cl—Ph, (R³ᵃ)ₚ is 2-F. |
| 130B | Q² is 2,4,6-tri-Cl—Ph, (R³ᵃ)ₚ is 2-Cl. |
| 131B | Q² is 2,4,6-tri-Cl—Ph, (R³ᵃ)ₚ is 2-Br. |
| 132B | Q² is 2,4,6-tri-Cl—Ph, (R³ᵃ)ₚ is 2-Me. |
| 133B | Q² is 2,4,6-tri-Cl—Ph, (R³ᵃ)ₚ is 2-F, 6-Cl. |
| 134B | Q² is 2,4,6-tri-Cl—Ph, (R³ᵃ)ₚ is 2-Cl, 6-F. |
| 135B | Q² is 2,4,6-tri-Cl—Ph, (R³ᵃ)ₚ is 2,6-di-Cl. |
| 136B | Q² is 2-Cl-4-F, (R³ᵃ)ₚ is 2,6-di-F. |
| 137B | Q² is 2-Cl-4-F, (R³ᵃ)ₚ is 2-F. |
| 138B | Q² is 2-Cl-4-F, (R³ᵃ)ₚ is 2-Cl. |
| 139B | Q² is 2-Cl-4-F, (R³ᵃ)ₚ is 2-Br. |
| 140B | Q² is 2-Cl-4-F, (R³ᵃ)ₚ is 2-Me. |
| 141B | Q² is 2-Cl-4-F, (R³ᵃ)ₚ is 2-F, 6-Cl |
| 142B | Q² is 2-Cl-4-F, (R³ᵃ)ₚ is 2-Cl, 6-F |
| 143B | Q² is 2-Cl-4-F, (R³ᵃ)ₚ is 2,6-di-Cl. |
| 144B | Q² is 2-Cl-4-Me, (R³ᵃ)ₚ is 2,6-di-F. |
| 145B | Q² is 2-Cl-4-Me, (R³ᵃ)ₚ is 2-F. |
| 146B | Q² is 2-Cl-4-Me, (R³ᵃ)ₚ is 2-Cl. |
| 147B | Q² is 2-Cl-4-Me, (R³ᵃ)ₚ is 2-Br. |
| 148B | Q² is 2-Cl-4-Me, (R³ᵃ)ₚ is 2-Me. |
| 149B | Q² is 2-Cl-4-Me, (R³ᵃ)ₚ is 2-F, 6-Cl. |
| 150B | Q² is 2-Cl-4-Me, (R³ᵃ)ₚ is 2-Cl, 6-F. |
| 151B | Q² is 2-Cl-4-Me, (R³ᵃ)ₚ is 2,6-di-Cl. |
| 152B | Q² is 2-Cl-4-MeO, (R³ᵃ)ₚ is 2,6-di-F. |
| 153B | Q² is 2-Cl-4-MeO, (R³ᵃ)ₚ is 2-F |
| 154B | Q² is 2-Cl-4-MeO, (R³ᵃ)ₚ is 2-Cl. |
| 155B | Q² is 2-Cl-4-MeO, (R³ᵃ)ₚ is 2-Br. |
| 156B | Q² is 2-Cl-4-MeO, (R³ᵃ)ₚ is 2-Me . . . |
| 157B | Q² is 2-Cl-4-MeO, (R³ᵃ)ₚ is 2-F, 6-Cl. |
| 158B | Q² is 2-Cl-4-MeO, (R³ᵃ)ₚ is 2-Cl, 6-F. |
| 159B | Q² is 2-Cl-4-MeO, (R³ᵃ)ₚ is 2,6-di-Cl. |
| 160B | Q² is 2-Br-4-F, (R³ᵃ)ₚ is 2,6-di-F. |
| 161B | Q² is 2-Br-4-F, (R³ᵃ)ₚ is 2-F. |
| 162B | Q² is 2-Br-4-F, (R³ᵃ)ₚ is 2-Cl. |
| 163B | Q² is 2-Br-4-F, (R³ᵃ)ₚ is 2-Br. |
| 164B | Q² is 2-Br-4-F, (R³ᵃ)ₚ is 2-Me. |
| 165B | Q² is 2-Br-4-F, (R³ᵃ)ₚ is 2-F, 6-Cl. |
| 166B | Q² is 2-Br-4-F, (R³ᵃ)ₚ is 2-Cl, 6-F. |
| 167B | Q² is 2-Br-4-F, (R³ᵃ)ₚ is 2,6-di-Cl. |
| 168B | Q² is 2-Br-4-Me, (R³ᵃ)ₚ is 2,6-di-F. |
| 169B | Q² is 2-Br-4-Me, (R³ᵃ)ₚ is 2-F. |
| 170B | Q² is 2-Br-4-Me, (R³ᵃ)ₚ is 2-Cl. |
| 171B | Q² is 2-Br-4-Me, (R³ᵃ)ₚ is 2-Br. |
| 172B | Q² is 2-Br-4-Me, (R³ᵃ)ₚ is 2-Me. |
| 173B | Q² is 2-Br-4-Me, (R³ᵃ)ₚ is 2-F, 6-Cl. |
| 174B | Q² is 2-Br-4-Me, (R³ᵃ)ₚ is 2-Cl, 6-F. |
| 175B | Q² is 2-Br-4-Me, (R³ᵃ)ₚ is 2,6-di-Cl. |
| 176B | Q² is 2-Br-4-MeO, (R³ᵃ)ₚ is 2,6-di-F. |
| 177B | Q² is 2-Br-4-MeO, (R³ᵃ)ₚ is 2-F. |
| 178B | Q² is 2-Br-4-MeO, (R³ᵃ)ₚ is 2-Cl. |
| 179B | Q² is 2-Br-4-MeO, (R³ᵃ)ₚ is 2-Br. |
| 180B | Q² is 2-Br-4-MeO, (R³ᵃ)ₚ is 2-Me. |
| 181B | Q² is 2-Br-4-MeO, (R³ᵃ)ₚ is 2-F, 6-Cl. |
| 182B | Q² is 2-Br-4-MeO, (R³ᵃ)ₚ is 2-Cl, 6-F. |
| 183B | Q² is 2-Br-4-MeO, (R³ᵃ)ₚ is 2,6-di-Cl. |
| 184B | Q² is 2,4-di-Cl, (R³ᵃ)ₚ is 2,6-di-F. |
| 185B | Q² is 2,4-di-Cl, (R³ᵃ)ₚ is 2-F. |
| 186B | Q² is 2,4-di-Cl, (R³ᵃ)ₚ is 2-Cl. |
| 187B | Q² is 2,4-di-Cl, (R³ᵃ)ₚ is 2-Br. |
| 188B | Q² is 2,4-di-Cl, (R³ᵃ)ₚ is 2-Me. |
| 189B | Q² is 2,4-di-Cl, (R³ᵃ)ₚ is 2-F, 6-Cl. |
| 190B | Q² is 2,4-di-Cl, (R³ᵃ)ₚ is 2-Cl, 6-F. |
| 191B | Q² is 2,4-di-Cl, (R³ᵃ)ₚ is 2,6-di-Cl. |
| 192B | Q² is 2,6-di-Cl, (R³ᵃ)ₚ is 2,6-di-F. |
| 193B | Q² is 2,6-di-Cl, (R³ᵃ)ₚ is 2-F. |
| 194B | Q² is 2,6-di-Cl, (R³ᵃ)ₚ is 2-Cl. |
| 195B | Q² is 2,6-di-Cl, (R³ᵃ)ₚ is 2-Br. |
| 196B | Q² is 2,6-di-Cl, (R³ᵃ)ₚ is 2-Me. |
| 197B | Q² is 2,6-di-Cl, (R³ᵃ)ₚ is 2-F, 6-Cl. |
| 198B | Q² is 2,6-di-Cl, (R³ᵃ)ₚ is 2-Cl, 6-F. |
| 199B | Q² is 2,6-di-Cl, (R³ᵃ)ₚ is 2,6-di-Cl. |
| 200B | Q² is 2,4-di-Me, (R³ᵃ)ₚ is 2,6-di-F. |
| 201B | Q² is 2,4-di-Me, (R³ᵃ)ₚ is 2-F. |
| 202B | Q² is 2,4-di-Me, (R³ᵃ)ₚ is 2-Cl. |
| 203B | Q² is 2,4-di-Me, (R³ᵃ)ₚ is 2-Br. |
| 204B | Q² is 2,4-di-Me, (R³ᵃ)ₚ is 2-Me. |
| 205B | Q² is 2,4-di-Me, (R³ᵃ)ₚ is 2-F, 6-Cl. |
| 206B | Q² is 2,4-di-Me, (R³ᵃ)ₚ is 2-Cl, 6-F. |
| 207B | Q² is 2,4-di-Me, (R³ᵃ)ₚ is 2,6-di-Cl. |
| 208B | Q² is 2,6-di-Me, (R³ᵃ)ₚ is 2,6-di-F. |
| 209B | Q² is 2,6-di-Me, (R³ᵃ)ₚ is 2-F. |
| 210B | Q² is 2,6-di-Me, (R³ᵃ)ₚ is 2-Cl |
| 211B | Q² is 2,6-di-Me, (R³ᵃ)ₚ is 2-Br. |
| 212B | Q² is 2,6-di-Me, (R³ᵃ)ₚ is 2-Me. |
| 213B | Q² is 2,6-di-Me, (R³ᵃ)ₚ is 2-F, 6-Cl. |
| 214B | Q² is 2,6-di-Me, (R³ᵃ)ₚ is 2-Cl, 6-F. |
| 215B | Q² is 2,6-di-Me, (R³ᵃ)ₚ is 2,6-di-Cl. |

TABLE 3

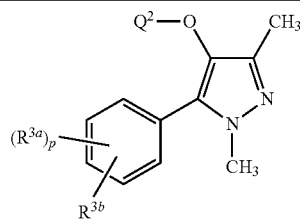

$Q^2$ is 2,4,6-tri-F—Ph, $(R^{3a})_p$ is 2,6-di-F.

| $R^{3b}$ | $R^{3b}$ | $R^{3b}$ | $R^{3b}$ |
|---|---|---|---|
| 4-(HC≡CCH₂O)— | 4-(MeC≡CCH₂O)— | 4-(HC≡CCH₂CH₂O)— | 4-(MeC≡CCH₂CH₂O)— |
| 4-(H₂C=CHCH₂O)— | 4-(MeHC=CCH₂O)— | 4-(ClHC=CHCH₂O)— | 4-(Cl₂C=CHCH₂O)— |
| 4-(HC≡C(Me)CHO)— | 4-(H₂C=C(Me)CHO)— | 4-(H₂C=CHCH(Me)O)— | 4-(MeHC=CHCH(Me)O)— |
| 4-n-butoxy | 4-i-butoxy | 4-s-butoxy | 4-n-pentoxy |
| 4-i-pentoxy | 4-s-pentoxy | 4-(c-Pr—HC=CHCH₂O)— | 4-(c-Pr—C≡CCH₂O)— |
| 4-(c-Pr—HC=CH)— | 4-(c-Pr—C≡C)— | 4-(c-Bu—CH₂O)— | 4-(c-Pr—CH₂O)— |
| 4-(c-pentyl-CH₂O)— | 4-(HO—N=CH)— | 4-(MeO—N=CH)— | 4-(HO—N=C(Me))— |
| 4-(MeO—N=C(Me))— | 4-(MeHC=N—O)— | 4-(Me₂C=N—O)— | 4-(H₂C=N—O)— |
| 4-(H₂N—N=CH)— | 4-(MeNH—N=CH)— | 4-(Me₂N—N=CH)— | 4-(H₂N—N=C(Me))— |
| 4-(MeNH—N=C(Me))— | 4-(Me₂N—N=C(Me))— | 4-(MeHC=N—NH)— | 4-(Me₂C=N—NH)— |
| 4-(H₂C=N—NH)— | 4-(MeHC=N—N(Me))— | 4-(Me₂C=N—N(Me))— | 4-(H₂C=N—N(Me))— |
| 3-(HC≡CCH₂O)— | 3-(MeC≡CCH₂O)— | 3-(HC≡CCH₂CH₂O)— | 3-(MeC≡CCH₂CH₂O)— |
| 3-(H₂C=CHCH₂O)— | 3-(MeHC=CHCH₂O)— | 3-(ClHC=CHCH₂O)— | 3-(Cl₂C=CHCH₂O)— |
| 3-(HC≡C(Me)CHO)— | 3-(H₂C=C(Me)CHO)— | 3-(H₂C=CHCH(Me)O)— | 3-(MeHC=CHCH(Me)O)— |
| 3-n-butoxy | 3-i-butoxy | 3-s-butoxy | 3-n-pentoxy |
| 3-i-pentoxy | 3-s-pentoxy | 3-(c-Pr—HC=CHCH₂O)— | 3-(c-Pr—C≡CCH₂O)— |
| 3-(c-Pr—HC=CH)— | 3-(c-Pr—C≡C)— | 3-(c-Pr—CH₂O)— | 3-(c-Bu—CH₂O)— |
| 3-(c-pentyl-CH₂O)— | 3-(HO—N=CH)— | 3-(MeO—N=CH)— | 3-(HO—N=C(Me))— |
| 3-(MeO—N=C(Me))— | 3-(MeHC=N—O)— | 3-(Me₂C=N—O)— | 3-(H₂C=N—O)— |
| 3-(H₂N—N=CH)— | 3-(MeNH—N=CH)— | 3-(Me₂N—N=CH)— | 3-(H₂N—N=C(Me))— |
| 3-(MeNH—N=C(Me))— | 3-(Me₂N—N=C(Me))— | 3-(MeHC=N—NH)— | 3-(Me₂C=N—NH)— |
| 3-(H₂C=N—NH)— | 3-(MeHC=N—N(Me))— | 3-(Me₂C=N—N(Me))— | 3-(H₂C=N—N(Me))— |
| 3-CF₃-1H-pyrazol-1-yl | 3-Me-1H-pyrazol-1-yl | 3-F-1H-pyrazol-1-yl | 3-Br-1H-pyrazol-1-yl |
| 4-CF₃-1H-pyrazol-1-yl | 4-Me-1H-pyrazol-1-yl | 4-F-1H-pyrazol-1-yl | 4-Br-1H-pyrazol-1-yl |
| 5-CF₃-1H-pyrazol-1-yl | 5-Me-1H-pyrazol-1-yl | 5-F-1H-pyrazol-1-yl | 5-Br-1H-pyrazol-1-yl |
| 3-CHF₂-1H-pyrazol-1-yl | 3-Et-1H-pyrazol-1-yl | 3-Cl-1H-pyrazol-1-yl | 3-I-1H-pyrazol-1-yl |
| 4-CHF₂-1H-pyrazol-1-yl | 3-Et-1H-pyrazol-1-yl | 4-Cl-1H-pyrazol-1-yl | 4-I-1H-pyrazol-1-yl |
| 5-CHF₂-1H-pyrazol-1-yl | 3-Et-1H-pyrazol-1-yl | 5-Cl-1H-pyrazol-1-yl | 5-I-pyrazol-1-yl |
| 1H-pyrazol-1-yl | 1H-1,2,3-triazol-1-yl | 1H-1,2,3-triazol-1-yl | 1H-1,2,3-triazol-2-yl |
| 1H-pyrrol-1-yl | 1-Me-1H-pyrazol-3-yl | 1-CF₃-1H-pyrazol-3-yl | |

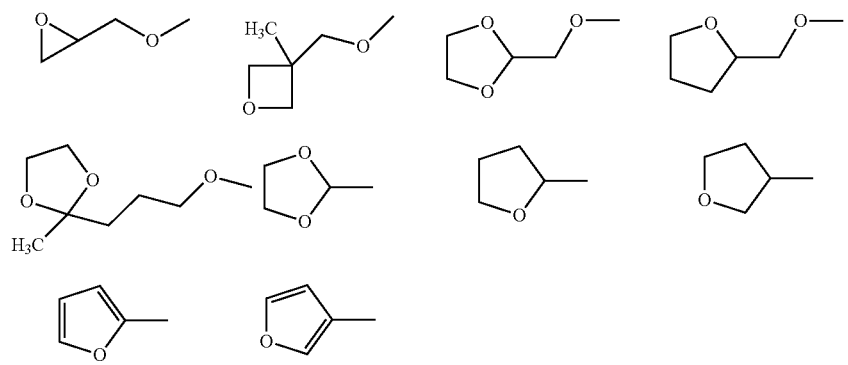

The present disclosure also includes Tables 1C through 215C, each of which is constructed the same as Table 3 above, except that the row heading in Table 3 (i.e. "$Q^2$ is 2,4,6-tri-F-Ph, $(R^{3a})_p$ is 2,6-di-F") is replaced with the respective row headings shown below. For Example, in Table 1C the row heading is "$Q^2$ is 2,4,6-tri-F-Ph, $(R^{3a})_p$ is 2-F", and $R^{3b}$ is as defined in Table 3 above. Thus, the first entry in Table 1C specifically discloses 5-[2-fluoro-4-(-propyn-1-yloxy)phenyl]-1,3-dimethyl-4-[(2,4,6-trifluoro-phenyl)-methyl]-1H-pyrazole. Tables 2C through 215C are constructed similarly.

| Table | Row Heading |
|---|---|
| 1C | $Q^2$ is 2,4,6-tri-F—Ph, $(R^{3a})_p$ is 2-F. |
| 2C | $Q^2$ is 2,4,6-tri-F—Ph, $(R^{3a})_p$ is 2-Cl. |
| 3C | $Q^2$ is 2,4,6-tri-F—Ph, $(R^{3a})_p$ is 2-Br. |
| 4C | $Q^2$ is 2,4,6-tri-F—Ph, $(R^{3a})_p$ is 2-Me. |
| 5C | $Q^2$ is 2,4,6-tri-F—Ph, $(R^{3a})_p$ is 2-F, 6-Cl. |
| 6C | $Q^2$ is 2,4,6-tri-F—Ph, $(R^{3a})_p$ is 2-Cl, 6-F. |
| 7C | $Q^2$ is 2,4,6-tri-F—Ph, $(R^{3a})_p$ is 2,6-di-Cl. |
| 8C | $Q^2$ is 2,6-di-F—Ph, $(R^{3a})_p$ is 2,6-di-F. |
| 9C | $Q^2$ is 2,6-di-F—Ph, $(R^{3a})_p$ is 2-F. |
| 10C | $Q^2$ is 2,6-di-F—Ph, $(R^{3a})_p$ is 2-Cl. |
| 11C | $Q^2$ is 2,6-di-F—Ph, $(R^{3a})_p$ is 2-Br. |

| Table | Row Heading |
|---|---|
| 12C | Q² is 2,6-di-F—Ph, (R³ᵃ)_p is 2-Me. |
| 13C | Q² is 2,6-di-F—Ph, (R³ᵃ)_p is 2-F, 6-Cl. |
| 14C | Q² is 2,6-di-F—Ph, (R³ᵃ)_p is 2-Cl, 6-F. |
| 15C | Q² is 2,6-di-F—Ph, (R³ᵃ)_p is 2,6-di-Cl. |
| 16C | Q² is 2,6-di-F-4-MeO—Ph, (R³ᵃ)_p is 2,6-di-F. |
| 17C | Q² is 2,6-di-F-4-MeO—Ph, (R³ᵃ)_p is 2-F. |
| 18C | Q² is 2,6-di-F-4-MeO—Ph, (R³ᵃ)_p is 2-Cl. |
| 19C | Q² is 2,6-di-F-4-MeO—Ph, (R³ᵃ)_p is 2-Br. |
| 20C | Q² is 2,6-di-F-4-MeO—Ph, (R³ᵃ)_p is 2-Me. |
| 21C | Q² is 2,6-di-F-4-MeO—Ph, (R³ᵃ)_p is 2-F, 6-Cl. |
| 22C | Q² is 2,6-di-F-4-MeO—Ph, (R³ᵃ)_p is 2-Cl, 6-F. |
| 23C | Q² is 2,6-di-F-4-MeO—Ph, (R³ᵃ)_p is 2,6-di-Cl. |
| 24C | Q² is 2,6-di-F-4-Me—Ph, (R³ᵃ)_p is 2,6-di-F. |
| 25C | Q² is 2,6-di-F-4-Me—Ph, (R³ᵃ)_p is 2-F. |
| 26C | Q² is 2,6-di-F-4-Me—Ph, (R³ᵃ)_p is 2-Cl. |
| 27C | Q² is 2,6-di-F-4-Me—Ph, (R³ᵃ)_p is 2-Br. |
| 28C | Q² is 2,6-di-F-4-Me—Ph, (R³ᵃ)_p is 2-Me. |
| 29C | Q² is 2,6-di-F-4-Me—Ph, (R³ᵃ)_p is 2-F, 6-Cl |
| 30C | Q² is 2,6-di-F-4-Me—Ph, (R³ᵃ)_p is 2-Cl, 6-F. |
| 31C | Q² is 2,6-di-F-4-Me—Ph, (R³ᵃ)_p is 2,6-di-Cl. |
| 32C | Q² is 2,6-di-F-4-CN—Ph, (R³ᵃ)_p is 2,6-di-F. |
| 33C | Q² is 2,6-di-F-4-CN—Ph, (R³ᵃ)_p is 2-F. |
| 34C | Q² is 2,6-di-F-4-CN—Ph, (R³ᵃ)_p is 2-Cl. |
| 35C | Q² is 2,6-di-F-4-CN—Ph, (R³ᵃ)_p is 2-Br. |
| 36C | Q² is 2,6-di-F-4-CN—Ph, (R³ᵃ)_p is 2-Me. |
| 37C | Q² is 2,6-di-F-4-CN—Ph, (R³ᵃ)_p is 2-F, 6-Cl. |
| 38C | Q² is 2,6-di-F-4-CN—Ph, (R³ᵃ)_p is 2-Cl, 6-F. |
| 39C | Q² is 2,6-di-F-4-CN—Ph, (R³ᵃ)_p is 2,6-di-Cl. |
| 40C | Q² is 2,6-di-F-4-Cl—Ph, (R³ᵃ)_p is 2,6-di-F. |
| 41C | Q² is 2,6-di-F-4-Cl—Ph, (R³ᵃ)_p is 2-F. |
| 42C | Q² is 2,6-di-F-4-Cl—Ph, (R³ᵃ)_p is 2-Cl. |
| 43C | Q² is 2,6-di-F-4-Cl—Ph, (R³ᵃ)_p is 2-Br. |
| 44C | Q² is 2,6-di-F-4-Cl—Ph, (R³ᵃ)_p is 2-Me. |
| 45C | Q² is 2,6-di-F-4-Cl—Ph, (R³ᵃ)_p is 2-F, 6-Cl. |
| 46C | Q² is 2,6-di-F-4-Cl—Ph, (R³ᵃ)_p is 2-Cl, 6-F. |
| 47C | Q² is 2,6-di-F-4-Cl—Ph, (R³ᵃ)_p is 2,6-di-Cl. |
| 48C | Q² is 2,6-di-F-4-Br—Ph, (R³ᵃ)_p is 2,6-di-F. |
| 49C | Q² is 2,6-di-F-4-Br—Ph, (R³ᵃ)_p is 2-F. |
| 50C | Q² is 2,6-di-F-4-Br—Ph, (R³ᵃ)_p is 2-Cl. |
| 51C | Q² is 2,6-di-F-4-Br—Ph, (R³ᵃ)_p is 2-Br. |
| 52C | Q² is 2,6-di-F-4-Br—Ph, (R³ᵃ)_p is 2-Me. |
| 53C | Q² is 2,6-di-F-4-Br—Ph, (R³ᵃ)_p is 2-F, 6-Cl. |
| 54C | Q² is 2,6-di-F-4-Br—Ph, (R³ᵃ)_p is 2-Cl, 6-F. |
| 55C | Q² is 2,6-di-F-4-Br—Ph, (R³ᵃ)_p is 2,6-di-Cl. |
| 56C | Q² is 2,4-di-F—Ph, (R³ᵃ)_p is 2,6-di-F. |
| 57C | Q² is 2,4-di-F—Ph, (R³ᵃ)_p is 2-F. |
| 58C | Q² is 2,4-di-F—Ph, (R³ᵃ)_p is 2-Cl. |
| 59C | Q² is 2,4-di-F—Ph, (R³ᵃ)_p is 2-Br. |
| 60C | Q² is 2,4-di-F—Ph, (R³ᵃ)_p is 2-Me |
| 61C | Q² is 2,4-di-F—Ph, (R³ᵃ)_p is 2-F, 6-Cl. |
| 62C | Q² is 2,4-di-F—Ph, (R³ᵃ)_p is 2-Cl, 6-F. |
| 63C | Q² is 2,4-di-F—Ph, (R³ᵃ)_p is 2,6-di-Cl |
| 64C | Q² is 2,4-di-F-6-Cl—Ph, (R³ᵃ)_p is 2,6-di-F. |
| 65C | Q² is 2,4-di-F-6-Cl—Ph, (R³ᵃ)_p is 2-F. |
| 66C | Q² is 2,4-di-F-6-Cl—Ph, (R³ᵃ)_p is 2-Cl. |
| 67C | Q² is 2,4-di-F-6-Cl—Ph, (R³ᵃ)_p is 2-Br. |
| 68C | Q² is 2,4-di-F-6-Cl—Ph, (R³ᵃ)_p is 2-Me. |
| 69C | Q² is 2,4-di-F-6-Cl—Ph, (R³ᵃ)_p is 2-F, 6-Cl. |
| 70C | Q² is 2,4-di-F-6-Cl—Ph, (R³ᵃ)_p is 2-Cl, 6-F. |
| 71C | Q² is 2,4-di-F-6-Cl—Ph, (R³ᵃ)_p is 2,6-di-Cl. |
| 72C | Q² is 2,4-di-F-6-Br—Ph, (R³ᵃ)_p is 2,6-di-F |
| 73C | Q² is 2,4-di-F-6-Br—Ph, (R³ᵃ)_p is 2-F. |
| 74C | Q² is 2,4-di-F-6-Br—Ph, (R³ᵃ)_p is 2-Cl. |
| 75C | Q² is 2,4-di-F-6-Br—Ph, (R³ᵃ)_p is 2-Br. |
| 76C | Q² is 2,4-di-F-6-Br—Ph, (R³ᵃ)_p is 2-Me. |
| 77C | Q² is 2,4-di-F-6-Br—Ph, (R³ᵃ)_p is 2-F, 6-Cl. |
| 78C | Q² is 2,4-di-F-6-Br—Ph, (R³ᵃ)_p is 2-Cl, 6-F. |
| 79C | Q² is 2,4-di-F-6-Br—Ph, (R³ᵃ)_p is 2,6-di-Cl. |
| 80C | Q² is 2-Cl-4-Me-6-F—Ph, (R³ᵃ)_p is 2,6-di-F. |
| 81C | Q² is 2-Cl-4-Me-6-F—Ph, (R³ᵃ)_p is 2-F. |
| 82C | Q² is 2-Cl-4-Me-6-F—Ph, (R³ᵃ)_p is 2-Cl. |
| 83C | Q² is 2-Cl-4-Me-6-F—Ph, (R³ᵃ)_p is 2-Br. |
| 84C | Q² is 2-Cl-4-Me-6-F—Ph, (R³ᵃ)_p is 2-Me. |
| 85C | Q² is 2-Cl-4-Me-6-F—Ph, (R³ᵃ)_p is 2-F, 6-Cl. |
| 86C | Q² is 2-Cl-4-Me-6-F—Ph, (R³ᵃ)_p is 2-Cl, 6-F. |
| 87C | Q² is 2-Cl-4-Me-6-F—Ph, (R³ᵃ)_p is 2,6-di-Cl. |
| 88C | Q² is 2-Cl-4-MeO-6-F—Ph, (R³ᵃ)_p is 2,6-di-F. |
| 89C | Q² is 2-Cl-4-MeO-6-F—Ph, (R³ᵃ)_p is 2-F. |
| 90C | Q² is 2-Cl-4-MeO-6-F—Ph, (R³ᵃ)_p is 2-Cl. |
| 91C | Q² is 2-Cl-4-MeO-6-F—Ph, (R³ᵃ)_p is 2-Br. |
| 92C | Q² is 2-Cl-4-MeO-6-F—Ph, (R³ᵃ)_p is 2-Me. |
| 93C | Q² is 2-Cl-4-MeO-6-F—Ph, (R³ᵃ)_p is 2-F, 6-Cl. |
| 94C | Q² is 2-Cl-4-MeO-6-F—Ph, (R³ᵃ)_p is 2-Cl, 6-F. |
| 95C | Q² is 2-Cl-4-MeO-6-F—Ph, (R³ᵃ)_p is 2,6-di-Cl. |
| 96C | Q² is 2-Br-4-Me-6-F—Ph, (R³ᵃ)_p is 2,6-di-F. |
| 97C | Q² is 2-Br-4-Me-6-F—Ph, (R³ᵃ)_p is 2-F. |
| 98C | Q² is 2-Br-4-Me-6-F—Ph, (R³ᵃ)_p is 2-Cl. |
| 99C | Q² is 2-Br-4-Me-6-F—Ph, (R³ᵃ)_p is 2-Br. |
| 100C | Q² is 2-Br-4-Me-6-F—Ph, (R³ᵃ)_p is 2-Me |
| 101C | Q² is 2-Br-4-Me-6-F—Ph, (R³ᵃ)_p is 2-F, 6-Cl. |
| 102C | Q² is 2-Br-4-Me-6-F—Ph, (R³ᵃ)_p is 2-Cl, 6-F. |
| 103C | Q² is 2-Br-4-Me-6-F—Ph, (R³ᵃ)_p is 2,6-di-Cl. |
| 104C | Q² is 2-Br-4-MeO-6-F—Ph, (R³ᵃ)_p is 2,6-di-F. |
| 105C | Q² is 2-Br-4-MeO-6-F—Ph, (R³ᵃ)_p is 2-F. |
| 106C | Q² is 2-Br-4-MeO-6-F—Ph, (R³ᵃ)_p is 2-Cl. |
| 107C | Q² is 2-Br-4-MeO-6-F—Ph, (R³ᵃ)_p is 2-Br. |
| 108C | Q² is 2-Br-4-MeO-6-F—Ph, (R³ᵃ)_p is 2-Me. |
| 109C | Q² is 2-Br-4-MeO-6-F—Ph, (R³ᵃ)_p is 2-F, 6-Cl. |
| 110C | Q² is 2-Br-4-MeO-6-F—Ph, (R³ᵃ)_p is 2-Cl, 6-F. |
| 111C | Q² is 2-Br-4-MeO-6-F—Ph, (R³ᵃ)_p is 2,6-di-Cl. |
| 112C | Q² is 2,6-di-Cl-4-Me—Ph, (R³ᵃ)_p is 2,6-di-F. |
| 113C | Q² is 2,6-di-Cl-4-Me—Ph, (R³ᵃ)_p is 2-F. |
| 114C | Q² is 2,6-di-Cl-4-Me—Ph, (R³ᵃ)_p is 2-Cl. |
| 115C | Q² is 2,6-di-Cl-4-Me—Ph, (R³ᵃ)_p is 2-Br. |
| 116C | Q² is 2,6-di-Cl-4-Me—Ph, (R³ᵃ)_p is 2-Me. |
| 117C | Q² is 2,6-di-Cl-4-Me—Ph, (R³ᵃ)_p is 2-F, 6-Cl |
| 118C | Q² is 2,6-di-Cl-4-Me—Ph, (R³ᵃ)_p is 2-Cl, 6-F. |
| 119C | Q² is 2,6-di-Cl-4-Me—Ph, (R³ᵃ)_p is 2,6-di-Cl. |
| 120C | Q² is 2,6-di-Br-4-Me—Ph, (R³ᵃ)_p is 2,6-di-F. |
| 121C | Q² is 2,6-di-Br-4-Me—Ph, (R³ᵃ)_p is 2-F. |
| 122C | Q² is 2,6-di-Br-4-Me—Ph, (R³ᵃ)_p is 2-Cl. |
| 123C | Q² is 2,6-di-Br-4-Me—Ph, (R³ᵃ)_p is 2-Br. |
| 124C | Q² is 2,6-di-Br-4-Me—Ph, (R³ᵃ)_p is 2-Me. |
| 125C | Q² is 2,6-di-Br-4-Me—Ph, (R³ᵃ)_p is 2-F, 6-Cl. |
| 126C | Q² is 2,6-di-Br-4-Me—Ph, (R³ᵃ)_p is 2-Cl, 6-F. |
| 127C | Q² is 2,6-di-Br-4-Me—Ph, (R³ᵃ)_p is 2,6-di-Cl. |
| 128C | Q² is 2,4,6-tri-Cl—Ph, (R³ᵃ)_p is 2,6-di-F. |
| 129C | Q² is 2,4,6-tri-Cl—Ph, (R³ᵃ)_p is 2-F. |
| 130C | Q² is 2,4,6-tri-Cl—Ph, (R³ᵃ)_p is 2-Cl. |
| 131C | Q² is 2,4,6-tri-Cl—Ph, (R³ᵃ)_p is 2-Br. |
| 132C | Q² is 2,4,6-tri-Cl—Ph, (R³ᵃ)_p is 2-Me. |
| 133C | Q² is 2,4,6-tri-Cl—Ph, (R³ᵃ)_p is 2-F, 6-Cl. |
| 134C | Q² is 2,4,6-tri-Cl—Ph, (R³ᵃ)_p is 2-Cl, 6-F. |
| 135C | Q² is 2,4,6-tri-Cl—Ph, (R³ᵃ)_p is 2,6-di-Cl. |
| 136C | Q² is 2-Cl-4-F, (R³ᵃ)_p is 2,6-di-F. |
| 137C | Q² is 2-Cl-4-F, (R³ᵃ)_p is 2-F. |
| 138C | Q² is 2-Cl-4-F, (R³ᵃ)_p is 2-Cl. |
| 139C | Q² is 2-Cl-4-F, (R³ᵃ)_p is 2-Br. |
| 140C | Q² is 2-Cl-4-F, (R³ᵃ)_p is 2-Me. |
| 141C | Q² is 2-Cl-4-F, (R³ᵃ)_p is 2-F, 6-Cl |
| 142C | Q² is 2-Cl-4-F, (R³ᵃ)_p is 2-Cl, 6-F |
| 143C | Q² is 2-Cl-4-F, (R³ᵃ)_p is 2,6-di-Cl. |
| 144C | Q² is 2-Cl-4-Me, (R³ᵃ)_p is 2,6-di-F. |
| 145C | Q² is 2-Cl-4-Me, (R³ᵃ)_p is 2-F. |
| 146C | Q² is 2-Cl-4-Me, (R³ᵃ)_p is 2-Cl. |
| 147C | Q² is 2-Cl-4-Me, (R³ᵃ)_p is 2-Br. |
| 148C | Q² is 2-Cl-4-Me, (R³ᵃ)_p is 2-Me. |
| 149C | Q² is 2-Cl-4-Me, (R³ᵃ)_p is 2-F, 6-Cl. |
| 150C | Q² is 2-Cl-4-Me, (R³ᵃ)_p is 2-Cl, 6-F. |
| 151C | Q² is 2-Cl-4-Me, (R³ᵃ)_p is 2,6-di-Cl. |
| 152C | Q² is 2-Cl-4-MeO, (R³ᵃ)_p is 2,6-di-F. |
| 153C | Q² is 2-Cl-4-MeO, (R³ᵃ)_p is 2-F |
| 154C | Q² is 2-Cl-4-MeO, (R³ᵃ)_p is 2-Cl. |
| 155C | Q² is 2-Cl-4-MeO, (R³ᵃ)_p is 2-Br. |
| 156C | Q² is 2-Cl-4-MeO, (R³ᵃ)_p is 2-Me . . . |
| 157C | Q² is 2-Cl-4-MeO, (R³ᵃ)_p is 2-F, 6-Cl. |
| 158C | Q² is 2-Cl-4-MeO, (R³ᵃ)_p is 2-Cl, 6-F. |
| 159C | Q² is 2-Cl-4-MeO, (R³ᵃ)_p is 2,6-di-Cl. |
| 160C | Q² is 2-Br-4-F, (R³ᵃ)_p is 2,6-di-F. |
| 161C | Q² is 2-Br-4-F, (R³ᵃ)_p is 2-F. |
| 162C | Q² is 2-Br-4-F, (R³ᵃ)_p is 2-Cl. |
| 163C | Q² is 2-Br-4-F, (R³ᵃ)_p is 2-Br. |
| 164C | Q² is 2-Br-4-F, (R³ᵃ)_p is 2-Me. |
| 165C | Q² is 2-Br-4-F, (R³ᵃ)_p is 2-F, 6-Cl. |

-continued

| Table | Row Heading |
|---|---|
| 166C | $Q^2$ is 2-Br-4-F, $(R^{3a})_p$ is 2-Cl, 6-F. |
| 167C | $Q^2$ is 2-Br-4-F, $(R^{3a})_p$ is 2,6-di-Cl. |
| 168C | $Q^2$ is 2-Br-4-Me, $(R^{3a})_p$ is 2,6-di-F. |
| 169C | $Q^2$ is 2-Br-4-Me, $(R^{3a})_p$ is 2-F. |
| 170C | $Q^2$ is 2-Br-4-Me, $(R^{3a})_p$ is 2-Cl. |
| 171C | $Q^2$ is 2-Br-4-Me, $(R^{3a})_p$ is 2-Br. |
| 172C | $Q^2$ is 2-Br-4-Me, $(R^{3a})_p$ is 2-Me. |
| 173C | $Q^2$ is 2-Br-4-Me, $(R^{3a})_p$ is 2-F, 6-Cl. |
| 174C | $Q^2$ is 2-Br-4-Me, $(R^{3a})_p$ is 2-Cl, 6-F. |
| 175C | $Q^2$ is 2-Br-4-Me, $(R^{3a})_p$ is 2,6-di-Cl. |
| 176C | $Q^2$ is 2-Br-4-MeO, $(R^{3a})_p$ is 2,6-di-F. |
| 177C | $Q^2$ is 2-Br-4-MeO, $(R^{3a})_p$ is 2-F. |
| 178C | $Q^2$ is 2-Br-4-MeO, $(R^{3a})_p$ is 2-Cl. |
| 179C | $Q^2$ is 2-Br-4-MeO, $(R^{3a})_p$ is 2-Br. |
| 180C | $Q^2$ is 2-Br-4-MeO, $(R^{3a})_p$ is 2-Me. |
| 181C | $Q^2$ is 2-Br-4-MeO, $(R^{3a})_p$ is 2-F, 6-Cl. |
| 182C | $Q^2$ is 2-Br-4-MeO, $(R^{3a})_p$ is 2-Cl, 6-F. |
| 183C | $Q^2$ is 2-Br-4-MeO, $(R^{3a})_p$ is 2,6-di-Cl. |
| 184C | $Q^2$ is 2,4-di-Cl, $(R^{3a})_p$ is 2,6-di-F. |
| 185C | $Q^2$ is 2,4-di-Cl, $(R^{3a})_p$ is 2-F. |
| 186C | $Q^2$ is 2,4-di-Cl, $(R^{3a})_p$ is 2-Cl. |
| 187C | $Q^2$ is 2,4-di-Cl, $(R^{3a})_p$ is 2-Br. |
| 188C | $Q^2$ is 2,4-di-Cl, $(R^{3a})_p$ is 2-Me. |
| 189C | $Q^2$ is 2,4-di-Cl, $(R^{3a})_p$ is 2-F, 6-Cl. |
| 190C | $Q^2$ is 2,4-di-Cl, $(R^{3a})_p$ is 2-Cl, 6-F. |
| 191C | $Q^2$ is 2,4-di-Cl, $(R^{3a})_p$ is 2,6-di-Cl. |
| 192C | $Q^2$ is 2,6-di-Cl, $(R^{3a})_p$ is 2,6-di-F. |
| 193C | $Q^2$ is 2,6-di-Cl, $(R^{3a})_p$ is 2-F. |
| 194C | $Q^2$ is 2,6-di-Cl, $(R^{3a})_p$ is 2-Cl. |
| 195C | $Q^2$ is 2,6-di-Cl, $(R^{3a})_p$ is 2-Br. |
| 196C | $Q^2$ is 2,6-di-Cl, $(R^{3a})_p$ is 2-Me. |
| 197C | $Q^2$ is 2,6-di-Cl, $(R^{3a})_p$ is 2-F, 6-Cl. |
| 198C | $Q^2$ is 2,6-di-Cl, $(R^{3a})_p$ is 2-Cl, 6-F. |
| 199C | $Q^2$ is 2,6-di-Cl, $(R^{3a})_p$ is 2,6-di-Cl. |
| 200C | $Q^2$ is 2,4-di-Me, $(R^{3a})_p$ is 2,6-di-F. |
| 201C | $Q^2$ is 2,4-di-Me, $(R^{3a})_p$ is 2-F. |
| 202C | $Q^2$ is 2,4-di-Me, $(R^{3a})_p$ is 2-Cl. |
| 203C | $Q^2$ is 2,4-di-Me, $(R^{3a})_p$ is 2-Br. |
| 204C | $Q^2$ is 2,4-di-Me, $(R^{3a})_p$ is 2-Me. |
| 205C | $Q^2$ is 2,4-di-Me, $(R^{3a})_p$ is 2-F, 6-Cl. |
| 206C | $Q^2$ is 2,4-di-Me, $(R^{3a})_p$ is 2-Cl, 6-F. |
| 207C | $Q^2$ is 2,4-di-Me, $(R^{3a})_p$ is 2,6-di-Cl. |
| 208C | $Q^2$ is 2,6-di-Me, $(R^{3a})_p$ is 2,6-di-F. |
| 209C | $Q^2$ is 2,6-di-Me, $(R^{3a})_p$ is 2-F. |
| 210C | $Q^2$ is 2,6-di-Me, $(R^{3a})_p$ is 2-Cl |
| 211C | $Q^2$ is 2,6-di-Me, $(R^{3a})_p$ is 2-Br. |
| 212C | $Q^2$ is 2,6-di-Me, $(R^{3a})_p$ is 2-Me. |
| 213C | $Q^2$ is 2,6-di-Me, $(R^{3a})_p$ is 2-F, 6-Cl. |
| 214C | $Q^2$ is 2,6-di-Me, $(R^{3a})_p$ is 2-Cl, 6-F. |
| 215C | $Q^2$ is 2,6-di-Me, $(R^{3a})_p$ is 2,6-di-Cl. |

Formulation/Utility

A compound of this invention will generally be used as a fungicidal active ingredient in a composition, i.e. formulation, with at least one additional component selected from the group consisting of surfactants, solid diluents and liquid diluents, which serve as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-95 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide*, 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such as polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is waterimmiscible, an emulsifier is typically added to emulsify the active-containing solvent upon dilution with water. Active ingredient slurries, with particle diameters of up to 2,000 µm can be wet milled using media mills to obtain particles with average diameters below 3 µm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 µm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, U K, 2000.

In the following Examples, all percentages are by weight and all formulations are prepared in conventional ways. Compound numbers refer to compounds in Index Table A. Without further elaboration, it is believed that one skilled in the art using the preceding description can utilize the present invention to its fullest extent. The following Examples are, therefore, to be constructed as merely illustrative, and not limiting of the disclosure in any way whatsoever.

Example A

High Strength Concentrate

| | |
|---|---|
| Compound 2 | 98.5% |
| silica aerogel | 0.5% |
| synthetic amorphous fine silica | 1.0% |

Example B

Wettable Powder

| | |
|---|---|
| Compound 2 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

Granule

| | |
|---|---|
| Compound 2 | 10.0% |
| attapulgite granules (low volatile matter, 0.71/0.30 mm; U.S.S. No. 25-50 sieves) | 90.0% |

Example D

Extruded Pellet

| | |
|---|---|
| Compound 2 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

Emulsifiable Concentrate

| | |
|---|---|
| Compound 2 | 10.0% |
| polyoxyethylene sorbitol hexoleate | 20.0% |
| $C_6$-$C_{10}$ fatty acid methyl ester | 70.0% |

Example F

Microemulsion

| | |
|---|---|
| Compound 2 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

Seed Treatment

| | |
|---|---|
| Compound 2 | 20.00% |
| polyvinylpyrrolidone-vinyl acetate copolymer | 5.00% |

| | |
|---|---|
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Water-soluble and water-dispersible formulations are typically diluted with water to form aqueous compositions before application. Aqueous compositions for direct applications to the plant or portion thereof (e.g., spray tank compositions) typically at least about 1 ppm or more (e.g., from 1 ppm to 100 ppm) of the compound(s) of this invention.

The compounds of this invention are useful as plant disease control agents. The present invention therefore further comprises a method for controlling plant diseases caused by fungal plant pathogens comprising applying to the plant or portion thereof to be protected, or to the plant seed to be protected, an effective amount of a compound of the invention or a fungicidal composition containing said compound. The compounds and/or compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, turf, vegetable, field, cereal, and fruit crops. These pathogens include: Oomycetes, including *Phytophthora* diseases such as *Phytophthora infestans, Phytophthora megasperma, Phytophthora parasitica, Phytophthora cinnamomi* and *Phytophthora capsici, Pythium* diseases such as *Pythium aphanidermatum*, and diseases in the Peronosporaceae family such as *Plasmopara viticola, Peronospora* spp. (including *Peronospora tabacina* and *Peronospora parasitica*), *Pseudoperonospora* spp. (including *Pseudoperonospora cubensis*) and *Bremia lactucae*; Ascomycetes, including *Alternaria* diseases such as *Alternaria solani* and *Alternaria brassicae, Guignardia* diseases such as *Guignardia bidwell, Venturia* diseases such as *Venturia inaequalis, Septoria* diseases such as *Septoria nodorum* and *Septoria tritici*, powdery mildew diseases such as *Erysiphe* spp. (including *Erysiphe graminis* and *Erysiphe polygoni*), *Uncinula necatur, Sphaerotheca fuliginea, Podosphaera leucotricha* and *Pseudocercosporella herpotrichoides, Botrytis* diseases such as *Botrytis cinerea, Monilinia fructicola, Sclerotinia* diseases such as *Sclerotinia sclerotiorum, Sclerotinia minor, Magnaporthe grisea*, and *Phomopsis viticola, Helminthosporium* diseases such as *Helminthosporium tritici repentis* and *Pyrenophora teres*, anthracnose diseases such as *Glomerella* or *Colletotrichum* spp. (such as *Colletotrichum graminicola* and *Colletotrichum orbiculare*), and *Gaeumannomyces graminis*; Basidiomycetes, including rust diseases caused by *Puccinia* spp. (such as *Puccinia recondita, Puccinia striiformis, Puccinia hordei, Puccinia graminis* and *Puccinia arachidis*), *Hemileia vastatrix* and *Phakopsora pachyrhizi*; other pathogens including *Rutstroemia floccosum* (also known as *Sclerotinia homoeocarpa*); *Rhizoctonia* spp. (such as *Rhizoctonia solani*); *Fusarium* diseases such as *Fusarium roseum, Fusarium graminearum* and *Fusarium oxysporum Verticillium dahliae; Sclerotium rolfsii; Ryncho- sporium secalis; Cercosporidium personatum, Cercospora arachidicola* and *Cercospora beticola; Rhizopus* spp. (such as *Rhizopus stolonifer*); *Aspergillus* spp. (such as *Aspergillus flavus* and *Aspergillus parasiticus*); and other genera and species closely related to these pathogens. In addition to their fungicidal activity, the compositions or combinations also have activity against bacteria such as *Erwinia amylovora, Xanthomonas campestris, Pseudomonas syringae*, and other related species. Furthermore, the compounds of this invention are useful in treating postharvest diseases of fruits and vegetables caused by fungi and bacteria. These infections can occur before, during and after harvest. For example, infections can occur before harvest and then remain dormant until some point during ripening (e.g., host begins tissue changes in such a way that infection can progress); also infections can arise from surface wounds created by mechanical or insect injury. In this respect, the compounds of this invention can reduce losses (i.e. losses resulting from quantity and quality) due to postharvest diseases which may occur at any time from harvest to consumption. Treatment of postharvest diseases with compounds of the invention can increase the period of time during which perishable edible plant parts (e.g, fruits, seeds, foliage, stems, bulbs, tubers) can be stored refrigerated or un-refrigerated after harvest, and remain edible and free from noticeable or harmful degradation or contamination by fungi or other microorganisms. Treatment of edible plant parts before or after harvest with compounds of the invention can also decrease the formation of toxic metabolites of fungi or other microorganisms, for example, mycotoxins such as aflatoxins.

Plant disease control is ordinarily accomplished by applying an effective amount of a compound of this invention either pre- or post-infection, to the portion of the plant to be protected such as the roots, stems, foliage, fruits, seeds, tubers or bulbs, or to the media (soil or sand) in which the plants to be protected are growing. The compounds can also be applied to seeds to protect the seeds and seedlings developing from the seeds. The compounds can also be applied through irrigation water to treat plants. Control of postharvest pathogens which infect the produce before harvest is typically accomplished by field application of a compound of this invention, and in cases where infection occurs after harvest the compounds can be applied to the harvested crop as dips, sprays, fumigants, treated wraps and box liners.

Rates of application for these compounds (i.e. a fungicidally effective amount) can be influenced by factors such as the plant diseases to be controlled, the plant species to be protected, ambient moisture and temperature and should be determined under actual use conditions. One skilled in the art can easily determine through simple experimentation the fungicidally effective amount necessary for the desired level of plant disease control. Foliage can normally be protected when treated at a rate of from less than about 1 g/ha to about 5,000 g/ha of active ingredient. Seed and seedlings can normally be protected when seed is treated at a rate of from about 0.1 to about 10 g per kilogram of seed.

Compounds of this invention can also be mixed with one or more other biologically active compounds or agents including fungicides, insecticides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Thus the present invention also pertains to a composition comprising a compound of Formula 1 (in a fungicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

Of note is a composition which in addition to the compound of Formula 1 include at least one fungicidal compound selected from the group consisting of the classes (1) methyl benzimidazole carbamate (MBC) fungicides; (2) dicarboximide fungicides; (3) demethylation inhibitor (DMI) fungicides; (4) phenylamide fungicides; (5) amine/morpholine fungicides; (6) phospholipid biosynthesis inhibitor fungicides; (7) carboxamide fungicides; (8) hydroxy(2-amino-)pyrimidine fungicides; (9) anilinopyrimidine fungicides; (10) N-phenyl carbamate fungicides; (11) quinone outside inhibitor (QoI) fungicides; (12) phenylpyrrole fungicides; (13) quinoline fungicides; (14) lipid peroxidation inhibitor fungicides; (15) melanin biosynthesis inhibitors-reductase (MBI-R) fungicides; (16) melanin biosynthesis inhibitors-dehydratase (MBI-D) fungicides; (17) hydroxyanilide fungicides; (18) squalene-epoxidase inhibitor fungicides; (19) polyoxin fungicides; (20) phenylurea fungicides; (21) quinone inside inhibitor (QiI) fungicides; (22) benzamide fungicides; (23) enopyranuronic acid antibiotic fungicides; (24) hexopyranosyl antibiotic fungicides; (25) glucopyranosyl antibiotic: protein synthesis fungicides; (26) glucopyranosyl antibiotic: trehalase and inositol biosynthesis fungicides; (27) cyanoacetamideoxime fungicides; (28) carbamate fungicides; (29) oxidative phosphorylation uncoupling fungicides; (30) organo tin fungicides; (31) carboxylic acid fungicides; (32) heteroaromatic fungicides; (33) phosphonate fungicides; (34) phthalamic acid fungicides; (35) benzotriazine fungicides; (36) benzene-sulfonamide fungicides; (37) pyridazinone fungicides; (38) thiophene-carboxamide fungicides; (39) pyrimidinamide fungicides; (40) carboxylic acid amide (CAA) fungicides; (41) tetracycline antibiotic fungicides; (42) thiocarbamate fungicides; (43) benzamide fungicides; (44) host plant defense induction fungicides; (45) multi-site contact activity fungicides; (46) fungicides other than classes (1) through (45); and salts of compounds of classes (1) through (46).

Further descriptions of these classes of fungicidal compounds are provided below.

(1) "Methyl benzimidazole carbamate (MBC) fungicides" (Fungicide Resistance Action Committee (FRAC) code 1) inhibit mitosis by binding to β-tubulin during microtubule assembly. Inhibition of microtubule assembly can disrupt cell division, transport within the cell and cell structure. Methyl benzimidazole carbamate fungicides include benzimidazoles and thiophanates. The benzimidazoles include benomyl, carbendazim, fuberidazole and thiabendazole. The thiophanates include thiophanate and thiophanate-methyl.

(2) "Dicarboximide fungicides" (Fungicide Resistance Action Committee (FRAC) code 2) are proposed to inhibit a lipid peroxidation in fungi through interference with NADH cytochrome c reductase. Examples include chlozolinate, iprodione, procymidone and vinclozolin.

(3) "Demethylation inhibitor (DMI) fungicides" (Fungicide Resistance Action Committee (FRAC) code 3) inhibit C14-demethylase, which plays a role in sterol production. Sterols, such as ergosterol, are needed for membrane structure and function, making them essential for the development of functional cell walls. Therefore, exposure to these fungicides results in abnormal growth and eventually death of sensitive fungi. Demethylation fungicides include piperazines, pyridines, pyrimidines, imidazoles and triazoles. The piperazines include triforine. The pyridines include buthiobate and pyrifenox. The pyrimidines include fenarimol, nuarimol and triarimol. The imidazoles include clotrimazole, imazalil, oxpoconazole, prochloraz, pefurazoate and triflumizole. The triazoles include azaconazole, bitertanol, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole, uniconazole, 1-[[(2S,3R)-3-(2-chlorophenyl)-2-(2,4-difluorophenyl)-2-oxiranyl]methyl]-1H-1,2,4-triazole, 2-[[(2S,3R)-3-(2-chlorophenyl)-2-(2,4-difluorophenyl)-2-oxiranyl]methyl]-1,2-dihydro-3H-1,2,4-triazole-3-thione and 1-[[(2S,3R)-3-(2-chlorophenyl)-2-(2,4-difluorophenyl)-2-oxiranyl]methyl]-5-(2-propen-1-ylthio)-1H-1,2,4-triazole. The imidazoles include clotrimazole, imazalil, oxpoconazole, prochloraz, pefurazoate and triflumizole. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

(4) "Phenylamide fungicides" (Fungicide Resistance Action Committee (FRAC) code 4) are specific inhibitors of RNA polymerase in Oomycete fungi. Sensitive fungi exposed to these fungicides show a reduced capacity to incorporate uridine into rRNA. Growth and development in sensitive fungi is prevented by exposure to this class of fungicide. Phenylamide fungicides include acylalanines, oxazolidinones and butyrolactones. The acylalanines include benalaxyl, benalaxyl-M, furalaxyl, metalaxyl and metalaxyl-M/mefenoxam. The oxazolidinones include oxadixyl. The butyrolactones include ofurace.

(5) "Amine/morpholine fungicides" (Fungicide Resistance Action Committee (FRAC) code 5) inhibit two target sites within the sterol biosynthetic pathway, $\Delta^8 \to \Delta^7$ isomerase and $\Delta^{14}$ reductase. Sterols, such as ergosterol, are needed for membrane structure and function, making them essential for the development of functional cell walls. Therefore, exposure to these fungicides results in abnormal growth and eventually death of sensitive fungi. Amine/morpholine fungicides (also known as non-DMI sterol biosynthesis inhibitors) include morpholines, piperidines and spiroketal-amines. The morpholines include aldimorph, dodemorph, fenpropimorph, tridemorph and trimorphamide. The piperidines include fenpropidin and piperalin. The spiroketal-amines include spiroxamine.

(6) "Phospholipid biosynthesis inhibitor fungicides" (Fungicide Resistance Action Committee (FRAC) code 6) inhibit growth of fungi by affecting phospholipid biosynthesis. Phospholipid biosynthesis fungicides include phophorothiolates and dithiolanes. The phosphorothiolates include edifenphos, iprobenfos and pyrazophos. The dithiolanes include isoprothiolane.

(7) "Carboxamide fungicides" (Fungicide Resistance Action Committee (FRAC) code 7) inhibit Complex II (succinate dehydrogenase) fungal respiration by disrupting a key enzyme in the Krebs Cycle (TCA cycle) named succinate dehydrogenase. Inhibiting respiration prevents the fungus from making ATP, and thus inhibits growth and reproduction. Carboxamide fungicides include phenyl benzamides, pyridinyl ethyl benzamides, furan carboxamides, oxathiin carboxamides, thiazole carboxamides, pyrazole carboxamides and pyridine carboxamides. The phenyl benzamides include benodanil, flutolanil and mepronil. The pyridinyl ethyl benzamides include fluopyram. The furan carboxamides include fenfuram. The oxathiin carboxamides include carboxin and oxycarboxin. The thiazole carboxamides include thifluzamide. The pyrazole carboxamides include furametpyr, penthiopyrad, bixafen, isopyrazam, benzovindiflupyr, N-[2-(1S,2R)-[1,1'-bicyclopropyl]-2-yl-phenyl]-3-(difluoromethyl)-1-methyl-1H-pyrazole-4-carboxamide, penflufen, (N-[2-(1,3-dimethylbutyl)phenyl]-5-fluoro-1,3-dimethyl-1H-pyrazole-4-carboxamide), N-[2-(2,4-dichlorophenyl)-2-methoxy-1-methylethyl]-3-(difluoromethyl)-1-methyl-1H-pyrazole-4-carboxamide and N-cyclopropyl-3-(difluoromethyl)-5-fluoro-1-methyl-N-[[2-(1-methylethyl)phenyl]methyl]-1H-pyrazole-4-carboxamide. The pyridine carboxamides include boscalid.

(8) "Hydroxy(2-amino-)pyrimidine fungicides" (Fungicide Resistance Action Committee (FRAC) code 8) inhibit nucleic acid synthesis by interfering with adenosine deaminase. Examples include bupirimate, dimethirimol and ethirimol.

(9) "Anilinopyrimidine fungicides" (Fungicide Resistance Action Committee (FRAC) code 9) are proposed to inhibit biosynthesis of the amino acid methionine and to disrupt the secretion of hydrolytic enzymes that lyse plant cells during infection. Examples include cyprodinil, mepanipyrim and pyrimethanil.

(10) "N-Phenyl carbamate fungicides" (Fungicide Resistance Action Committee (FRAC) code 10) inhibit mitosis by binding to β-tubulin and disrupting microtubule assembly. Inhibition of microtubule assembly can disrupt cell division, transport within the cell and cell structure. Examples include diethofencarb.

(11) "Quinone outside inhibitor (QoI) fungicides" (Fungicide Resistance Action Committee (FRAC) code 11) inhibit Complex III mitochondrial respiration in fungi by affecting ubiquinol oxidase. Oxidation of ubiquinol is blocked at the "quinone outside" ($Q_o$) site of the cytochrome $bc_1$ complex, which is located in the inner mitochondrial membrane of fungi. Inhibiting mitochondrial respiration prevents normal fungal growth and development. Quinone outside inhibitor fungicides (also known as strobilurin fungicides) include methoxyacrylates, methoxycarbamates, oximinoacetates, oximinoacetamides, oxazolidinediones, dihydrodioxazines, imidazolinones and benzylcarbamates. The methoxyacrylates include azoxystrobin, coumoxystrobin, enestroburin, flufenoxystrobin, picoxystrobin and pyraoxystrobin. The methoxycarbamates include pyraclostrobin, pyrametostrobin and triclopyricarb. The oximinoacetates include kresoxim-methyl and trifloxystrobin. The oximinoacetamides include dimoxystrobin, metominostrobin, orysastrobin, α-[methoxyimino]-N-methyl-2-[[[1-[3-(trifluoromethyl)phenyl]ethoxy]imino]-methyl]benzeneacetamide and 2-[[[3-(2,6-dichlorophenyl)-1-methyl-2-propen-1-ylidene]-amino]oxy]methyl]-α-(methoxyimino)-N-methylbenzeneacetamide. The oxazolidinediones include famoxadone. The dihydrodioxazines include fluoxastrobin. The imidazolinones include fenamidone. The benzylcarbamates include pyribencarb. Class (11) also includes 2-[(2,5-dimethylphenoxy)methyl]-α-methoxy-N-benzeneacetamide.

(12) "Phenylpyrrole fungicides" (Fungicide Resistance Action Committee (FRAC) code 12) inhibit a MAP protein kinase associated with osmotic signal transduction in fungi. Fenpiclonil and fludioxonil are examples of this fungicide class.

(13) "Azanaphthalene fungicides" (Fungicide Resistance Action Committee (FRAC) code 13) are proposed to inhibit signal transduction by affecting G-proteins in early cell signaling. They have been shown to interfere with germination and/or appressorium formation in fungi that cause powder mildew diseases. Azanaphthalene fungicides include aryloxyquinolines and quinazolinone. The aryloxyquinolines include quinoxyfen and tebufloquin. The quinazolinones include proquinazid.

(14) "Lipid peroxidation inhibitor fungicides" (Fungicide Resistance Action Committee (FRAC) code 14) are proposed to inhibit lipid peroxidation which affects membrane synthesis in fungi. Members of this class, such as etridiazole, may also affect other biological processes such as respiration and melanin biosynthesis. Lipid peroxidation fungicides include aromatic carbons and 1,2,4-thiadiazoles. The aromatic carbon fungicides include biphenyl, chloroneb, dicloran, quintozene, tecnazene and tolclofos-methyl. The 1,2,4-thiadiazole fungicides include etridiazole.

(15) "Melanin biosynthesis inhibitors-reductase (MBI-R) fungicides" (Fungicide Resistance Action Committee (FRAC) code 16.1) inhibit the naphthal reduction step in melanin biosynthesis. Melanin is required for host plant infection by some fungi. Melanin biosynthesis inhibitors-reductase fungicides include isobenzofuranones, pyrroloquinolinones and triazolobenzothiazoles. The isobenzofuranones include fthalide. The pyrroloquinolinones include pyroquilon. The triazolobenzothiazoles include tricyclazole.

(16) "Melanin biosynthesis inhibitors-dehydratase (MBI-D) fungicides" (Fungicide Resistance Action Committee (FRAC) code 16.2) inhibit scytalone dehydratase in melanin biosynthesis. Melanin in required for host plant infection by some fungi. Melanin biosynthesis inhibitors-dehydratase fungicides include cyclopropanecarboxamides, carboxamides and propionamides. The cyclopropanecarboxamides include carpropamid. The carboxamides include diclocymet. The propionamides include fenoxanil.

(17) "Hydroxyanilide fungicides (Fungicide Resistance Action Committee (FRAC) code 17) inhibit C4-demethylase which plays a role in sterol production. Examples include fenhexamid.

(18) "Squalene-epoxidase inhibitor fungicides" (Fungicide Resistance Action Committee (FRAC) code 18) inhibit squalene-epoxidase in ergosterol biosynthesis pathway. Sterols such as ergosterol are needed for membrane structure and function, making them essential for the development of functional cell walls. Therefore exposure to these fungicides results in abnormal growth and eventually death of sensitive fungi. Squalene-epoxidase inhibitor fungicides include thiocarbamates and allylaminess. The thiocarbamates include pyributicarb. The allylamines include naftifine and terbinafine.

(19) "Polyoxin fungicides" (Fungicide Resistance Action Committee (FRAC) code 19) inhibit chitin synthase. Examples include polyoxin.

(20) "Phenylurea fungicides" (Fungicide Resistance Action Committee (FRAC) code 20) are proposed to affect cell division. Examples include pencycuron.

(21) "Quinone inside inhibitor (QiI) fungicides" (Fungicide Resistance Action Committee (FRAC) code 21) inhibit Complex III mitochondrial respiration in fungi by affecting ubiquinol reductase. Reduction of ubiquinol is blocked at the "quinone inside" ($Q_i$) site of the cytochrome $bc_1$ complex, which is located in the inner mitochondrial membrane of fungi. Inhibiting mitochondrial respiration prevents normal fungal growth and development. Quinone inside inhibitor fungicides include cyanoimidazoles and sulfamoyltriazoles. The cyanoimidazoles include cyazofamid. The sulfamoyltriazoles include amisulbrom.

(22) "Benzamide fungicides" (Fungicide Resistance Action Committee (FRAC) code 22) inhibit mitosis by binding to β-tubulin and disrupting microtubule assembly. Inhibition of microtubule assembly can disrupt cell division, transport within the cell and cell structure. Examples include zoxamide.

(23) "Enopyranuronic acid antibiotic fungicides" (Fungicide Resistance Action Committee (FRAC) code 23) inhibit growth of fungi by affecting protein biosynthesis. Examples include blasticidin-S.

(24) "Hexopyranosyl antibiotic fungicides" (Fungicide Resistance Action Committee (FRAC) code 24) inhibit growth of fungi by affecting protein biosynthesis. Examples include kasugamycin.

(25) "Glucopyranosyl antibiotic: protein synthesis fungicides" (Fungicide Resistance Action Committee (FRAC) code 25) inhibit growth of fungi by affecting protein biosynthesis. Examples include streptomycin.

(26) "Glucopyranosyl antibiotic: trehalase and inositol biosynthesis fungicides" (Fungicide Resistance Action Committee (FRAC) code 26) inhibit trehalase in inositol biosynthesis pathway. Examples include validamycin.

(27) "Cyanoacetamideoxime fungicides (Fungicide Resistance Action Committee (FRAC) code 27) include cymoxanil.

(28) "Carbamate fungicides" (Fungicide Resistance Action Committee (FRAC) code 28) are considered multisite inhibitors of fungal growth. They are proposed to interfere with the synthesis of fatty acids in cell membranes, which then disrupts cell membrane permeability. Propamacarb, propamacarb-hydrochloride, iodocarb, and prothiocarb are examples of this fungicide class.

(29) "Oxidative phosphorylation uncoupling fungicides" (Fungicide Resistance Action Committee (FRAC) code 29) inhibit fungal respiration by uncoupling oxidative phosphorylation. Inhibiting respiration prevents normal fungal growth and development. This class includes 2,6-dinitroanilines such as fluazinam, pyrimidonehydrazones such as ferimzone and dinitrophenyl crotonates such as dinocap, meptyldinocap and binapacryl.

(30) "Organo tin fungicides" (Fungicide Resistance Action Committee (FRAC) code 30) inhibit adenosine triphosphate (ATP) synthase in oxidative phosphorylation pathway. Examples include fentin acetate, fentin chloride and fentin hydroxide.

(31) "Carboxylic acid fungicides" (Fungicide Resistance Action Committee (FRAC) code 31) inhibit growth of fungi by affecting deoxyribonucleic acid (DNA) topoisomerase type II (gyrase). Examples include oxolinic acid.

(32) "Heteroaromatic fungicides" (Fungicide Resistance Action Committee (FRAC) code 32) are proposed to affect DNA/ribonucleic acid (RNA) synthesis. Heteroaromatic fungicides include isoxazoles and isothiazolones. The isoxazoles include hymexazole and the isothiazolones include octhilinone.

(33) "Phosphonate fungicides" (Fungicide Resistance Action Committee (FRAC) code 33) include phosphorous acid and its various salts, including fosetyl-aluminum.

(34) "Phthalamic acid fungicides" (Fungicide Resistance Action Committee (FRAC) code 34) include teclofthalam.

(35) "Benzotriazine fungicides" (Fungicide Resistance Action Committee (FRAC) code 35) include triazoxide.

(36) "Benzene-sulfonamide fungicides" (Fungicide Resistance Action Committee (FRAC) code 36) include flusulfamide.

(37) "Pyridazinone fungicides" (Fungicide Resistance Action Committee (FRAC) code 37) include diclomezine.

(38) "Thiophene-carboxamide fungicides" (Fungicide Resistance Action Committee (FRAC) code 38) are proposed to affect ATP production. Examples include silthiofam.

(39) "Pyrimidinamide fungicides" (Fungicide Resistance Action Committee (FRAC) code 39) inhibit growth of fungi by affecting phospholipid biosynthesis and include diflumetorim.

(40) "Carboxylic acid amide (CAA) fungicides" (Fungicide Resistance Action Committee (FRAC) code 40) are proposed to inhibit phospholipid biosynthesis and cell wall deposition. Inhibition of these processes prevents growth and leads to death of the target fungus. Carboxylic acid amide fungicides include cinnamic acid amides, valinamide carbamates, carbamates and mandelic acid amides. The cinnamic acid amides include dimethomorph and flumorph. The valinamide carbamates include benthiavalicarb, benthiavalicarb-isopropyl, iprovalicarb, valifenalate and valiphenal. The carbamates include tolprocarb. The mandelic acid amides include mandipropamid, N-[2-[4-[[3-(4-chlorophenyl)-2-propyn-1-yl]oxy]-3-methoxyphenyl]ethyl]-3-methyl-2-[(methylsulfonyl)-amino]butanamide and N-[2-[4-[[3-(4-chlorophenyl)-2-propyn-1-yl]oxy]-3-methoxyphenyl]-ethyl]-3-methyl-2-[(ethyl sulfonyl)amino]butanamide.

(41) "Tetracycline antibiotic fungicides" (Fungicide Resistance Action Committee (FRAC) code 41) inhibit growth of fungi by affecting complex 1 nicotinamide adenine dinucleotide (NADH) oxidoreductase. Examples include oxytetracycline.

(42) "Thiocarbamate fungicides" (Fungicide Resistance Action Committee (FRAC) code 42) include methasulfocarb.

(43) "Benzamide fungicides" (Fungicide Resistance Action Committee (FRAC) code 43) inhibit growth of fungi by delocalization of spectrin-like proteins. Examples include acylpicolide fungicides such as fluopicolide.

(44) "Host plant defense induction fungicides" (Fungicide Resistance Action Committee (FRAC) code P) induce host plant defense mechanisms. Host plant defense induction fungicides include benzothiadiazoles, benzisothiazoles and thiadiazolecarboxamides. The benzothiadiazoles include acibenzolar-S-methyl. The benzisothiazoles include probenazole. The thiadiazolecarboxamides include tiadinil and isotianil.

(45) "Multi-site contact fungicides" inhibit fungal growth through multiple sites of action and have contact/preventive activity. This class of fungicides includes: (45.1) "copper fungicides" (Fungicide Resistance Action Committee (FRAC) code M1)", (45.2) "sulfur fungicides" (Fungicide Resistance Action Committee (FRAC) code M2), (45.3) "dithiocarbamate fungicides" (Fungicide Resistance Action Committee (FRAC) code M3), (45.4) "phthalimide fungicides" (Fungicide Resistance Action Committee (FRAC) code M4), (45.5) "chloronitrile fungicides" (Fungicide Resistance Action Committee (FRAC) code M5), (45.6) "sulfamide fungicides" (Fungicide Resistance Action Committee (FRAC) code M6), (45.7) "guanidine fungicides" (Fungicide Resistance Action Committee (FRAC) code M7), (45.8) "triazine fungicides" (Fungicide Resistance Action Committee (FRAC) code M8) and (45.9) "quinone fungicides" (Fungicide Resistance Action Committee (FRAC) code M9). "Copper fungicides" are inorganic compounds containing copper, typically in the copper(II) oxidation state; examples include copper oxychloride, copper sulfate and copper hydroxide, including compositions such as Bordeaux mixture (tribasic copper sulfate). "Sulfur fungicides" are inorganic chemicals containing rings or chains of sulfur atoms; examples include elemental sulfur. "Dithiocarbamate fungicides" contain a dithiocarbamate molecular moiety; examples include mancozeb, metiram, propineb, ferbam, maneb, thiram, zineb and ziram. "Phthalimide fungicides" contain a phthalimide molecular moiety; examples include folpet, captan and captafol. "Chloronitrile fungicides" contain an aromatic ring substituted with chloro and cyano; examples include chlorothalonil. "Sulfamide fungicides" include dichlofluanid and tolyfluanid. "Guanidine fungicides" include dodine, guazatine, iminoctadine albesilate and iminoctadine triacetate. "Triazine fungicides" include anilazine. "Quinone fungicides" include dithianon.

(46) "Fungicides other than fungicides of classes (1) through (45)" include certain fungicides whose mode of action may be unknown. These include: (46.1) "thiazole carboxamide fungicides" (Fungicide Resistance Action Committee (FRAC) code U5), (46.2) "phenylacetamide fungicides" (Fungicide Resistance Action Committee (FRAC) code U6), (46.3) "arylphenylketone fungicides" (Fungicide Resistance Action Committee (FRAC) code U8) and (46.4) "triazolopyrimidine fungicides". The thiazole carboxamides include ethaboxam. The phenylacetamides include cyflufenamid and N-[[(cyclopropylmethoxy)-amino][6-(difluoromethoxy)-2,3-difluorophenyl]-methylene]benzeneacetamide. The arylphenylketones include benzophenones such as metrafenone and benzoylpyridines such as pyriofenone. The triazolopyrimidines include ametoctradin. Class (46) (i.e. "Fungicides other than classes (1) through (45)") also includes bethoxazin, fluxapyroxad, neoasozin (ferric methanearsonate), pyrrolnitrin, quinomethionate, tebufloquin, isofetamid, N-[2-[4-[[3-(4-chlorophenyl)-2-propyn-1-yl]oxy]-3-methoxyphenyl]ethyl]-3-methyl-2-[(methyl sulfonyl)amino]butanamide, N-[2-[4-[[3-(4-chlorophenyl)-2-propyn-1-yl]oxy]-3-methoxyphenyl]ethyl]-3-methyl-2-[(ethyl sulfonyl)amino]butanamide, 2-[[2-fluoro-5-(trifluoromethyl)phenyl]thio]-2-[3-(2-methoxyphenyl)-2-thiazolidinylidene]acetonitrile, 3-[5-(4-chlorophenyl)-2,3-dimethyl-3-isoxazolidinyl]pyridine, 4-fluorophenyl N-[1-[[[1-(4-cyanophenyl)ethyl]sulfonyl]methyl]propyl]carbamate, 5-chloro-6-(2,4,6-trifluorophenyl)-7-(4-methylpiperidin-1-yl)[1,2,4]triazolo[1,5-α]pyrimidine, N-(4-chloro-2-nitrophenyl)-N-ethyl-4-methylbenzenesulfonamide, N-[[(cyclopropylmethoxy)amino][6-(difluoromethoxy)-2,3-difluorophenyl]methylene]benzeneacetamide, N'-[4-[4-chloro-3-(trifluoromethyl)-phenoxy]-2,5-dimethylphenyl]-N-ethyl-N-methylmethanimidamide, 1-[(2-propenylthio)-carbonyl]-2-(1-methylethyl)-4-(2-methylphenyl)-5-amino-1H-pyrazol-3-one, N'-[4-[[3-[(4-chlorophenyl)methyl]-1,2,4-thiadiazol-5-yl]oxy]-2,5-dimethylphenyl]-N-ethyl-N-methylmethanimidamide, 1,1-dimethylethyl N-[6-[[[[(1-methyl-1H-tetrazol-5-yl)phenylmethylene]-amino]oxy]methyl]-2-pyridinyl]carbamate, 3-butyn-1-yl N-[6-[[[[(1-methyl-1H-tetrazol-5-yl)phenylmethylene]amino]oxy] methyl]-2-pyridinyl]carbamate, 2,6-dimethyl-1H,5H-[1,4] dithiino[2,3-c:5,6-c']dipyrrole-1,3,5,7(2H,6H)-tetrone, 5-fluoro-2-[(4-methylphenyl)-methoxy]-4-pyrimidinamine, 5-fluoro-2-[(4-fluorophenyl)methoxy]-4-pyrimidinamine, α-[3-(4-chloro-2-fluorophenyl)-5-(2,4-difluorophenyl)isoxazol-4-yl]pyrid-3-ylmethanol, (αS)-[3-(4-chloro-2-fluorophenyl)-5-(2,4-difluorophenyl)isoxazol-4-yl]pyrid-3-ylmethanol and (αR)-[3-(4-chloro-2-fluorophenyl)-5-(2,4-difluorophenyl)isoxazol-4-yl]pyrid-3-ylmethanol.

Therefore of note is a mixture (i.e. composition) comprising a compound of Formula 1 and at least one fungicidal compound selected from the group consisting of the aforedescribed classes (1) through (46). Also of note is a composition comprising said mixture (in fungicidally effective amount) and further comprising at least one additional component selected from the group consisting of surfactants, solid diluents and liquid diluents. Of particular note is a mixture (i.e. composition) comprising a compound of Formula 1 and at least one fungicidal compound selected from the group of specific compounds listed above in connection with classes (1) through (46). Also of particular note is a composition comprising said mixture (in fungicidally effective amount) and further comprising at least one additional surfactant selected from the group consisting of surfactants, solid diluents and liquid diluents.

Examples of other biologically active compounds or agents with which compounds of this invention can be formulated are: insecticides such as abamectin, acephate, acetamiprid, acrinathrin, amidoflumet (S-1955), avermectin, azadirachtin, azinphos-methyl, bifenthrin, bifenazate, buprofezin, carbofuran, cartap, chlorantraniliprole, chlorfenapyr, chlorfluazuron, chlorpyrifos, chlorpyrifos-methyl, chromafenozide, clothianidin, cyantraniliprole (3-bromo-1-(3-chloro-2-pyridinyl)-N-[4-cyano-2-methyl-6-[(methyl-amino)carbonyl]phenyl]-1H-pyrazole-5-carboxamide), cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, meperfluthrin, metaflumizone, metaldehyde, methamidophos, methidathion, methomyl, methoprene, methoxychlor, methoxyfenozide, metofluthrin, milbemycin oxime, monocrotophos, nicotine, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen (BSN 2060), spirotetramat, sulfoxaflor, sulprofos, tebufenozide, teflubenzuron, tefluthrin, terbufos, tetrachlorvinphos, tetramethylfluthrin, thiacloprid, thiamethoxam, thiodicarb, thiosultap-sodium, tolfenpyrad, tralomethrin, triazamate, trichlorfon and triflumuron; and biological agents including entomopathogenic bacteria, such as *Bacillus thuringiensis* subsp. *aizawai*, *Bacillus thuringiensis* subsp. *kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

Compounds of this invention and compositions thereof can be applied to plants genetically transformed to express proteins toxic to invertebrate pests (such as *Bacillus thuringiensis* delta-endotoxins). The effect of the exogenously applied fungicidal compounds of this invention may be synergistic with the expressed toxin proteins.

General references for agricultural protectants (i.e. insecticides, fungicides, nematocides, acaricides, herbicides and biological agents) include *The Pesticide Manual*, 13th Edition, C. D. S. Tomlin, Ed., British Crop Protection Council, Farnham, Surrey, U. K., 2003 and *The BioPesticide Manual*, 2nd Edition, L. G. Copping, Ed., British Crop Protection Council, Farnham, Surrey, U. K., 2001.

For embodiments where one or more of these various mixing partners are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of diseases controlled beyond the spectrum controlled by the compound of Formula 1 alone.

In certain instances, combinations of a compound of this invention with other biologically active (particularly fungicidal) compounds or agents (i.e. active ingredients) can result in a greater-than-additive (i.e. synergistic) effect. Reducing the quantity of active ingredients released in the environment while ensuring effective pest control is always desirable. When synergism of fungicidal active ingredients occurs at application rates giving agronomically satisfactory levels of fungal control, such combinations can be advantageous for reducing crop production cost and decreasing environmental load.

Of note is a combination of a compound of Formula 1 with at least one other fungicidal active ingredient. Of particular note is such a combination where the other fungicidal active ingredient has different site of action from the compound of Formula 1. In certain instances, a combination with at least one other fungicidal active ingredient having a similar spectrum of control but a different site of action will be particularly advantageous for resistance management. Thus, a composition of the present invention can further comprise a biologically effective amount of at least one additional fungicidal active ingredient having a similar spectrum of control but a different site of action.

Of particular note are compositions which in addition to compound of Formula 1 include at least one compound selected from the group consisting of (1) alkylenebis(dithiocarbamate) fungicides; (2) cymoxanil; (3) phenylamide fungicides; (4) proquinazid (6-iodo-3-propyl-2-propyloxy-4 (3H)-quinazolinone); (5) chlorothalonil; (6) carboxamides acting at complex II of the fungal mitochondrial respiratory electron transfer site; (7) quinoxyfen; (8) metrafenone; (9) cyflufenamid; (10) cyprodinil; (11) copper compounds; (12) phthalimide fungicides; (13) fosetyl-aluminum; (14) benzimidazole fungicides; (15) cyazofamid; (16) fluazinam; (17) iprovalicarb; (18) propamocarb; (19) validomycin; (20) dichlorophenyl dicarboximide fungicides; (21) zoxamide; (22) fluopicolide; (23) mandipropamid; (24) carboxylic acid amides acting on phospholipid biosynthesis and cell wall deposition; (25) dimethomorph; (26) non-DMI sterol biosynthesis inhibitors; (27) inhibitors of demethylase in sterol biosynthesis; (28) $bc_1$ complex fungicides; and salts of compounds of (1) through (28).

Further descriptions of classes of fungicidal compounds are provided below.

Sterol biosynthesis inhibitors (group (27)) control fungi by inhibiting enzymes in the sterol biosynthesis pathway. Demethylase-inhibiting fungicides have a common site of action within the fungal sterol biosynthesis pathway, involving inhibition of demethylation at position 14 of lanosterol or 24-methylene dihydrolanosterol, which are precursors to sterols in fungi. Compounds acting at this site are often referred to as demethylase inhibitors, DMI fungicides, or DMIs. The demethylase enzyme is sometimes referred to by other names in the biochemical literature, including cytochrome P-450 (14DM). The demethylase enzyme is described in, for example, *J. Biol. Chem.* 1992, 267, 13175-79 and references cited therein. DMI fungicides are divided between several chemical classes: azoles (including triazoles and imidazoles), pyrimidines, piperazines and pyridines. The triazoles include azaconazole, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole and uniconazole. The imidazoles include clotrimazole, econazole, imazalil, isoconazole, miconazole, oxpoconazole, prochloraz and triflumizole. The pyrimidines include fenarimol, nuarimol and triarimol. The piperazines include triforine. The pyridines include buthiobate and pyrifenox. Biochemical investigations have shown that all of the above mentioned fungicides are DMI fungicides as described by K. H. Kuck et al. in *Modern Selective Fungicides-Properties, Applications and Mechanisms of Action*, H. Lyr (Ed.), Gustav Fischer Verlag: New York, 1995, 205-258.

$bc_1$ Complex Fungicides (group 28) have a fungicidal mode of action which inhibits the $bc_1$ complex in the mitochondrial respiration chain. The $bc_1$ complex is sometimes referred to by other names in the biochemical literature, including complex III of the electron transfer chain, and ubihydroquinone:cytochrome c oxidoreductase. This complex is uniquely identified by Enzyme Commission number EC1.10.2.2. The $bc_1$ complex is described in, for example, *J. Biol. Chem.* 1989, 264, 14543-48; *Methods Enzymol.* 1986, 126, 253-71; and references cited therein. Strobilurin fungicides such as azoxystrobin, dimoxystrobin, enestroburin (SYP-Z071), fluoxastrobin, kresoxim-methyl, metominostrobin, orysastrobin, picoxystrobin, pyraclostrobin, pyrametostrobin, pyraoxystrobin and trifloxystrobin are known to have this mode of action (H. Sauter et al., *Angew. Chem. Int. Ed.* 1999, 38, 1328-1349). Other fungicidal compounds that inhibit the $bc_1$ complex in the mitochondrial respiration chain include famoxadone and fenamidone.

Alkylenebis(dithiocarbamate)s (group (1)) include compounds such as mancozeb, maneb, propineb and zineb. Phenylamides (group (3)) include compounds such as metalaxyl, benalaxyl, furalaxyl and oxadixyl. Carboxamides (group (6)) include compounds such as boscalid, carboxin, fenfuram, flutolanil, furametpyr, mepronil, oxycarboxin, thifluzamide, penthiopyrad and N-[2-(1,3-dimethylbutyl)phenyl]-5-fluoro-1,3-dimethyl-1H-pyrazole-4-carboxamide (PCT Patent Publication WO 2003/010149), and are known to inhibit mitochondrial function by disrupting complex II (succinate dehydrogenase) in the respiratory electron transport chain. Copper compounds (group (11)) include compounds such as copper oxychloride, copper sulfate and copper hydroxide, including compositions such as Bordeaux mixture (tribasic copper sulfate). Phthalimides (group (12)) include compounds such as folpet and captan. Benzimidazole fungicides (group (14)) include benomyl and carbendazim. Dichlorophenyl dicarboximide fungicides (group (20)) include chlozolinate, dichlozoline, iprodione, isovaledione, myclozolin, procymidone and vinclozolin.

Non-DMI sterol biosynthesis inhibitors (group (26)) include morpholine and piperidine fungicides. The morpholines and piperidines are sterol biosynthesis inhibitors that have been shown to inhibit steps in the sterol biosynthesis pathway at a point later than the inhibitions achieved by the DMI sterol biosynthesis (group (27)). The morpholines include aldimorph, dodemorph, fenpropimorph, tridemorph and trimorphamide. The piperidines include fenpropidin.

The control efficacy of compounds of this invention on specific pathogens is demonstrated in TABLE A below. The pathogen control protection afforded by the compounds is not limited, however, to the species described in Tests A-E below. Descriptions of the compounds are provided in Index Table A. The following abbreviations are used in the index table: Ph is phenyl, "Cmpd. No." means compound number, and "Ex." stands for "Example" and is followed by a number indicating in which example the compound is prepared.

INDEX TABLE A

| Cmpd. No. | $Q^2$ | $R^{3b}$ | m.p. (° C.) |
|---|---|---|---|
| 1 | 2-Cl-4-F—Ph | [cyclopropyl-CH=CH-] | 141-143 |
| 2 | 2-Cl-4-F—Ph | [cyclopropyl-C≡C-] | 114-117 |
| 3 (Ex. 1) | 2-Cl-4-F—Ph | [pyrazol-1-yl] | 192-194 |
| 4 | 2-Cl-4-F—Ph | [3-CF$_3$-pyrazol-1-yl] | 216-219 |
| 5 | 2-Cl-4-F—Ph | [HC≡C-CH$_2$-O-CH$_3$] | 165-168 |
| 6 | 2-Cl-4-F—Ph | [H$_2$C=CH-CH$_2$-O-CH$_3$] | 146-149 |
| 7 | 2-Cl-4-F—Ph | [oxiranyl-CH$_2$-O-CH$_3$] | 170-172 |
| 8 | 2-Cl-4-F—Ph | [oxiranyl-] | 161-164 |

INDEX TABLE A-continued

| Cmpd. No. | $Q^2$ | $R^{3b}$ | m.p. (° C.) |
|---|---|---|---|
| 9 (Ex. 3) | 2-Cl-4-F—Ph | [(CH$_3$)$_2$CH-CH$_2$-CH$_2$-O-CH$_3$] | 159-162 |
| 10 (Ex. 2) | 2-Cl-4-F—Ph | [cyclopropyl-CH$_2$-O-CH$_3$] | 167-170 |
| 11 | 2-Cl-4-F—Ph | [HO-N=CH-CH$_3$] | 224-227 |
| 12 | 2-Cl-4-F—Ph | [(CH$_3$)$_2$N-N=CH-CH$_3$] | 175-178 |
| 13 | 2-Cl-4-F—Ph | [H$_3$C-CH$_2$-CH$_2$-O-CH$_3$] | 177-180 |
| 14 | 2-Cl-4-F—Ph | [H$_3$C-O-N=CH-CH$_3$] | 139-142 |
| 15 | 2-Cl-4-F—Ph | [tetrahydrofuran-2-yl-CH$_2$-O-CH$_3$] | 172-175 |
| 16 | 2-Cl-4-F—Ph | [1-methylcyclobutyl-CH$_2$-O-CH$_3$] | 146-149 |
| 17 | 2-Cl-4-F—Ph | [Cl-C(=CH-)-CH$_2$-O-CH$_3$] | 148-150 |
| 18 | 2-Cl-4-F—Ph | [Cl-CH=CH-CH$_2$-O-CH$_3$] | 174-177 |
| 19 | 2-Cl-4-F—Ph | [1,3-dioxolan-2-yl-CH$_2$-O-CH$_3$] | 162-165 |

BIOLOGICAL EXAMPLES OF THE INVENTION

General protocol for preparing test suspensions for Tests A-E: the test compounds were first dissolved in acetone in an amount equal to 3% of the final volume and then suspended at the desired concentration (in ppm) in acetone and purified water (50/50 mix by volume) containing 250 ppm of the surfactant Trem® 014 (polyhydric alcohol esters). The resulting test suspensions were then used in Tests A-E. Spraying a 200 ppm test suspension to the point of run-off on the test plants was the equivalent of a rate of 800 g/ha.

Test A

The test suspension was sprayed to the point of run-off on wheat seedlings. The following day the seedlings were inoculated with a spore suspension of *Puccinia recondita* f. sp. *tritici* (the causal agent of wheat leaf rust) and incubated in a saturated atmosphere at 20° C. for 24 h, and then moved to a growth chamber at 20° C. for 6 days, after which time visual disease ratings were made.

Test B

The test suspension was sprayed to the point of run-off on wheat seedlings. The following day the seedlings were inoculated with a spore suspension of *Septoria tritici* (the causal agent of wheat leaf blotch) and incubated in a saturated atmosphere at 24° C. for 48 h, and then moved to a growth chamber at 20° C. for 19 days, after which time visual disease ratings were made.

Test C

The test suspension was sprayed to the point of run-off on tomato seedlings. The following day the seedlings were inoculated with a spore suspension of *Botrytis cinerea* (the causal agent of tomato *Botrytis*) and incubated in a saturated atmosphere at 20° C. for 48 h, and then moved to a growth chamber at 24° C. for 3 days, after which time visual disease ratings were made.

Test D

The test suspension was sprayed to the point of run-off on wheat seedlings. The following day the seedlings were inoculated with a spore dust of *Blumeria graminis* f. sp. *tritici*, also known as *Erysiphe graminis* f. sp. *tritici* (the causal agent of wheat powdery mildew) and incubated in a growth chamber at 20° C. for 8 days, after which time visual disease ratings were made.

Test E

The test suspension was sprayed to the point of run-off on wheat seedlings. The following day the seedlings were inoculated with a spore suspension of *Septoria nodorum* (the causal agent of *Septoria* glume blotch) and incubated in a saturated atmosphere at 24° C. for 48 h, and then moved to a growth chamber at 20° C. for 9 days, after which time visual disease ratings were made.

Results for Tests A-E are given in Table A. In the Table, a rating of 100 indicates 100% disease control and a rating of 0 indicates no disease control (relative to the controls). All results are for compounds tested at 200 ppm except where followed by an asterisk "*" which indicates the compound was tested at 250 ppm. A dash (-) indicates no test results.

TABLE A

| Cmpd. No | Test A | Test B | Test C | Test D | Test E |
|---|---|---|---|---|---|
| 1 | 68 | — | 0 | 98 | 0 |
| 2 | 95 | — | 98 | 98 | 100 |
| 3 | 68 | — | 59 | 81 | 98 |
| 4 | 0 | — | 0 | 0 | 0 |
| 5 | 100 | 99 | 98 | 99 | — |
| 6 | 99 | 99 | 99 | 95 | — |
| 7 | 99 | — | 97 | 93 | — |
| 8 | 90 | 95 | 30 | 27 | 0 |
| 9 | 9 | 87 | 0 | 21* | 0 |
| 10 | 99 | 96 | 12 | 94 | 100 |
| 11 | 86 | 98 | 15 | 69 | 0 |
| 12 | 89 | 95 | 97 | 73 | 0 |
| 13 | 0 | 98 | 0 | 98 | — |
| 14 | 100 | 99 | 39 | 95 | — |
| 15 | 98* | 100* | 98* | 95* | — |
| 16 | 100* | 100* | 97* | 99* | — |
| 17 | 100* | 99* | 69* | 100* | — |
| 18 | 100* | 99* | 31* | 99* | — |
| 19 | 100* | 99* | 100* | 95* | — |

What is claimed is:

1. A compound selected from Formula 1, N-oxides and salts thereof,

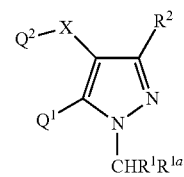

wherein $Q^1$ is a phenyl ring substituted at the 2-, 4- and 6-positions with substituents independently selected from $R^{3a}$ and $R^{3b}$; or a phenyl ring substituted at the 2- and 4-positions with substituents independently selected from $R^{3a}$ and $R^{3b}$; or a phenyl ring substituted at the 2- and 6-positions with substituents independently selected from $R^{3a}$ and $R^{3b}$;

$Q^2$ is a phenyl ring substituted at the 2-, 4- and 6-positions with substituents independently selected from $R^{3a}$ and $R^{3b}$; or a phenyl ring substituted at the 2- and 4-positions with substituents independently selected from $R^{3a}$ and $R^{3b}$; or a phenyl ring substituted at the 2- and 6-positions with substituents independently selected from $R^{3a}$ and $R^{3b}$;

X is $NR^4$ or $CHOR^{5b}$;

$R^1$ is H;

$R^{1a}$ is H;

$R^2$ is methyl;

each $R^{3a}$ is independently halogen;

each $R^{3b}$ is independently $C_5$-$C_8$ cycloalkylalkynyl, $C_4$-$C_6$ alkoxy, $C_4$-$C_6$ haloalkoxy, $C_2$-$C_6$ alkenyloxy, $C_2$-$C_6$ haloalkenyloxy, $C_3$-$C_6$ alkynyloxy, $C_4$-$C_8$ cycloalkylalkoxy, $C_4$-$C_9$ trialkylsilylalkoxy, —C(=S)$NR^{9a}R^{9b}$, —$CR^{10a}$=$NOR^{10b}$, —ON=$CR^{11a}R^{11b}$ or -A($CR^{12a}R^{12b}$)$_n$W;

each A is independently O or a direct bond;

each W is independently a 3- to 5-membered heterocyclic ring containing ring members selected from carbon atoms and 1 to 2 heteroatoms independently selected from up to 2 O and up to 2 N atoms, the ring optionally substituted with up to 2 substituents independently selected from $R^{13}$ on carbon atom ring members;

$R^4$ is H;

$R^{5b}$ is H;

each $R^{9a}$ and $R^{9b}$ is independently H or methyl;

each $R^{10a}$ is independently H, methyl or halomethyl;

each $R^{10b}$ is independently H, $C_1$-$C_3$ alkyl, $C_1$-$C_3$ haloalkyl, $C_3$-$C_4$ cycloalkyl or $C_3$-$C_4$ halocycloalkyl;

each $R^{11a}$ and $R^{11b}$ is independently H, methyl or halomethyl;
each $R^{12a}$ is independently H, cyano, halogen or methyl;
each $R^{12b}$ is independently H or methyl;
each $R^{13}$ is independently halogen, methyl, halomethyl or methoxy; and
each n is independently 0, 1 or 2;
provided that:
(a) at least one of $Q^1$ or $Q^2$ is substituted with at least one $R^{3b}$; and
(b) when n is 1 or 2, then W is linked through a carbon atom to the remainder of Formula 1.

2. A compound of claim 1 wherein
$Q^1$ is a phenyl ring substituted with 2 substituents independently selected from $R^{3a}$ and 1 substituent selected from $R^{3b}$;
$Q^2$ is a phenyl ring substituted with 1 to 3 substituents independently selected from $R^{3a}$;
X is $CHOR^{5b}$;
each $R^{3a}$ is independently Br, Cl or F;
$R^{3b}$ is $C_5$-$C_8$ cycloalkylalkynyl, $C_4$-$C_6$ alkoxy, $C_4$-$C_6$ haloalkoxy, $C_2$-$C_6$ alkenyloxy, $C_2$-$C_6$ haloalkenyloxy, $C_3$-$C_6$ alkynyloxy, $C_4$-$C_8$ cycloalkylalkoxy, $C_4$-$C_9$ trialkylsilylalkoxy, —$CR^{10a}$=$NOR^9$, —ON=$CR^{11a}R^{11b}$ or -A$(CR^{12a}R^{12b})_n$W;
W is a 3- to 5-membered heterocyclic ring containing ring members selected from carbon atoms and 1 to 2 heteroatoms independently selected from up to 2 O and up to 2 N atoms;
$R^{12a}$ is H; and
$R^{12b}$ is H.

3. A compound of claim 2 wherein
$Q^1$ is a phenyl ring substituted with 2 substituents independently selected from $R^{3a}$ which are attached at the 2- and 6-positions and 1 substituent selected from $R^{3b}$ which is attached at the 4-position;
$Q^2$ is a phenyl ring substituted with 2 substituents independently selected from $R^{3a}$ which are attached at the 2- and 6-positions; or a phenyl ring substituted with 2 substituents independently selected from $R^{3a}$ which
$R^{3b}$ is $C_5$-$C_8$ cycloalkylalkynyl, $C_4$-$C_6$ alkoxy, $C_4$-$C_6$ haloalkoxy, $C_2$-$C_6$ alkenyloxy, $C_2$-$C_6$ haloalkenyloxy, $C_3$-$C_6$ alkynyloxy, $C_4$-$C_8$ cycloalkylalkoxy, —$CR^{10a}$=$NOR^9$ or -A$(CR^{12a}R^{12b})_n$W.

4. The compound of claim 1 which is selected from the group:
α-(2-chloro-4-fluorophenyl)-5-[2,6-difluoro-4-(1H-pyrazol-1-yl)phenyl]-1,3-dimethyl-1H-pyrazole-4-methanol; and
α-(2-chloro-4-fluorophenyl)-5-[4-(2-cyclopropylethynyl)-2,6-difluorophenyl]-1,3-dimethyl-1H-pyrazole-4-methanol.

5. A fungicidal composition comprising (a) a compound of claim 1; and (b) at least one other fungicide.

6. A fungicidal composition comprising (a) a compound of claim 1; and (b) at least one additional component selected from the group consisting of surfactants, solid diluents and liquid diluents.

7. A method for controlling plant diseases caused by fungal plant pathogens comprising applying to the plant or portion thereof, or to the plant seed, a fungicidally effective amount of a compound of claim 1.

\* \* \* \* \*